(12) United States Patent
Min et al.

(10) Patent No.: US 11,530,132 B2
(45) Date of Patent: *Dec. 20, 2022

(54) COMPOSITION COMPRISING POROUS SILICA PARTICLES CARRYING A CELL FATE MODULATING FACTOR

(71) Applicant: LEMONEX INC., Seoul (KR)

(72) Inventors: Dal-Hee Min, Seoul (KR); Cheolhee Won, Seoul (KR); Sejin Park, Seoul (KR); Seongchan Kim, Gwangju-si (KR)

(73) Assignee: LEMONEX INC., Seoul (KR)

( * ) Notice: Subject to any disclaimer, the term of this patent is extended or adjusted under 35 U.S.C. 154(b) by 468 days.

This patent is subject to a terminal disclaimer.

(21) Appl. No.: 16/122,872

(22) Filed: Sep. 5, 2018

(65) Prior Publication Data

US 2019/0071314 A1  Mar. 7, 2019

Related U.S. Application Data

(60) Provisional application No. 62/554,202, filed on Sep. 5, 2017.

(51) Int. Cl.
*C01B 37/02* (2006.01)
*C12N 5/00* (2006.01)
(Continued)

(52) U.S. Cl.
CPC .............. *C01B 37/02* (2013.01); *A61K 9/501* (2013.01); *A61K 9/5115* (2013.01);
(Continued)

(58) Field of Classification Search
CPC ........ C01B 37/02; C01B 33/18; A61K 31/711; A61K 45/06; A61K 31/196;
(Continued)

(56) References Cited

U.S. PATENT DOCUMENTS 4,179,337 A  12/1979  Davis et al.
4,495,285 A   1/1985  Shimizu et al.
(Continued)

FOREIGN PATENT DOCUMENTS

AU  2009224418 B2  9/2009
CN     101652126 A  2/2010
(Continued)

OTHER PUBLICATIONS

Xu et al., Mesoporous Silica Nanoparticles for Protein Protection and Delivery, Front Chem. (Year: 2019).*
(Continued)

*Primary Examiner* — Carlos A Azpuru
(74) *Attorney, Agent, or Firm* — The PL Law Group, PLLC

(57) ABSTRACT

A composition includes porous silica particles to carry a cell fate modulating factor therein. A method for modulating cell fate includes treating various cells with the composition. The cell fate modulating factor is delivered to a stable target receptor, toxicity to subject cells for delivery may be reduced, a fate of the subject cells can be controlled through sustained release of at least 99 wt. % of the cell fate modulating factor.

11 Claims, 28 Drawing Sheets

Specification includes a Sequence Listing.

(51) Int. Cl.

| | |
|---|---|
| *A61K 9/50* | (2006.01) |
| *B01J 13/02* | (2006.01) |
| *B82Y 5/00* | (2011.01) |
| *A61K 9/51* | (2006.01) |
| *C12N 5/077* | (2010.01) |
| *A61K 31/711* | (2006.01) |
| *A61K 45/06* | (2006.01) |
| *A61K 31/352* | (2006.01) |
| *A61K 47/69* | (2017.01) |
| *A61K 31/196* | (2006.01) |
| *C12N 5/079* | (2010.01) |
| *A61K 31/706* | (2006.01) |
| *A61K 31/437* | (2006.01) |
| *C12N 5/071* | (2010.01) |
| *A61K 35/12* | (2015.01) |

(52) U.S. Cl.
CPC .......... *A61K 9/5192* (2013.01); *A61K 31/196* (2013.01); *A61K 31/352* (2013.01); *A61K 31/437* (2013.01); *A61K 31/706* (2013.01); *A61K 31/711* (2013.01); *A61K 45/06* (2013.01); *A61K 47/6923* (2017.08); *B01J 13/02* (2013.01); *B82Y 5/00* (2013.01); *C12N 5/0068* (2013.01); *C12N 5/0618* (2013.01); *C12N 5/0657* (2013.01); *C12N 5/0678* (2013.01); *A61K 2035/128* (2013.01); *C12N 2501/385* (2013.01); *C12N 2513/00* (2013.01); *C12N 2533/14* (2013.01); *C12N 2535/00* (2013.01)

(58) Field of Classification Search
CPC .............. A61K 47/6923; A61K 31/706; A61K 31/437; A61K 9/5192; A61K 9/501; A61K 9/5115; A61K 2035/128; C12N 5/0657; C12N 5/0618; C12N 5/0678; C12N 2513/00; C12N 2533/14; C12N 2535/00; C12N 5/0606; C12N 5/0619; C12N 5/0656; C12N 5/0669; C12N 5/0676; C12N 5/0696
See application file for complete search history.

(56) References Cited

U.S. PATENT DOCUMENTS

| | | | |
|---|---|---|---|
| 4,609,546 A | 9/1986 | Hiratani | |
| 4,766,106 A | 8/1988 | Katre et al. | |
| 11,129,796 B2 * | 9/2021 | Won ..................... | A61K 39/395 |
| 2009/0181096 A1 | 7/2009 | Ludwig | |
| 2010/0104650 A1 | 4/2010 | Lee et al. | |
| 2010/0255103 A1 | 10/2010 | Liong et al. | |
| 2010/0266491 A1 | 10/2010 | Farokhzad et al. | |
| 2011/0200595 A1 | 8/2011 | Gerdes et al. | |
| 2011/0256184 A1 | 10/2011 | Lei et al. | |
| 2012/0283379 A1 | 11/2012 | Auger et al. | |
| 2014/0014327 A1 | 1/2014 | Badri et al. | |
| 2014/0017327 A1 | 1/2014 | Cheng et al. | |
| 2015/0272885 A1 | 10/2015 | Ashley et al. | |
| 2018/0319822 A1 * | 11/2018 | Schoenfisch ............ | C07F 7/188 |

FOREIGN PATENT DOCUMENTS

| | | |
|---|---|---|
| CN | 101687632 A | 3/2010 |
| CN | 103751857 A | 4/2014 |
| CN | 105456198 A | 4/2016 |
| CN | 105560186 A | 5/2016 |
| CN | 110475546 A | 11/2019 |
| EP | 0 268 110 A1 | 5/1988 |
| EP | 0 270 799 A1 | 6/1988 |
| EP | 3 173 074 A1 | 5/2017 |
| EP | 3 659 585 A2 | 6/2020 |
| JP | 2013-006859 A | 1/2013 |
| JP | 2020-506972 A | 3/2020 |
| KR | 10-2010-0117433 A | 11/2010 |
| KR | 10-2011-0000297 A | 1/2011 |
| KR | 101057116 B1 | 8/2011 |
| KR | 10-2012-0025224 A | 3/2012 |
| KR | 10-2014-0010285 A | 1/2014 |
| KR | 10-2015-0014560 A | 2/2015 |
| KR | 10-2016-0011565 A | 2/2016 |
| KR | 10-2016-0011565 A1 * | 2/2016 |
| KR | 10-2016-0137109 A | 11/2016 |
| KR | 10-1754798 B1 | 7/2017 |
| KR | 10-1762825 B1 | 7/2017 |
| KR | 10-1924519 B1 | 12/2018 |
| WO | WO 2005/097677 A1 | 10/2005 |
| WO | WO 2008/105773 A2 | 9/2008 |
| WO | WO 2012/149376 A2 | 11/2012 |
| WO | WO 2016/013751 A1 | 1/2016 |
| WO | WO 2016/149378 A1 | 9/2016 |
| WO | WO2017/008059 A1 | 1/2017 |
| WO | 2018/143787 * | 9/2018 |

OTHER PUBLICATIONS

Zhou et al, Mesoporous Silica Nanopartciels For Drug and Gene Delivery, Acat Pharmaceutica Sinica B, (80): 165-177 (Year: 2018).*
International Search Report for PCT/KR2018/010388 dated Nov. 30, 2018.
Office action dated Nov. 28, 2019 from Korean Patent Office in a counterpart Korean Patent Application No. 10-2018-0106214 (all the cited references are listed in this IDS.) (English translation is also submitted herewith.).
Jonas G. Croissant et al., "Degradability and Clearance of Silicon, Organosilica, Silsesquioxane, Silica Mixed Oxide, and Mesoporous Silica Nanoparticles", Advanced Materials, vol. 29 (9), Jan. 2017.
Hironori Yamada et al., "Preparation of Colloidal Mesoporous Silica Nanoparticles with Different Diameters and Their Unique Degradation Behavior in Static Aqueous Systems", Chemistry of materials, vol. 24 (8), pp. 1462-1471, 2012.
Qianjun He et al., "The three-stage in vitro degradation behavior of mesoporous silica in simulated body fluid", Microporous and Mesoporous Materials, vol. 131, pp. 314-320, 2010.
Xinyue Huang et al., "Characterization and Comparison of Mesoporous Silica Particles for Optimized Drug Delivery", Nanomaterials and Nanotechnologies, vol. 4, (2), 2014.
Christopher R. Steven et al. "Bioinspired silica as drug delivery systems and their biocompatibility", Journal of Materials Chemistry B, vol. 2, No. 31, 2014(Jan. 1, 2014), pp. 5028-5042, XP055685292.
Wanyin Zhai et al., "Degradation of hollow mesoporous silica nanoparticles in human umbilical vein endothelial cells", J Biomed Mater, 100(V), pp. 1397-1403, 2012.
Office action dated Apr. 13, 2022 from US Patent Office in a parent U.S. Appl. No. 16/633,849.
Office action dated Jun. 7, 2022 from Japan Intellectual Property Office in a counterpart Japanese Patent Application No. 2021-075356 (all the cited references are listed in this IDS.).
Park, Hui Seong, "Novel Intracellular Protein Delivery Carriers Based on PH-Responsive Mesoporous Nanoparticles", Graduate school of Ewha Womans University, Doctoral Thesis, 2011.
Kim, Se Mi, "RGD-and Hemagglutinin Peptide- conjugated Mesoporous Silica Nanoparticles in Doxorubin resistant MCF-7 Cells", Graduate school of Soongsil University, Master's Thesis, 2013. (English abstract is included in this reference.).
Choi, Ji Ung, "Multifunctional Silica-Iron Oxide Nanocontainers for Imaging and Drug Deliver", Graduate school of Inha University, Engineering Master's Thesis, 2013 (English abstract is included in this reference).
Lin, Yu-Hsuan, Abstract of "Characterization on co-delivery of superoxide dismutase and glutathione peroxidase by using nanoparticles". National Taiwan University Thesis, 2014.
Mi-Hee Kim et al., "Facile Synthesis of Monodispersed Mesoporous Silica Nanoparticles with Ultralarge Pores and Their Application in Gene Delivery", ACS Nano (ACS Publications), vol. 5 No.5, pp. 3568-3576, 2011 (Abstract is submitted herewith).

(56) References Cited

OTHER PUBLICATIONS

Mahkam Mehrdad, "Synthesis and characterization of pH-sensitive silica nanoparticles for oral-insulin delivery", Current Drug Delivery, vol. 8, No. 6, pp. 607-611, 2011, Miyaneh, Iran, ISSN: 1875-5704, DOI: NLM21864258.

Igor I. et al., "Mesoporous Silica Nanoparticles for Intracellular Delivery of Membrane-Impermeable Proteins", Journal of the American Chemical Society vol. 129, pp. 8845-8849, 2007.

Yu-Shen Lin et al., Supporting Information, Chem. Mater. 2005, 17, 18,4570-4573, attached hereto as Appendix 1, downloaded at https://pubs.acs.org/doi/suppl/10.1021/cm051014c/suppl_file/cm051014csi20050711_121101 pdf.

Marimar Bravo Cadena, "Application of Mesoporous Silica Nanoparticles for Biocide Delivery to Plants to Prevent Pre-Harvest Losses" A thesis submitted for the degree of Doctor of Philosophy, University of Oxford Mansfield College Department of Engineering, 2018.

J. Arbiol et al., "Distributions of Noble Metal Pd and Pt in Mesoporous Silica", Applied Physics Letters, vol. 81, Issue 18, 2002, pp. 3449-3451.

Dongyuan Zhao et al., Nonionic Triblock and Star Diblock Copolymer and Oligomeric Surfactant Syntheses of Highly Ordered, Hydrothermally Stable, Mesoporous Silica Structures:, JACS (1998), 120; 6024-6036).

Vallet-Regl, M., et al. "Bone-regenerative bioceramic implants with drug and protein controlled delivery capability", Prog. Solid State Chem (2008), 36; 163-191.

Hye-Seon Shin et al." Facile Preparation of Ultra-Large Pore Mesoporous Silica Nanoparticles and Their Application tot eh Encapsulation of Large Guest Molecules", Applied Mater. Interfaces (Jan. 2014), 6; 1740-1746.

Fakhoury, Jean Raymond Garcia, "Porous silicon microparticles as an embolic agent for the treatment of hepatocellular carcinoma" The University of Texas at Austin, Dec. 31, 2011 (Abstract is submitted herewith.).

Kaasalainen, M. et al. "Size, Stability, and Porosity of Mesoporous Nanoparticles Characterized with Light Scattering" Nanoscale Research. Letters, vol. 12, No. 74, 2017.

Jadhav, S. A et al. "Porous Silica Particles: Synthesis, Physicochemical Characterization and Evaluation of Suspension Stability" Physical Chemistry: An Indian. Journal, vol. S1, No. 102, 2017.

Notice of allowance dated Jul. 12, 2022 from Japan Intellectual Property Office in a counterpart Japanese Patent Application No. 2021-056003 (all the cited references are listed in this IDS.).

\* cited by examiner 0 hr    120 hrs    360 hrs t₅₀% = about 2.5 days

<Blood cells>

A. lymphocytes

B. bone-marrow cells

<Stem cells and progenitor cells>

A. Embryonic stem cells

B. Neural progenitor cells

<*in vivo* transplantation>

Spinal cord *(in vivo)*

COMPOSITION COMPRISING POROUS SILICA PARTICLES CARRYING A CELL FATE MODULATING FACTOR

CROSS REFERENCE TO RELATED APPLICATIONS AND CLAIM OF PRIORITY

This application claims the benefit of U.S. Provisional Patent Application No. 62/554,202, filed Sep. 5, 2017, the disclosures of which are incorporated herein in their entirety by reference.

FIELD OF THE INVENTION

The present invention relates to a composition for modulating cell fate and a method for modulating cell fate.

DESCRIPTION OF THE RELATED ART

A neural differentiation method mediated by retinoic acid (RA) is one of well-known cell conversion methods incorporating small molecules for mouse embryonic stem (mES) cells. When administering RA into the cytoplasm, the RA binds to RA receptor (RAR) heterodimers localized at a nuclear membrane, of which a complex then activates signaling pathways to induce neural generation and axon outgrowth. Several distinct strategies have been introduced to generate neural differentiation from mES cells. One of the most common methods is −4/+4 RA method, which includes 4 days of embryoid body (EB) formation to activate the cells in a differentiation state, followed by another 4 days of RA treatment for neural induction. A wide range of applications have been made with a variety of modifications to the method. However, several disadvantages still exist in terms of a hanging drop culture process to induce the formation of EB, such as a limited EB volume, impracticable media change, and complicated procedure. Another RA-based method was also introduced with consistent addition of RA to monolayer culture of mES cells and has successfully induced neural differentiation from adherent mES cell colonies, however, several limitations still exist. For example, the repetitive addition of RA indicates a requirement for a constant supply of enough RA to interact with RAR for neural induction of inactivated mES cells.

Although RA acts as one of the key factors for neural differentiation, some drawbacks must be overcome, such as its low solubility in an aqueous solution and rapid degradation by cellular metabolism. Moreover, a fine-tuned control of the RA concentration is required for the desired cell conversion. It is reported that a fate of the induced cells mediated by RA, ranging from neuron to cardiomyocyte differentiation, is highly dependent on its concentration. In addition, since RA is incorporated into a cellular membrane via diffusion, stochastic kinetics associated with RA-RAR interaction would also be concentration-dependent. However, since the addition of RA higher than its pharmacological concentration (>10 μM) during neural differentiation may result in a dramatic decrease in cell viability, an amount of RA used cannot be increased infinitely. For successful neural differentiation, therefore, it is required to enhance intracellular delivery with minimal loss of RA and mediate its sustained, sufficient supplementation to fulfill the needs of the induction process.

SUMMARY

An object of the present invention is to provide a composition including porous silica particles, which carry a cell fate modulating factor, so that the modulating factor may be carried with excellent efficiency, the carried modulating factor may be slowly released and, due to biodegradable property of the particles, at least 99% by weight ('wt. %') of the modulating factor may be released, thereby effectively modulating the fate of the subject cells.

To accomplish one or more of the above aspects, the present invention provides the followings.

1. A composition for modulating cell fate, comprising porous silica particles which carry a cell fate modulating factor on a surface of the particle or inside pores of the particle, and have t of 20 or more, at which a ratio of absorbance in Mathematical Equation 1 below reaches ½, wherein the surface of the particle or the inside the pores of the particle has been chemically modified.

$$A_t/A_0 \qquad \text{[Mathematical Equation 1]}$$

(wherein $A_0$ is an absorbance of the porous silica particles measured when 5 ml of suspension containing 1 mg/ml of porous silica particles is fed to a tubular permeable membrane having 50 kDa pores;

15 ml of a solvent substantially the same as the suspension is placed outside the permeable membrane while contacting the same;

the inside/outside of the permeable membrane are under horizontal agitation with 60 rpm at 37° C.; and $A_t$ is another absorbance of the porous silica particles measured t time after the measurement of $A_0$.)

2. The composition according to the above item 1, wherein the particle has a siloxane group on the surface of the particle or inside the pores of the particle.

3. The composition according to the above item 1, wherein the cell fate modulating factor is a gene encoding: at least one selected from 3-isobutyl-1-methylxanthine, CHIR, KY02111, DZNep, tranylcypromine, LDN, digoxin, nicotinamide, IWP2, IWP4, XAV939, TTNPB, PD0325901, A83-01, hiazovivin, DMH1, rosiglitazone, SB-431542, pifithrin-alpha, FSK, IDE1, IDE2, DAPT, CYC, PDBu, retinoic acid, ascorbic acid, dexamethasone, 5-azacytidine, taurine, Kartogenin, ursolic acid, SR1555, halofunginone, CHIR99021, valproic acid, Dkk1, Lefty A, activin A, GATA4, Foxa1, Foxa2, Mef2c, BMPs, IGF, HGF, WNT, FGF, KGF, bFGF, Klf4, CRX, RAX, OTX2, Ascl1, NFIA, NFIB, Fezf2, Hmga2, VEGF, LIF, TGF-β, SOX2, Noggin, nodal, Bm2, Mytl1, NeuroD1, Hnf1a, Foxa3, Tbx5, Tymosin beta4, Tbx5, EGF, SOXs, Bestrophin1, Ctip2, NeuroG2, Atf5, Prox1, Hnf4a, OCT4, TERT, c-myc, insulin, FGFs, interleukins, miR-124 family, miR-9 family, miR-155 family, miR-302 family, miR-367 family and miR-21 family; or at least one selected from the group consisting of Dkk1, Lefty A, activin A, GATA4, Foxa1, Foxa2, Mef2c, BMPs, IGF, HGF, WNT, FGF, KGF, bFGF, Klf4, CRX, RAX, OTX2, Ascl1, NFIA, NFIB, Fezf2, Hmga2, VEGF, LIF, TGF-β, SOX2, Noggin, nodal, Bm2, Mytl1, NeuroD1, Hnf1a, Foxa3, Tbx5, Tymosin beta4, Tbx5, EGF, SOXs, Bestrophin1, Ctip2, NeuroG2, Atf5, Prox1, Hnf4a, OCT4, TERT, c-myc, insulin and interleukins.

4. The composition according to the above item 1, wherein the cell fate modulating factor is at least one selected from the group consisting of retinoic acid, CYC, activin A, BMP-4, KGF, bFGF, Noggin, Wnt, Oct4, Sox2, Klf4, c-myc, Nanog, TERT, miR-21, 5-azacytidine, Kortogenin, CHIR, TGF-β Inhibitor, FSK, DZNep and TGFbeta-1.

5. The composition according to the above item 1, wherein the cell is at least one selected from the group consisting of: embryonic stem cell, adult stem cell, induced multipotent stem cell, mesenchymal stem cell, dermoblast, lymphocyte, myelocyte, neural progenitor cell, spinal cell, adipocyte, hepatocyte, dermal cell, hemocyte, myeloblast, fibroblast, endothelial cell, nerve cell, muscle cell, immunocyte, myocardial cell, brain cell, bone cell, oral cell, periodontal cell, hair follicle cell, mucosa cell, epithelial cell, mesenchmal cell, mesenchymal cell, placetocyte, cord blood cell, stem cell, gastrointestinal tract cell, amnion cell, retinal cell, cartilage cell, pancreatic cell, pancreatic beta cell, vascular cell and lung fibroblast cell.

6. The composition according to the above item 1, wherein the particle has at least one functional group selected from the group consisting of aldehyde, keto, carbamate, sulfate, sulfonate, amino, amine, aminoalkyl, silyl, carboxyl, sulfonic acid, thiol, ammonium, sulfhydryl, phosphate, ester, imide, thioimide, keto, ether, indene, sulfonyl, methyl phosphonate, polyethylene glycol, substituted or non-substituted $C_1$ to $C_{30}$ alkyl, substituted or non-substituted $C_3$ to $C_{30}$ cycloalkyl, substituted or non-substituted $C_6$ to $C_{30}$ aryl and $C_1$ to $C_{30}$ ester groups on the surface of the particle or inside the pores of the particle.

7. The composition according to the above item 1, wherein the particle has at least one selected from the group consisting of amino, amine, PEG, propyl, octyl, carboxyl, thiol, sulfonic acid, methyl phosphonate and aldehyde groups on the surface of the particle or inside the pores of the particle.

8. The composition according to the above item 1, wherein the maximum amount of releasing the cell fate modulating factor carried in the particle is 99% by weight or more.

9. The composition according to the above item 1, wherein the pores in the particle have an average diameter of 1 to 25 nm, a pore volume of 0.3 to 2 ml/g, and a BET surface area of 200 to 1500 $m^2/g$.

10. The composition according to the above item 1, wherein the pores in the particle have an average diameter of 7 to 23 nm, a pore volume of 0.59 to 1.69 ml/g and a BET surface area of 250 to 950 $m^2/g$.

11. A cell fate modulating method, comprising treating at least one culture medium selected from the group consisting of embryonic stem cell, adult stem cell, induced multipotent stem cell, mesenchymal stem cell, dermoblast, lymphocyte, myelocyte, neural progenitor cell, spinal cell, adipocyte, hepatocyte, dermal cell, hemocyte, myeloblast, fibroblast, endothelial cell, nerve cell, muscle cell, immunocyte, myocardial cell, brain cell, bone cell, oral cell, periodontal cell, hair follicle cell, mucosa cell, epithelial cell, mesenchmal cell, mesenchymal cell, placetocyte, cord blood cell, stem cell, gastrointestinal tract cell, amnion cell, retinal cell, cartilage cell, pancreatic cell, pancreatic beta cell, vascular cell and lung fibroblast cell with the composition according to the above item 1 or 2.

12. The modulating method according to the above item 11, wherein the cell fate modulating factor is a gene encoding at least one selected from 3-isobutyl-1-methylxanthine, CHIR, KY02111, DZNep, tranylcypromine, LDN, digoxin, nicotinamide, IWP2, IWP4, XAV939, TTNPB, PD0325901, A83-01, hiazovivin, DMH1, rosiglitazone, SB-431542, pifithrin-alpha, FSK, IDE1, IDE2, DAPT, CYC, PDBu, retinoic acid, ascorbic acid, dexamethasone, 5-azacytidine, taurine, Kartogenin, ursolic acid, SR1555, halofunginone, CHIR99021, valproic acid, Dkk1, Lefty A, activin A, GATA4, Foxa1, Foxa2, Mef2c, BMPs, IGF, HGF, WNT, FGF, KGF, bFGF, Klf4, CRX, RAX, OTX2, Ascl1, NFIA, NFIB, Fezf2, Hmga2, VEGF, LIF, TGF-β, SOX2, Noggin, nodal, Bm2, Mytl1, NeuroD1, Hnf1a, Foxa3, Tbx5, Tymosin beta4, Tbx5, EGF, SOXs, Bestrophin1, Ctip2, NeuroG2, Atf5, Prox1, Hnf4a, OCT4, TERT, c-Myc, insulin, FGFs, interleukins, miR-124 family, miR-9 family, miR-155 family, miR-302 family, miR-367 family and miR-21 family; or at least one selected from the group consisting of Dkk1, Lefty A, activin A, GATA4, Foxa1, Foxa2, Mef2c, BMPs, IGF, HGF, WNT, FGF, KGF, bFGF, Klf4, CRX, RAX, OTX2, Ascl1, NFIA, NFIB, Fezf2, Hmga2, VEGF, LIF, TGF-β, SOX2, Noggin, nodal, Bm2, Mytl1, NeuroD1, Hnf1a, Foxa3, Tbx5, Tymosin beta4, Tbx5, EGF, SOXs, Bestrophin1, Ctip2, NeuroG2, Atf5, Prox1, Hnf4a, OCT4, TERT, c-Myc, insulin and interleukins.

13. The modulating method according to the above item 11, wherein the cell fate modulating factor is at least one selected from the group consisting of retinoic acid, CYC, activin A, BMP-4, KGF, bFGF, Noggin, Wnt, Oct4, Sox2, Klf4, c-myc, Nanog, TERT, miR-21, 5-azacytidine, Kortogenin, CHIR, TGF-β Inhibitor, FSK, DZNep and TGFbeta-1.

14. The modulating method according to the above item 11, wherein the particle has at least one functional group selected from the group consisting of aldehyde, keto, carbamate, sulfate, sulfonate, amino, amine, aminoalkyl, silyl, carboxyl, sulfonic acid, thiol, ammonium, sulfhydryl, phosphate, ester, imide, thioimide, keto, ether, indene, sulfonyl, methyl phosphonate, polyethylene glycol, substituted or non-substituted $C_1$ to $C_{30}$ alkyl, substituted or non-substituted $C_3$ to $C_{30}$ cycloalkyl, substituted or non-substituted $C_6$ to $C_{30}$ aryl and $C_1$ to $C_{30}$ ester groups on the surface of the particle or inside the pores of the particle.

15. The modulating method according to the above item 11, wherein the particle has at least one selected from the group consisting of amino, amine, PEG, propyl, octyl, carboxyl, thiol, sulfonic acid, methyl phosphonate and aldehyde groups on the surface of the particle or inside the pores of the particle.

16. The modulating method according to the above item 11, wherein the maximum amount of releasing the cell fate modulating factor carried in the particle is 99% by weight or more.

17. The modulating method according to the above item 11, wherein the pores in the particle have an average diameter of 1 to 25 nm, a pore volume of 0.3 to 2 ml/g, and a BET surface area of 200 to 1500 $m^2/g$.

18. The modulating method according to the above item 11, wherein the pores in the particle have an average diameter of 7 to 23 nm, a pore volume of 0.59 to 1.69 ml/g and a BET surface area of 250 to 950 $m^2/g$.

The composition of the present invention includes the porous silica particles which carry a cell fate modulating factor, such that the modulating factor may be carried with excellent efficiency, the carried modulating factor may be slowly released and, due to biodegradable property of the particles, at least 99 wt. % of the modulating factor may be released, thereby effectively modulating the fate of the subject cell.

Figure 7A:
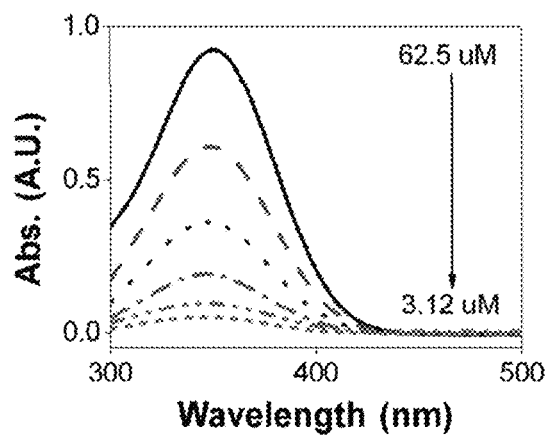
Figure 8:
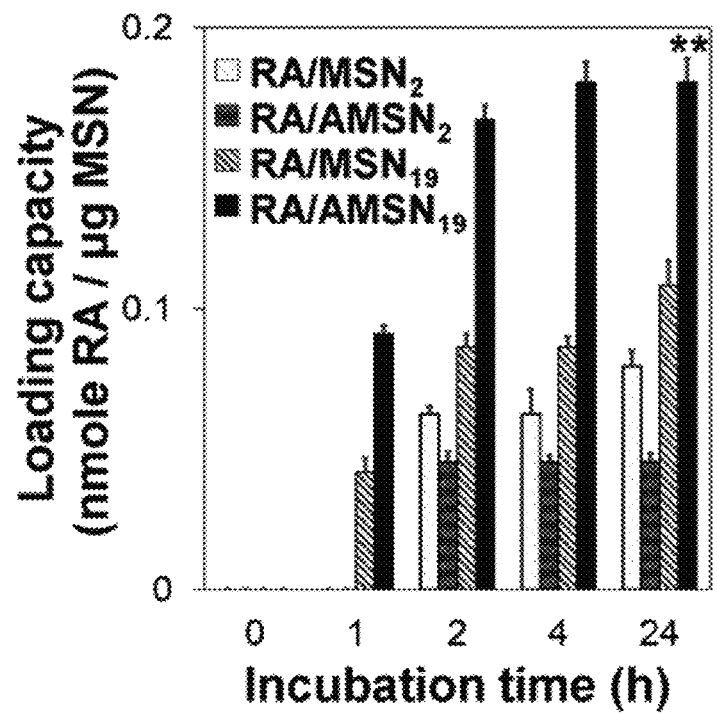
Figure 9:
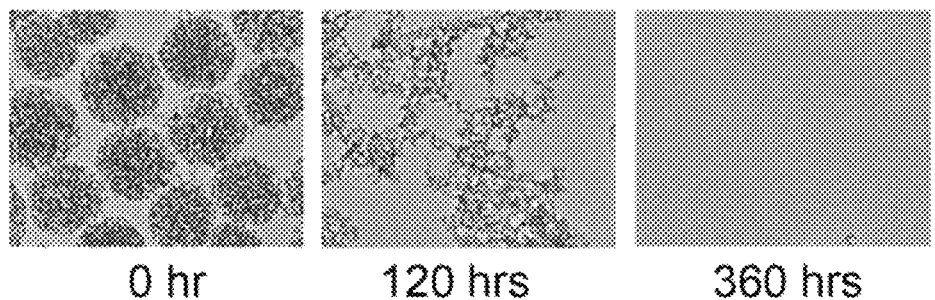
Figure 10:
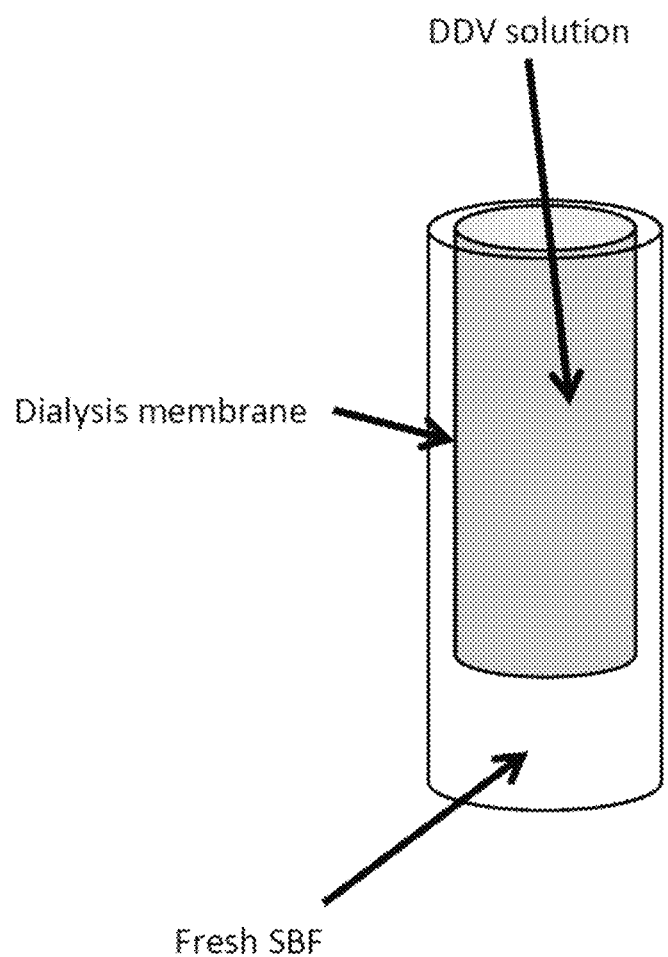
Figure 11:
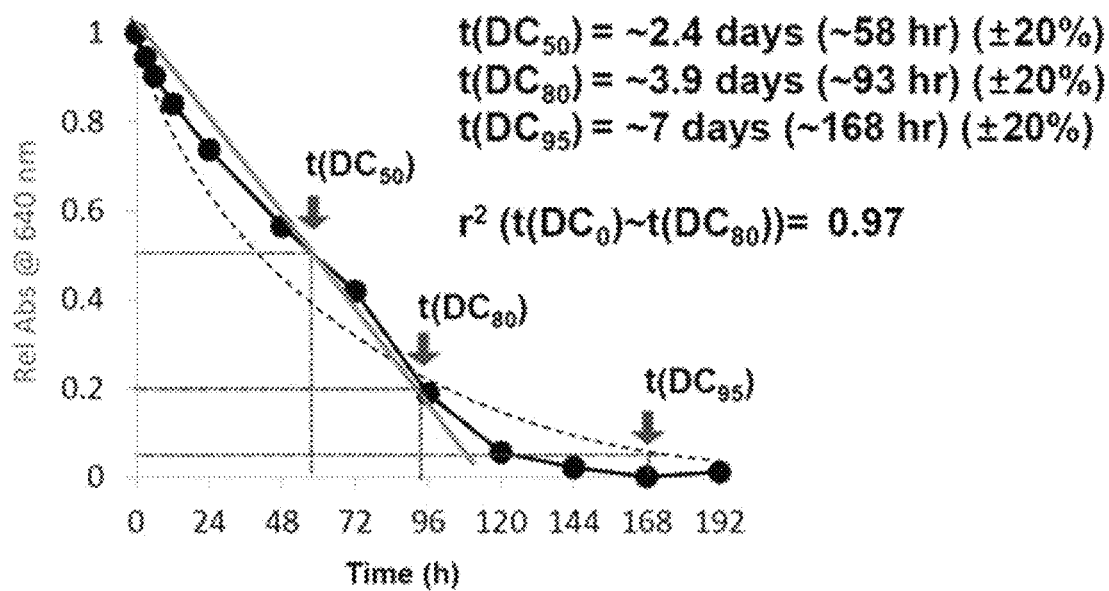
Figure 12:
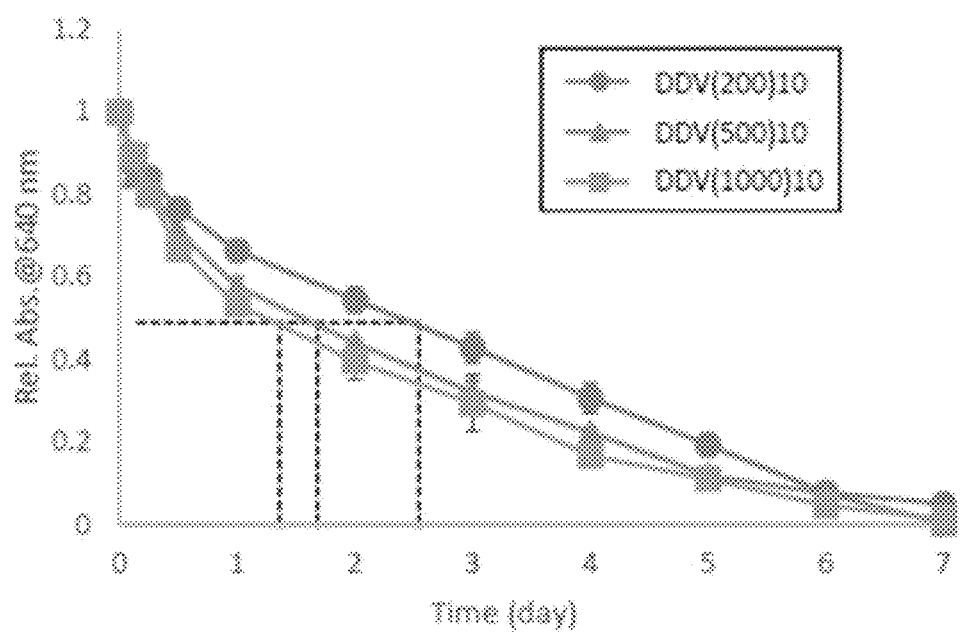
Figure 13:
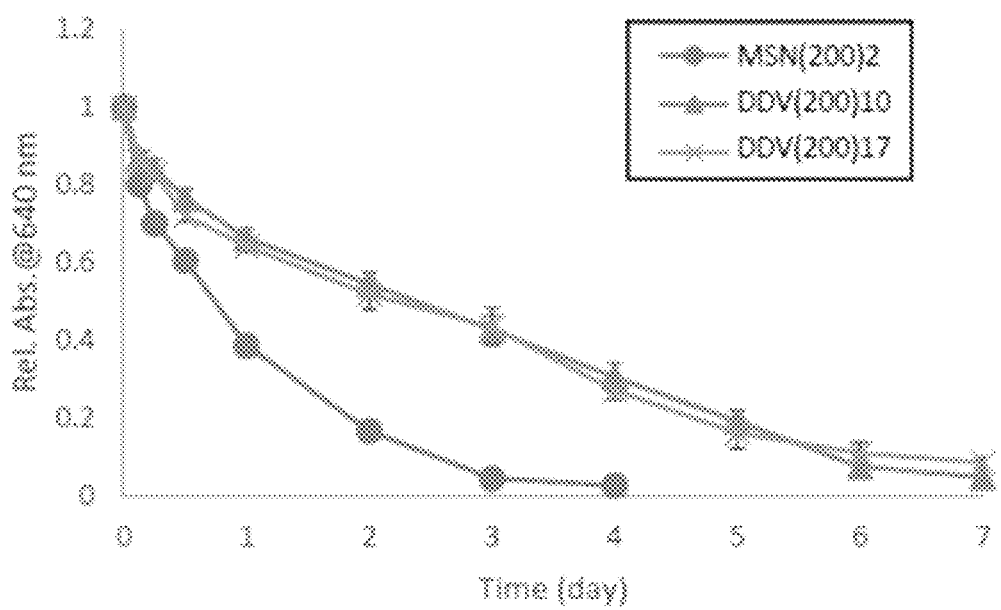
Figure 14:
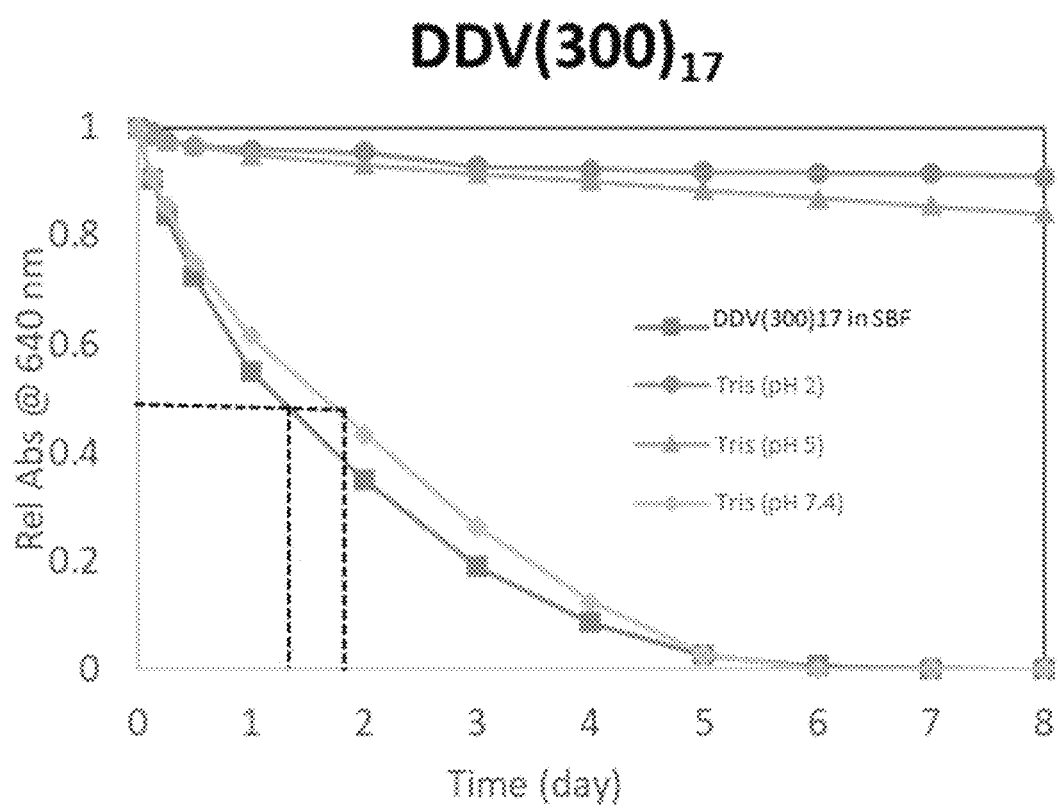
Figure 15:
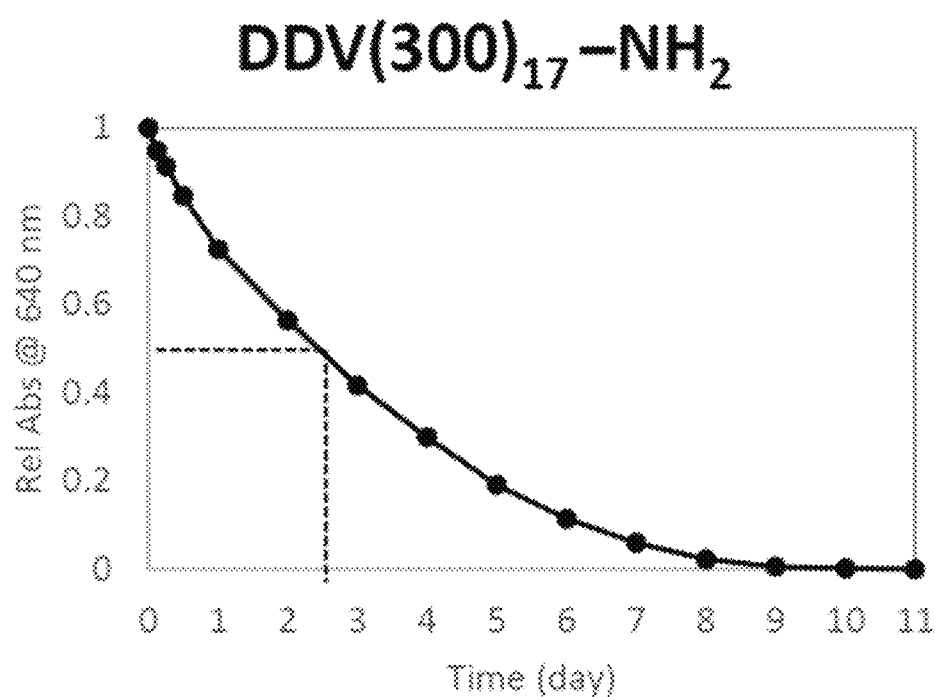
Figure 16:
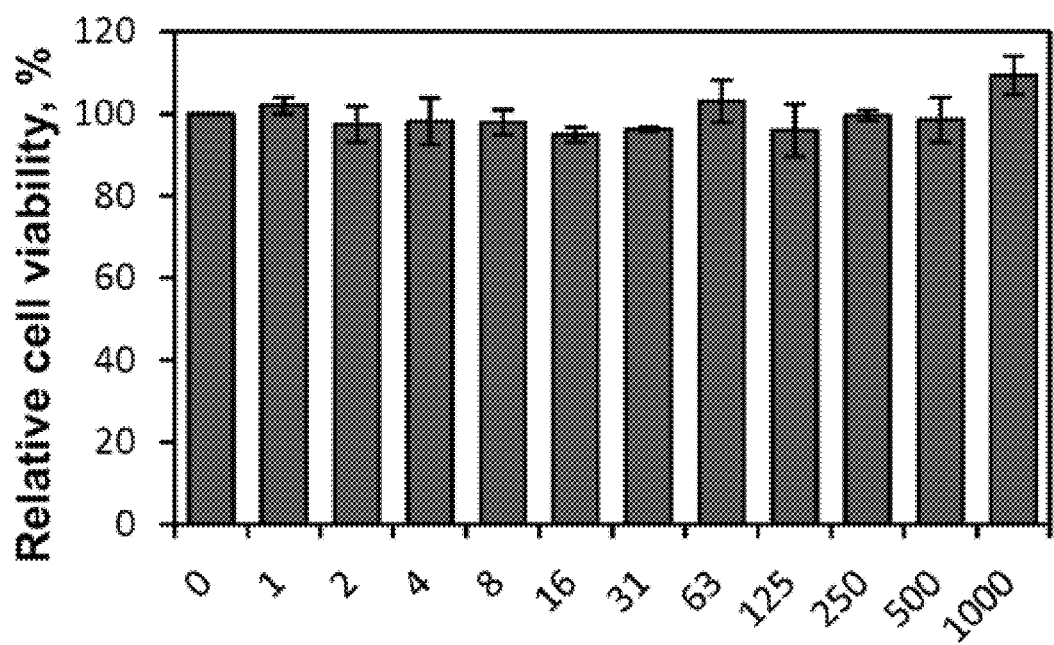
Figure 17:
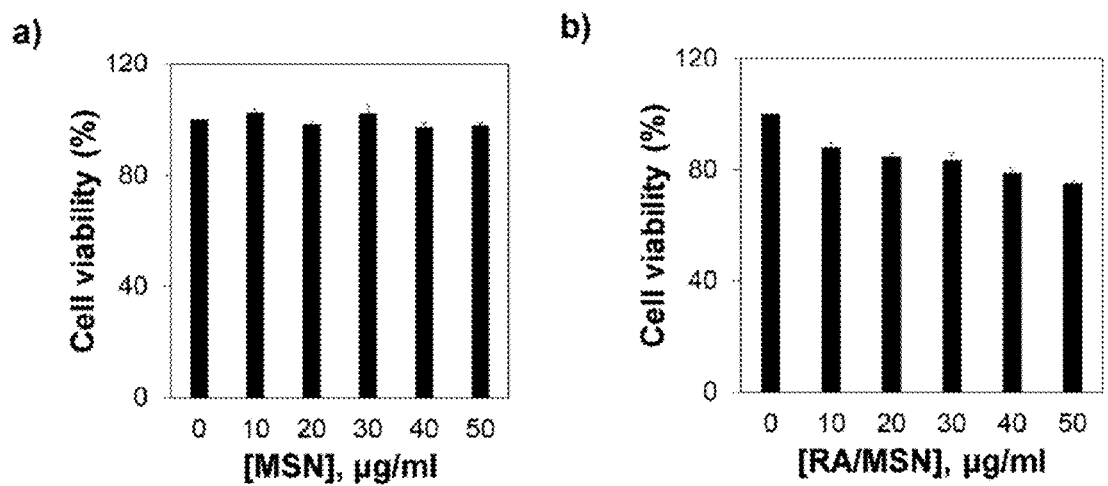
Figure 18:
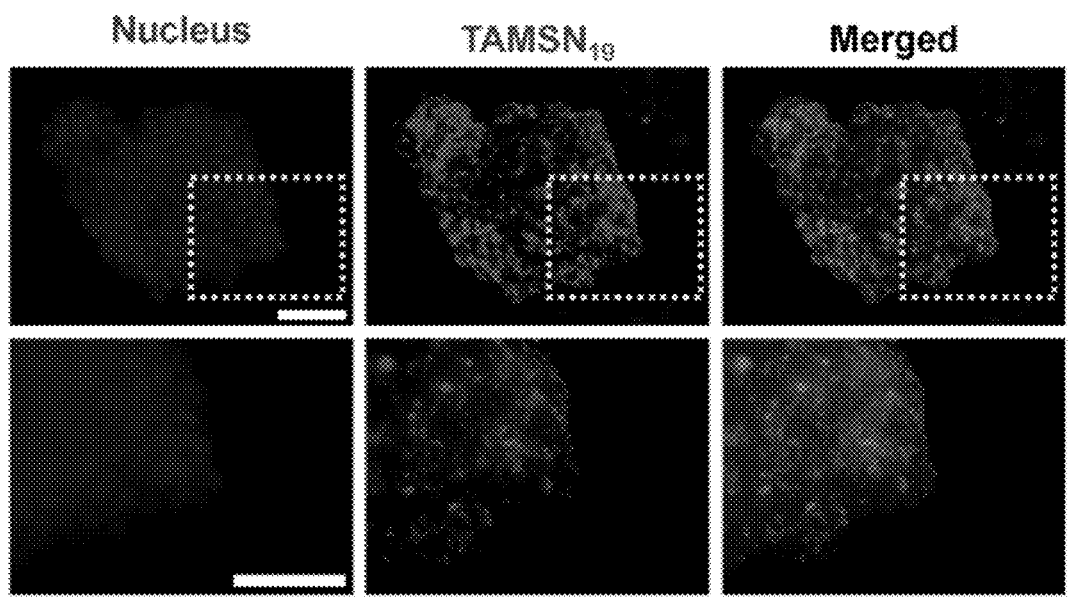
Figure 19:
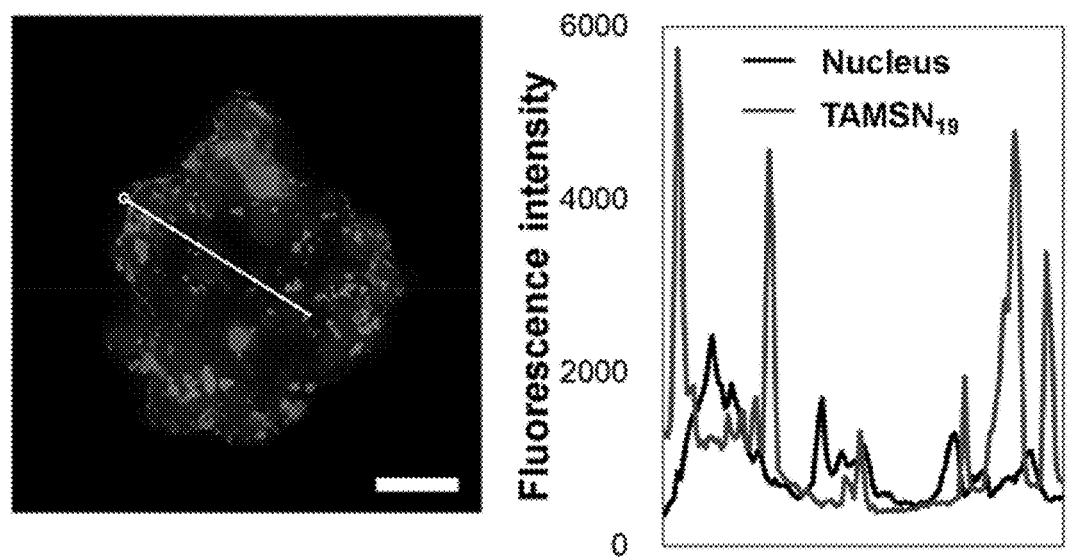
Figure 20:
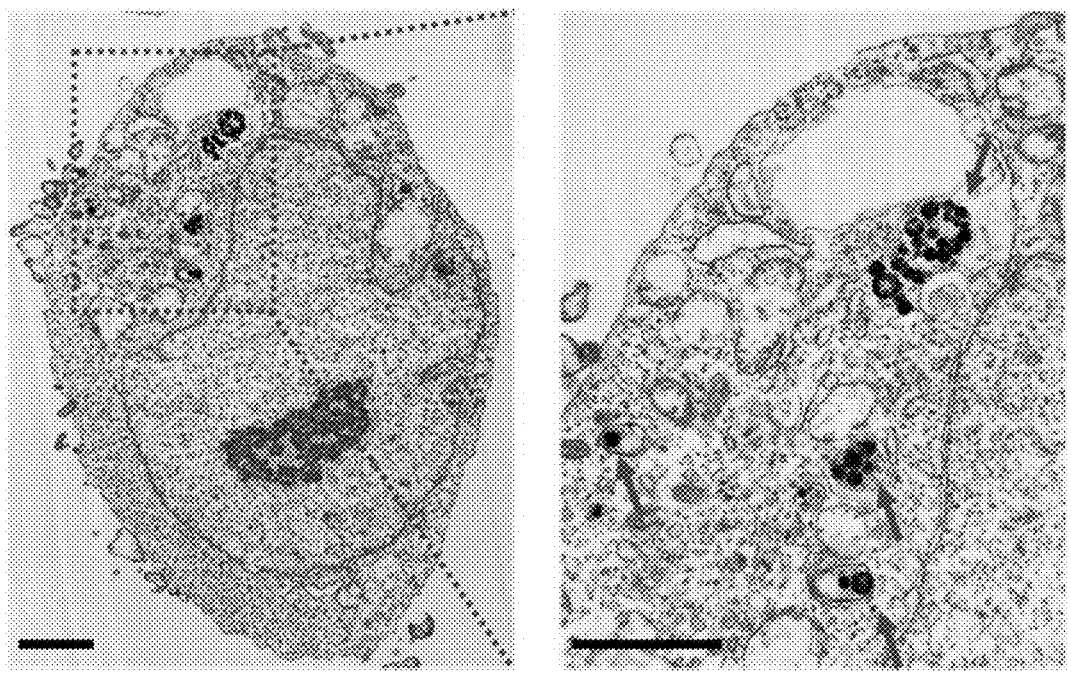
Figure 21:
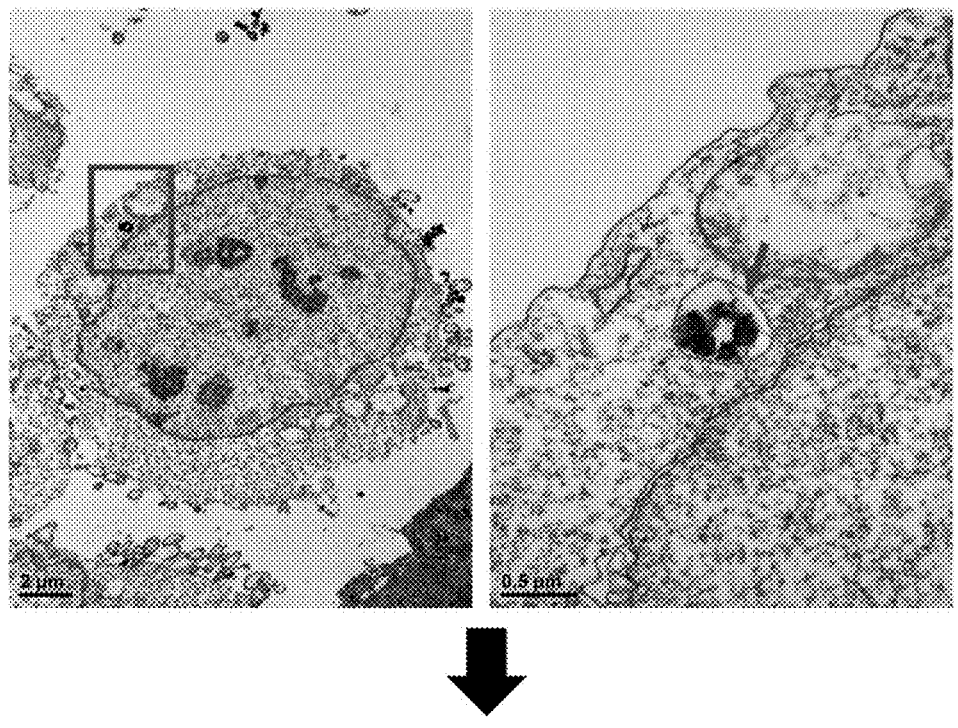
Figure 21:
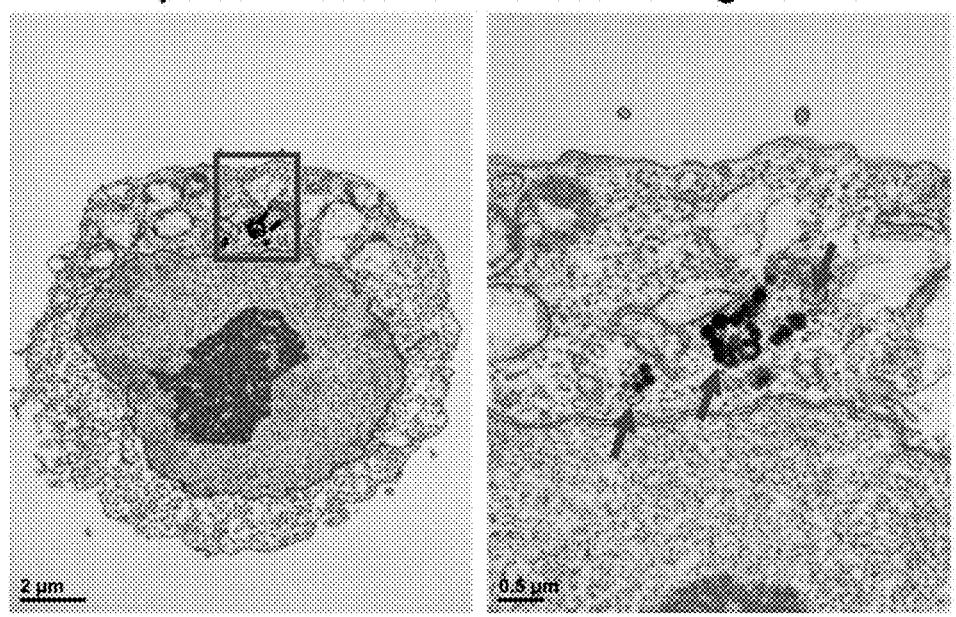
Figure 22:
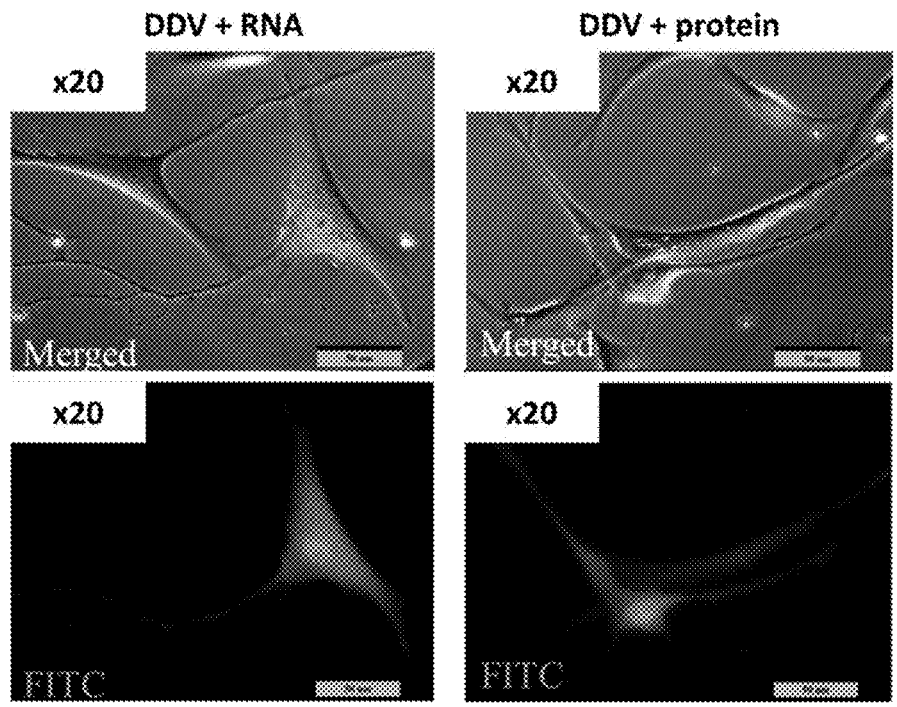
Figure 22:
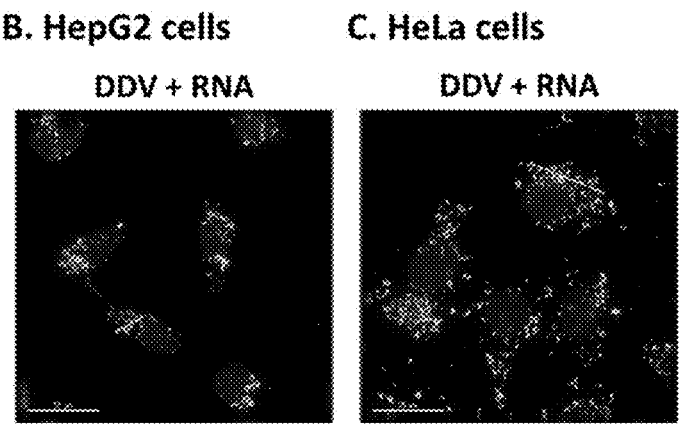
Figure 23:
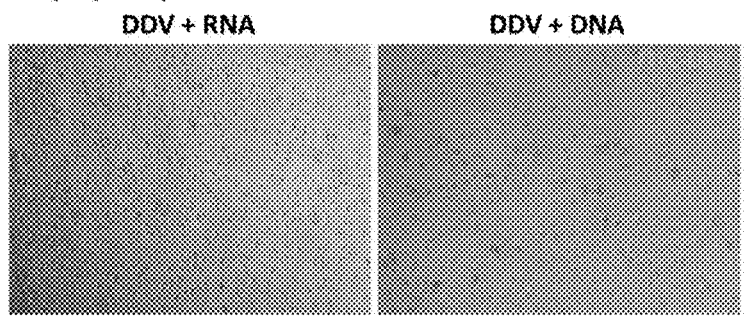
Figure 23:
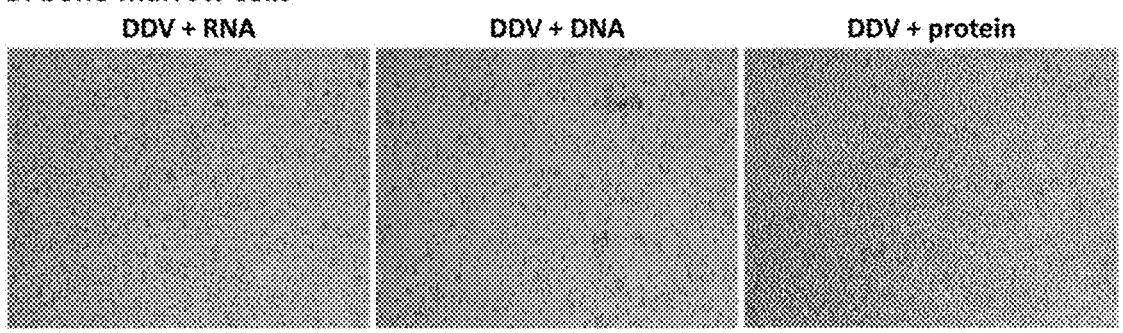
Figure 24:
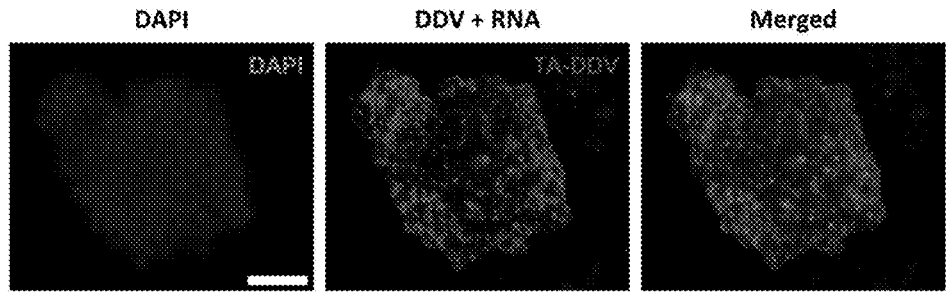
Figure 24:
Figure 25:
Figure 26:
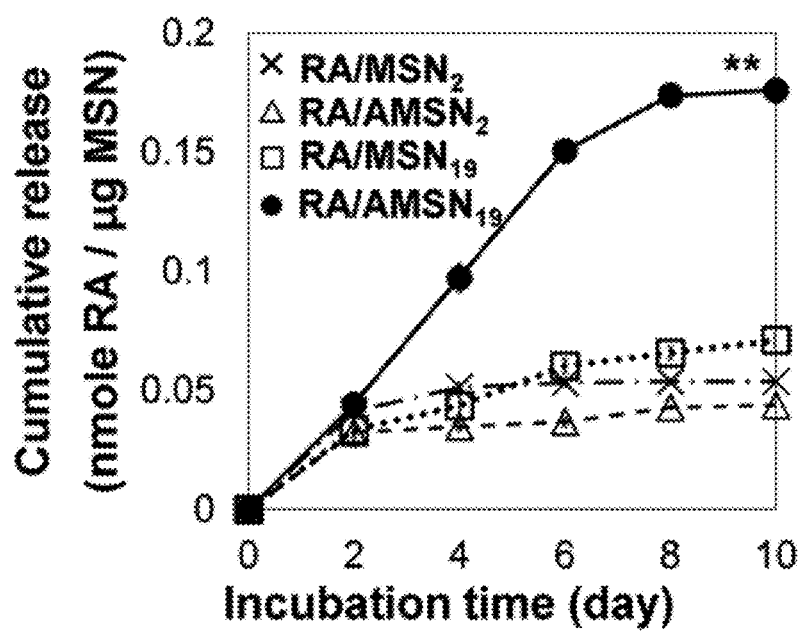
Figure 27:
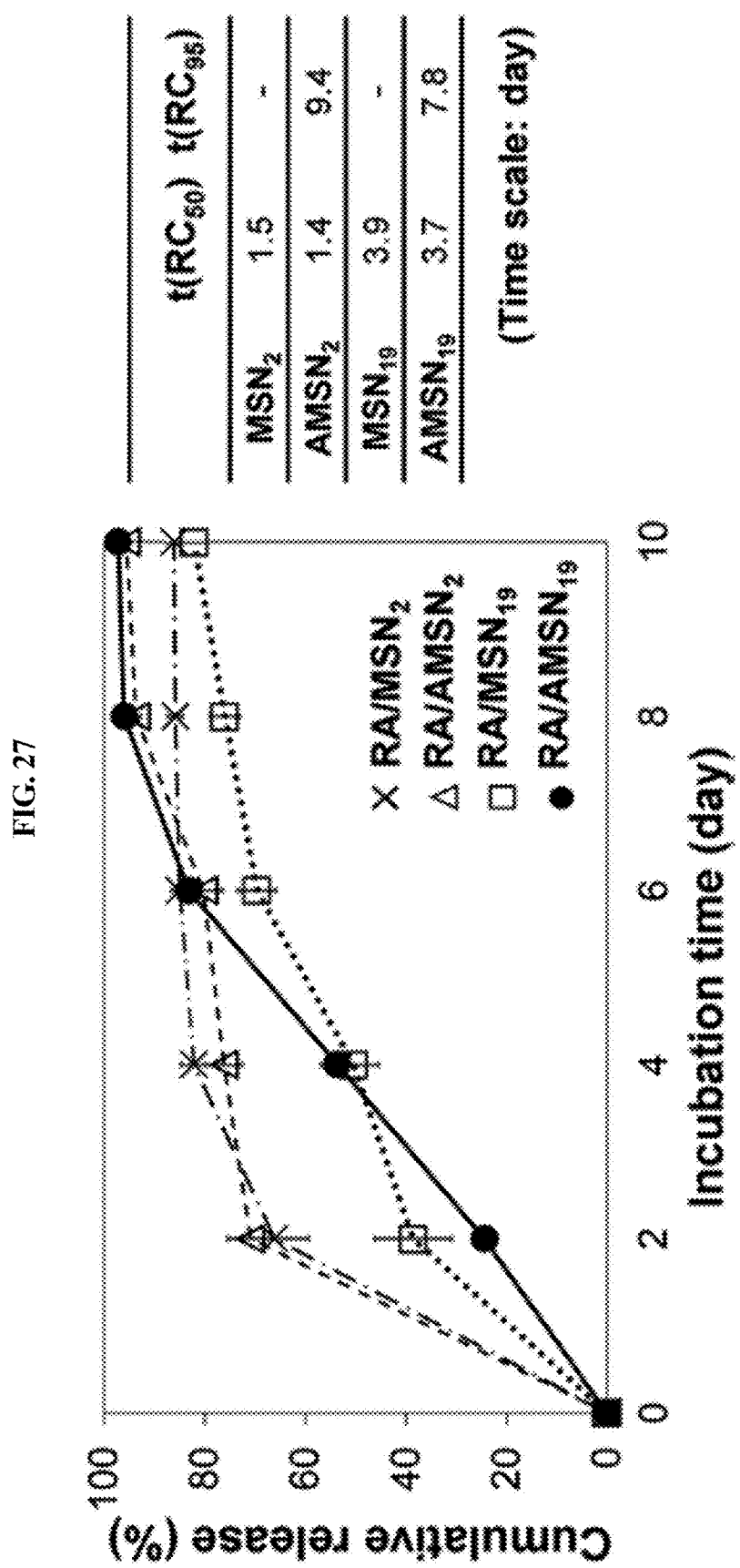

Herein, degradable delivery vehicle (DDV) refers to the particles in the examples wherein the numeral in parenthesis denotes a diameter of the particle and the subscripted numeral indicates a diameter of the pore. For instance, DDV $(200)_{10}$ means the exemplary particle having a diameter of 200 nm and a pore diameter of 10 nm;

FIGS. 7A and B illustrates UV absorption spectra of RA at various concentrations; and a standard curve of RA in terms of UV absorption peak values in the above spectrum;

FIG. 8 a graph for comparison of RA carrying amounts in relation to average pore diameter and whether there is chemical modification into an amino group or not;

FIG. 9 is microphotographs for identifying biodegradable property of the porous silica particles according to one embodiment of the present invention;

FIG. 10 illustrates a tube having a tubular permeable membrane according to an example of the present invention;

FIG. 11 is a graph illustrating results of decrease in absorbance of the porous silica particles over time according to one embodiment of the present invention;

FIG. 12 is diagrams illustrating results of decrease in absorbance of the porous silica particles for each particle diameter over time according to one embodiment of the present invention;

FIG. 13 diagrams illustrating results of decrease in absorbance of the porous silica particles for each pore diameter over time according to one embodiment of the present invention;

FIG. 14 is a graph illustrating results decrease in absorbance of the porous silica particles foe each pH value over time according to one embodiment of the present invention;

FIG. 15 is a graph illustrating results of decrease in absorbance of the porous silica particles over time according to one embodiment of the present invention;

FIG. 16 is a graph illustrating results of cell toxicity by the porous silica particles to HepG2 cells;

FIG. 17 is graphs illustrating test results of cell toxicity by the porous silica particles to mES cells;

FIG. 18 is photographs for identification of delivery of the porous silica particles into mES cells;

FIG. 19 is diagrams for identification of delivery of the porous silica particles into mES cells through fluorescence correlation analysis;

FIG. 20 is diagrams for identification of delivery of the porous silica particles into mES cells through TEM images;

FIG. 21 is diagrams illustrating that the porous silica particles are delivered into mES cells while forming endosome by endocytosis, and then, escape from the endosome and release the cell fate modulating factor carried in the particles around a nucleus;

FIG. 22 is diagrams illustrating results of identifying the delivery of the porous silica particles into human fibroblasts, HepG2 cells and HeLa cells, respectively;

FIG. 23 is diagrams illustrating results of identifying the delivery of the porous silica particles into lymphocyte and myelocytes, respectively;

FIG. 24 is photographs illustrating results of identifying the delivery of the porous silica particles into human embryonic stem cells and neural progenitor cells, respectively;

FIG. 25 is diagrams illustrating results result of delivery of porous silica particles having fluorescein-labelled with FITC by directly injecting the same in vivo to the spinal cord of a rat;

FIG. 26 is a graph illustrating RA release amounts carried in each porous silica particle according to incubation time;

FIG. 27 is diagrams illustrating RA release rates in wt. % carried in each porous silica particle according to incubation time.

Figure 28:
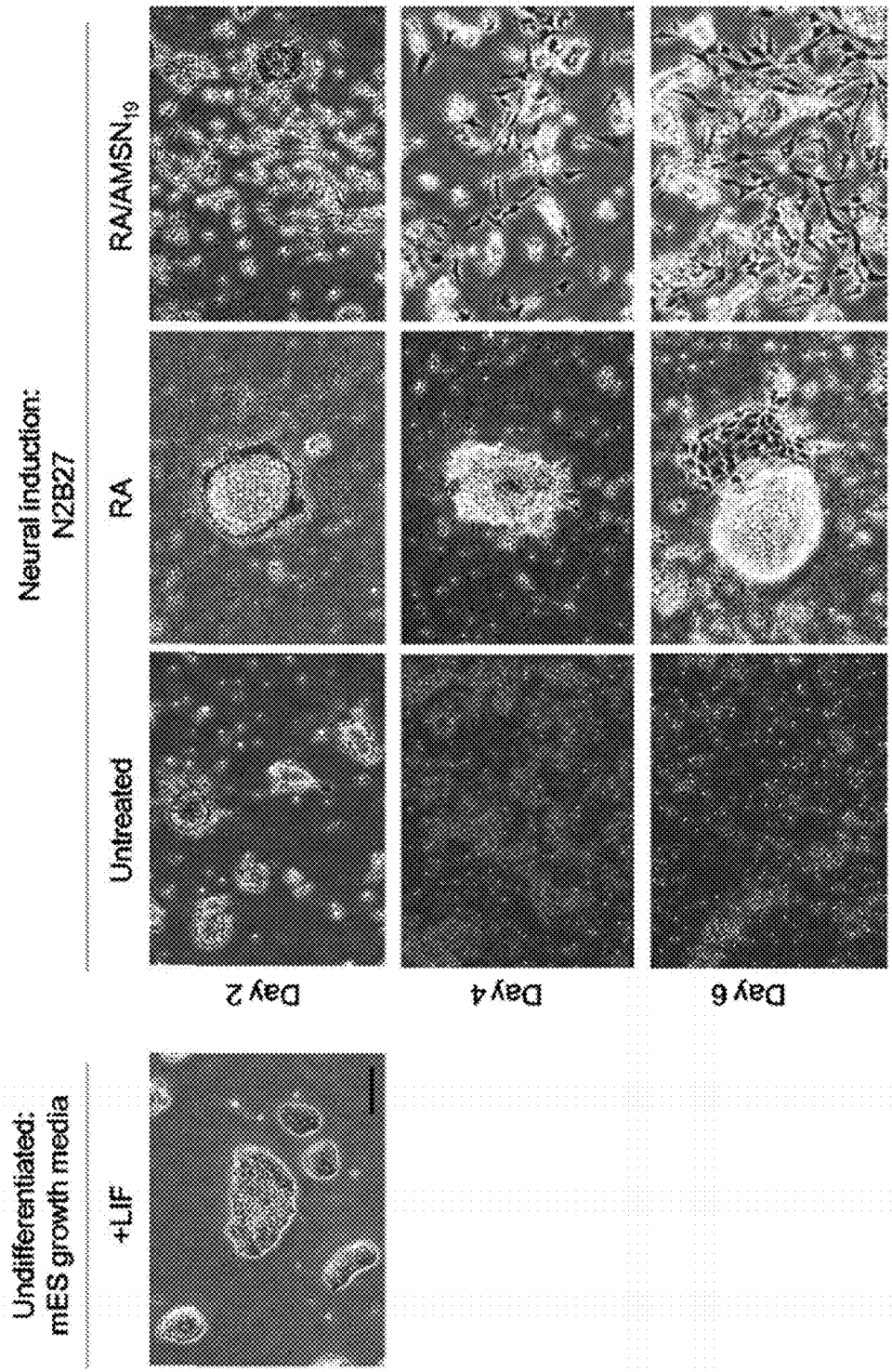
Figure 29:
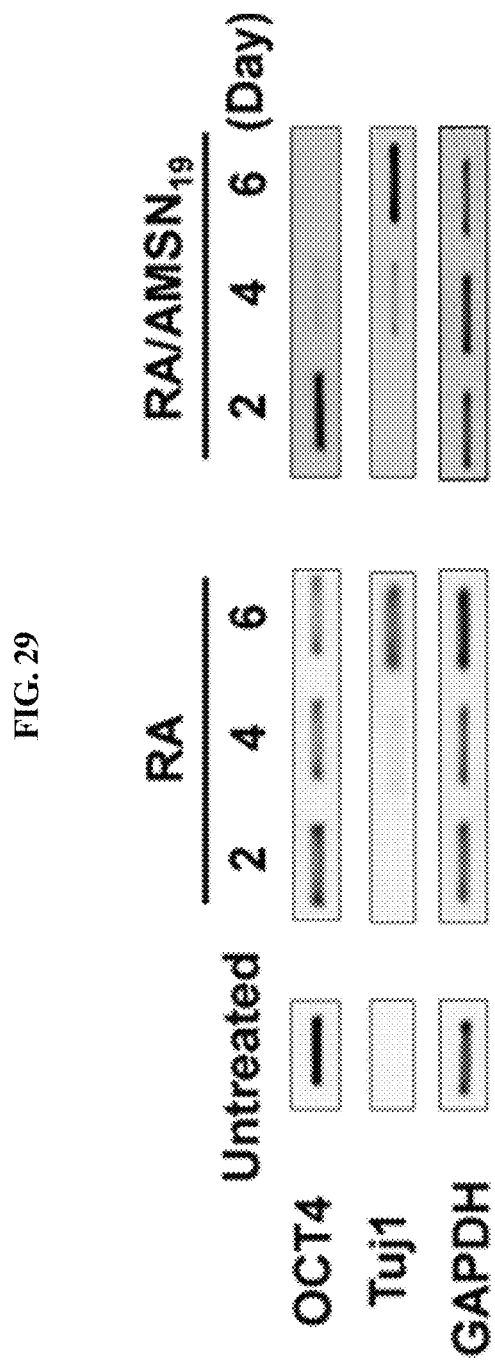
Figure 30:
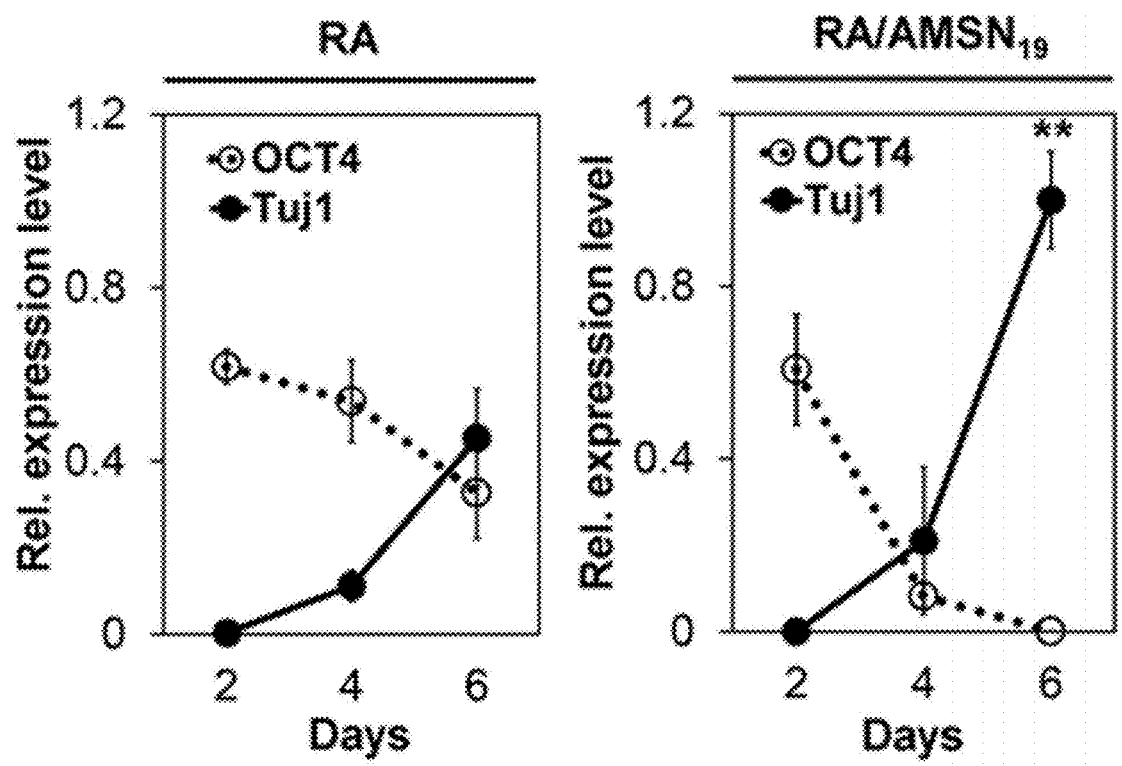
Figure 31:
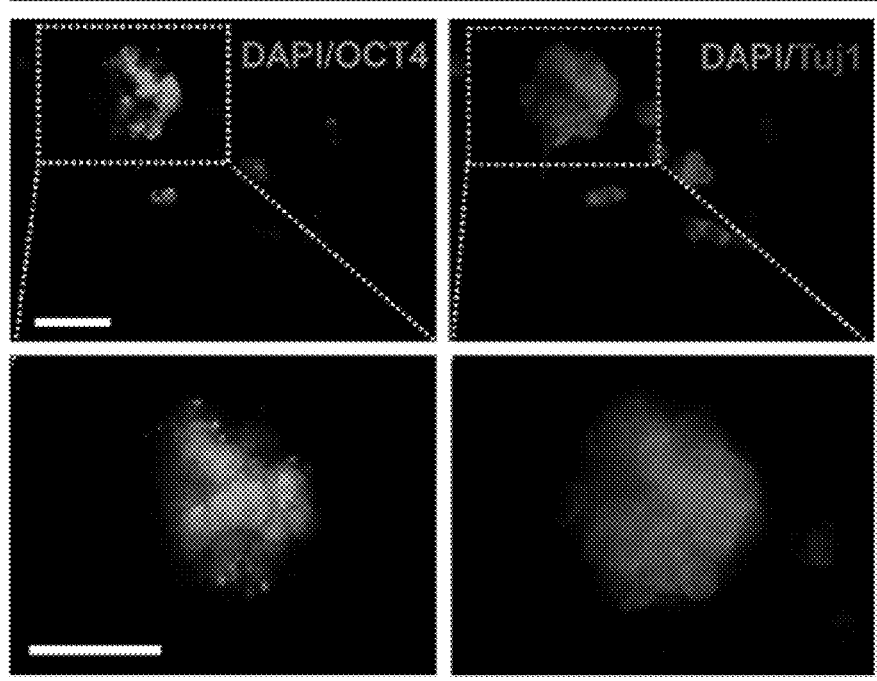
Figure 31:
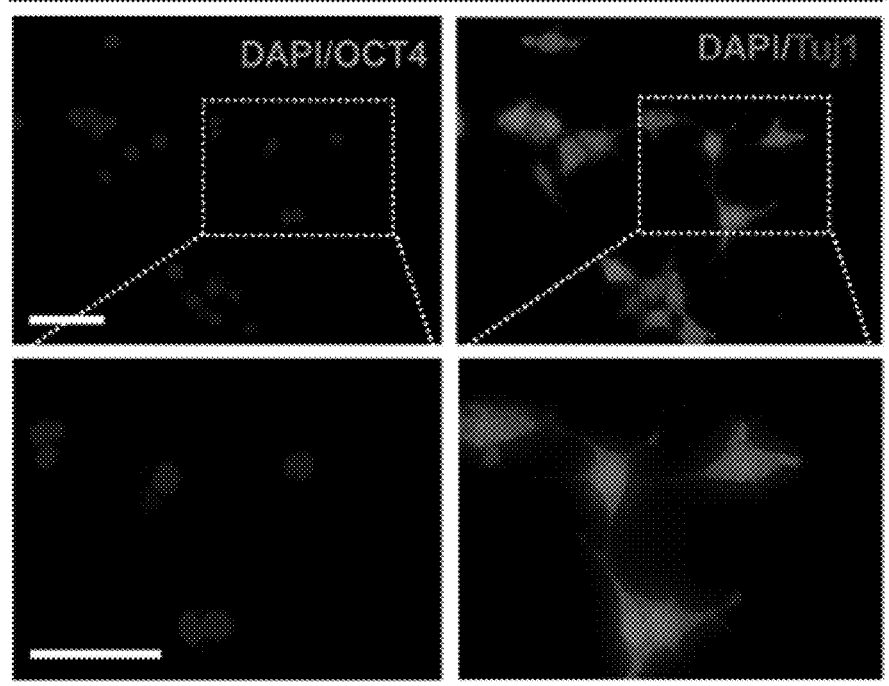
Figure 32:
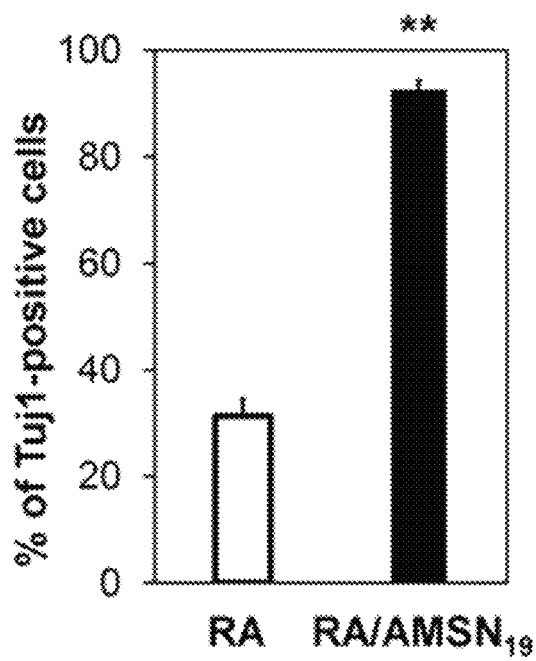
Figure 33:
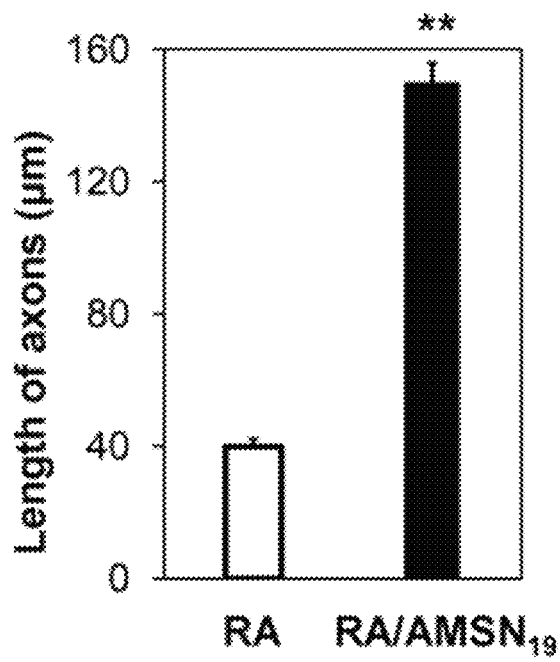
Figure 34:
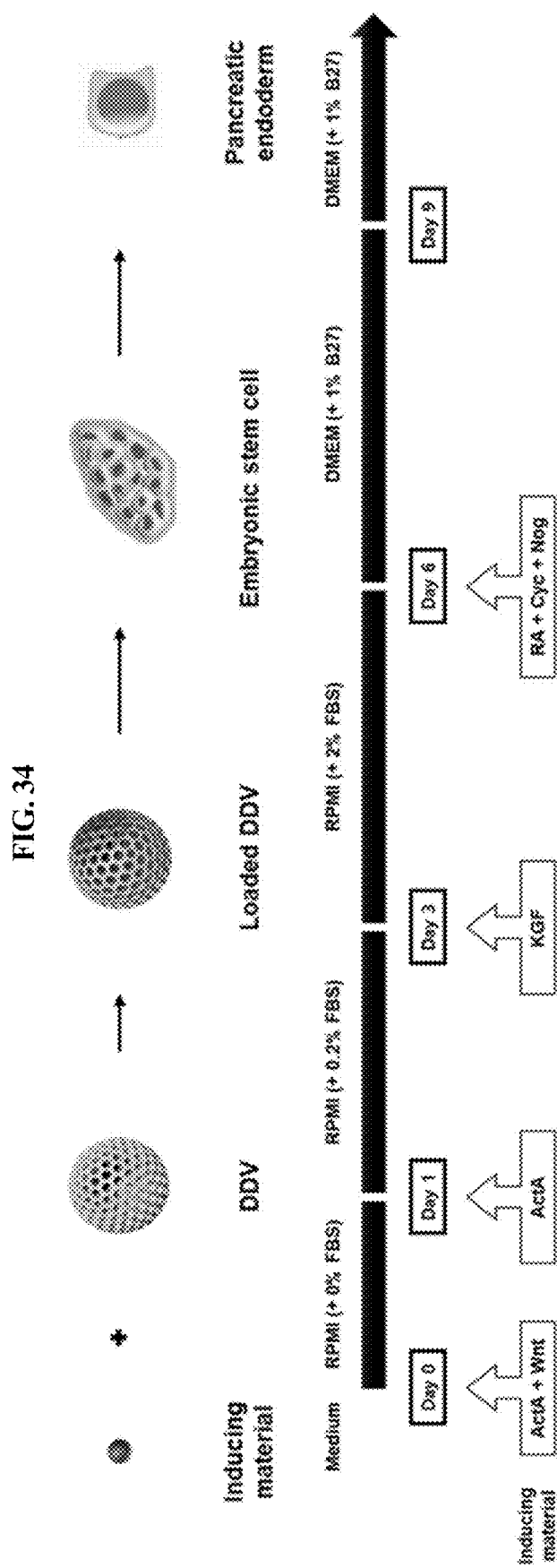
Figure 35:
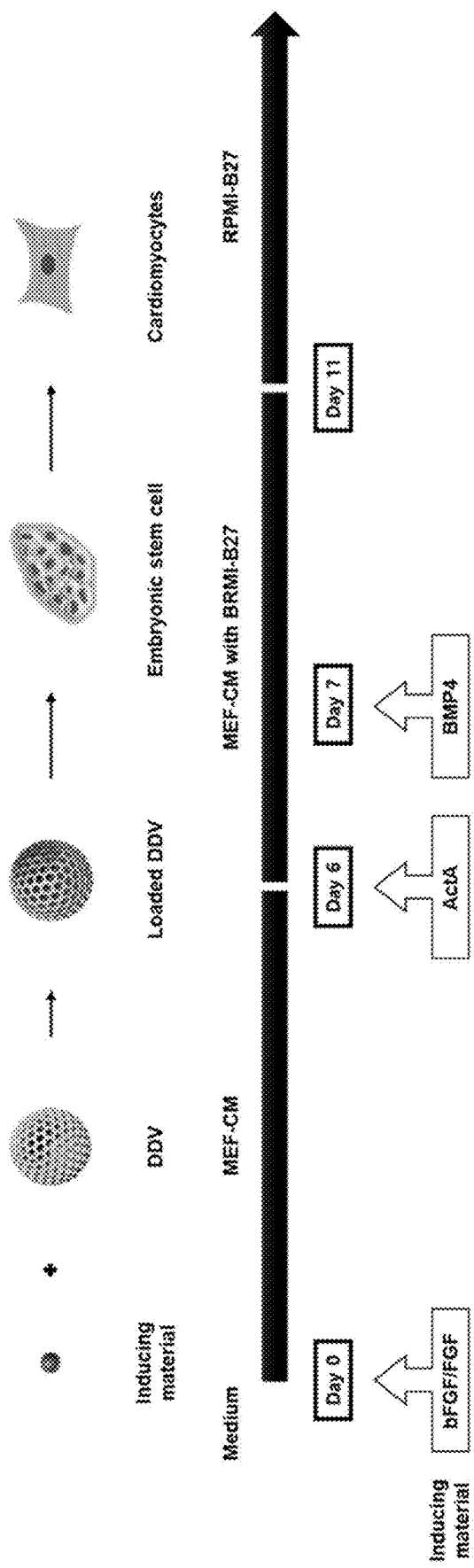
Figure 36:
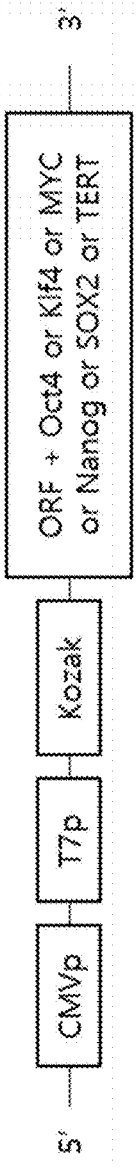
Figure 37:
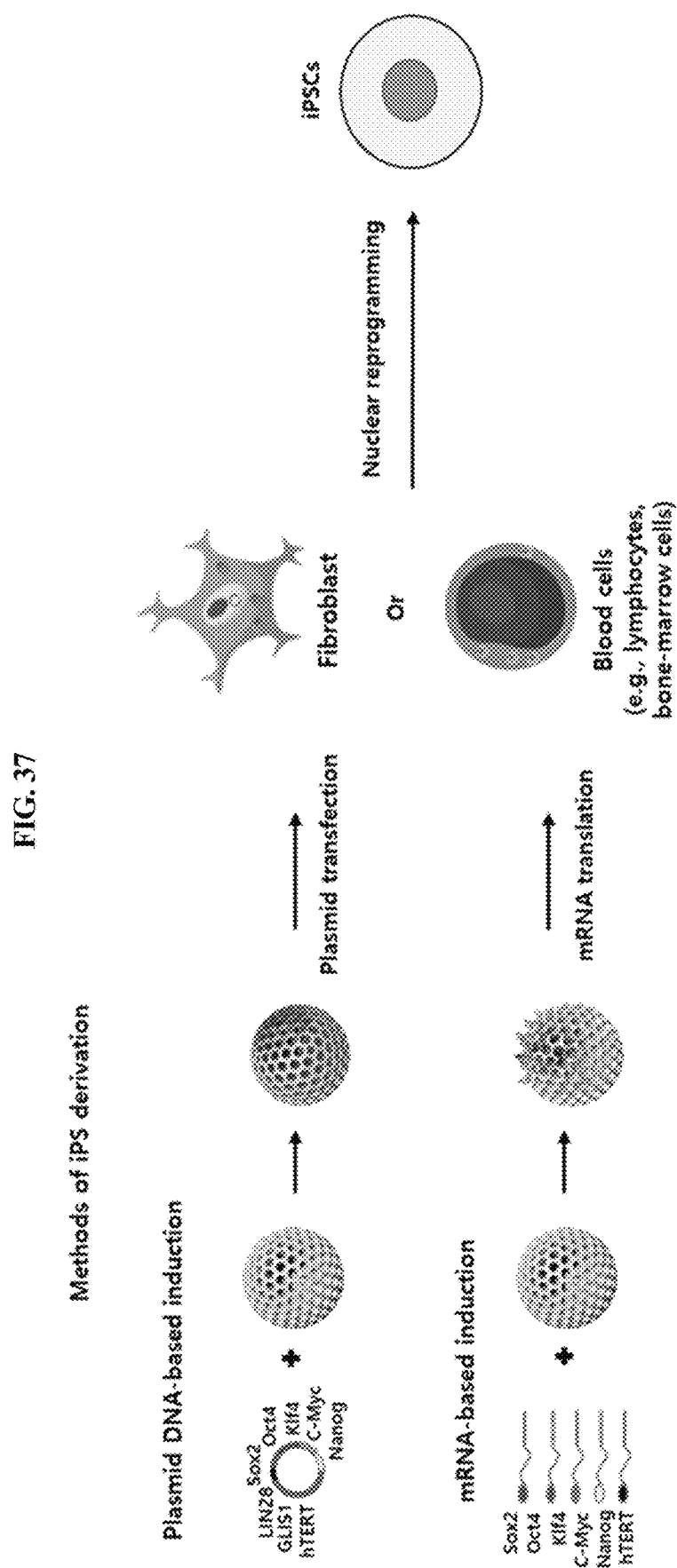
Figure 38:
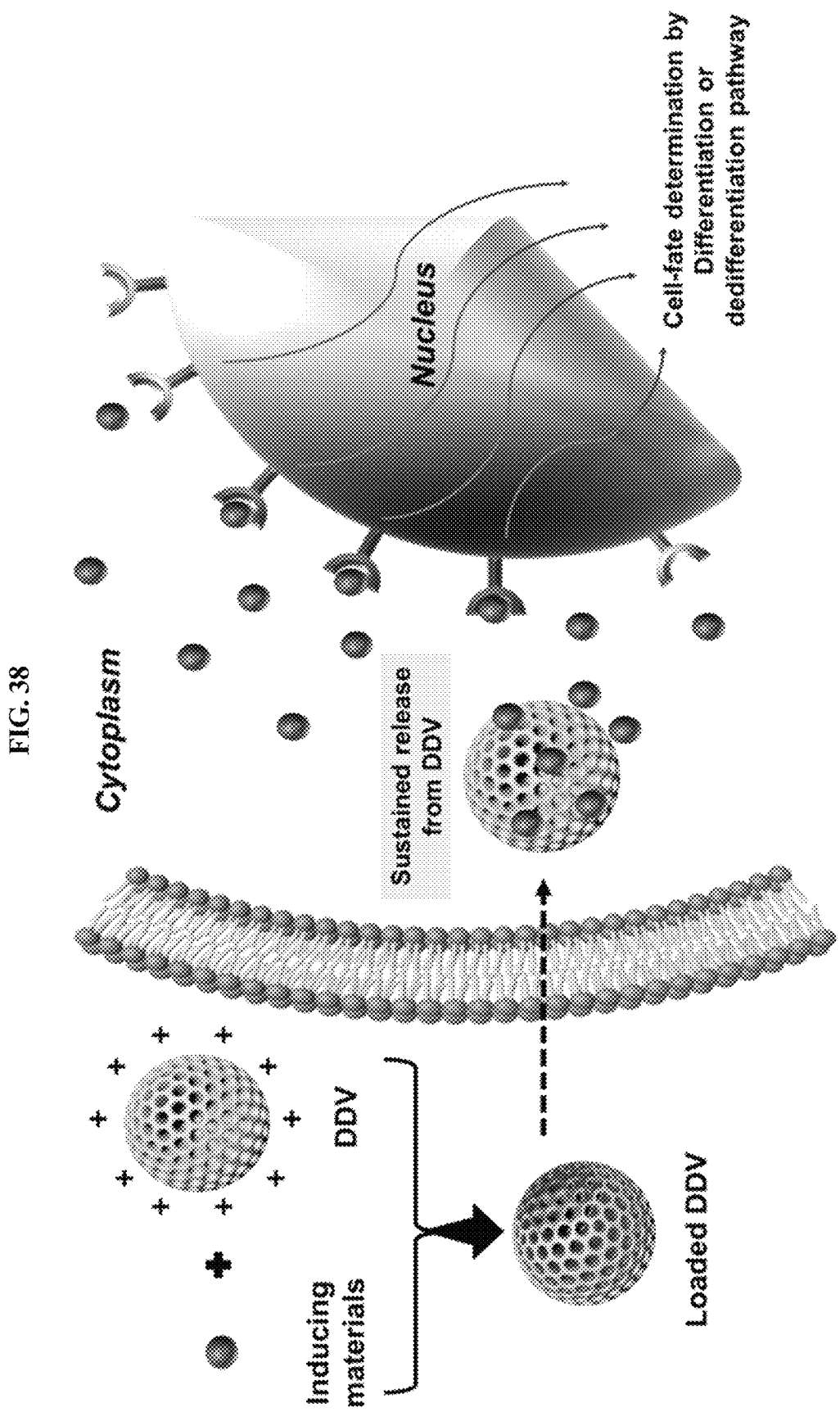

FIG. 28 is diagrams illustrating extents of neuron differentiation in an untreated group, a RA singular treatment group and a RA/AMSN$_{19}$ treatment group, respectively, in regard to differentiation from mES to nerve cells;

FIG. 29 is a diagram illustrating mRNA expression levels by OCT4 and Tuj1 marker gene in the untreated group, the RA singular treatment group and the RA/AMSN$_{19}$ treatment group, respectively, in regard to differentiation from mES to nerve cells;

FIG. 30 is graphs illustrating relative expression levels by OCT4 and Tuj1 marker gene in the RA singular treatment group and the RA/AMSN$_{19}$ treatment group, respectively, in regard to differentiation from mES to nerve cells;

FIG. 31 is photographs illustrating chemical analysis results of immunocytes in the RA singular treatment group and the RA/AMSN$_{19}$ treatment group, respectively, in regard to differentiation from mES to nerve cells;

FIG. 32 is a graph illustrating the number of Tuj-1 positive cells in % relative to total cells of the RA singular treatment group and the RA/AMSN$_{19}$ treatment group, respectively, in regard to differentiation from mES to nerve cells;

FIG. 33 is a graph illustrating lengths of axons compared between the RA singular treatment group and the RA/AMSN$_{19}$ treatment group, in regard to differentiation from mES to nerve cells;

FIG. 34 is a diagram schematically illustrating a process of differentiating embryonic stem cells into pancreatic endoderm cells by using the composition according to the present invention;

FIG. 35 is a diagram schematically illustrating a process of differentiating embryonic stem cells into cardiomyocytes by using the composition according to the present invention;

FIG. 36 is a block diagram illustrating a pDNA design used in reverse-differentiation of fibroblasts or blood cells into induced multipotent stem cells by using the composition according to the present invention;

FIG. 37 is a diagram schematically illustrating a process of reverse-differentiation of fibroblasts or blood cells into induced multipotent stem cells by using the composition according to the present invention; and FIG. 38 is a diagram schematically illustrating a method for modulating cell fate by using the composition according to the present invention.

DETAILED DESCRIPTION

Hereinafter, the present invention will be described in detail.

The present invention provides a composition for modulating cell fate, including: porous silica particles which carry a cell fate modulating factor on a surface of the particle or inside pores of the particle, and have t of 20 or more, at which a ratio of absorbance in Mathematical Equation 1 below reaches ½, wherein the surface of the particle or the inside the pores of the particle has been chemically modified.

$$A_t/A_0$$ [Mathematical Equation 1]

(wherein $A_0$ is an absorbance of the porous silica particles measured when 5 ml of suspension containing 1 mg/ml of porous silica particles is fed to a tubular permeable membrane having 50 kDa pores; 15 ml of a solvent substantially the same as the suspension is placed outside the permeable membrane while contacting the same; the inside/outside of the permeable membrane are under horizontal agitation with 60 rpm at 37° C.; and $A_t$ is another absorbance of the porous silica particles measured t time after the measurement of $A_0$.)

With regard to the composition of the present invention, the cell fate modulating factor may include a material which is carried in a porous silica particle and delivered to any cell, so as to exhibit activities, for example, leading the cell in an undifferentiated state to differentiated state, modulating a differentiation state, induce reverse-differentiation of the cell in differentiated state into the same in an undifferentiated state, inducting direct differentiation of a specific differentiated cell into another specific differentiated cell.

The cell fate modulating factor may include at least one low molecular weight compound selected from the group consisting of 3-isobutyl-1-methylxanthine, CHIR, KY02111, DZNep, tranylcypromine, LDN, digoxin, nicotinamide, IWP2, IWP4, XAV939, TTNPB, PD0325901, A83-01, hiazovivin, DMH1, rosiglitazone, SB-431542, pifithrin-alpha, FSK (Forskolin), IDE1, IDE2, DAPT, CYC (cyclopamine-KAAD), PDBu, Retinoic acid, ascorbic acid, dexamethasone, 5-azacytidine, taurine, Kartogenin, ursolic acid, SR1555, halofunginone, CHIR99021 and valproic acid, but it is not limited thereto.

The cell fate modulating factor may also include at least one bio-molecule selected from the group consisting of Dkk1 (Dickkopf Like Acrosomal Protein 1), Lefty A (left-right determination factors), activin A, GATA4, Foxa1, Foxa2, Mef2c, BMPs, IGF, HGF, WNT, FGF, KGF, bFGF, Klf4, CRX, RAX, OTX2, Ascl1, NFIA, NFIB, Fezf2, Hmga2, VEGF, LIF, TGF-β, SOX2, Noggin, nodal, Bm2, Mytl1, NeuroD1, Hnf1a, Foxa3, Tbx5, Tymosin beta4, Tbx5, EGF, SOXs, Bestrophin1, Ctip2, NeuroG2, Atf5, Prox1, Hnf4a, OCT4, TERT, c-myc, insulin, FGF9 and interleukin, but it is not limited thereto.

The cell fate modulating factor may also include oligonucleotides selected from the group consisting of plasmid DNA or linear DNA, which contains a gene encoding the above bio-molecule, and transcriptomes thereof such as mRNA, miRNA (miR-124, miR-9, miR9*, miR-302, miR-367, and miR-21, etc.), siRNA and modified products thereof, but it is not limited thereto.

With regard to the composition of the present invention, the porous silica particle refers to a silica nanostructure containing fine pores with a size ranging from several nanometers to several micrometers, wherein regularity in alignment of pores is well defined and properties of the material (i.e., pore size, specific surface area, and surface characteristic, etc.) are adjustable to fit in use environments.

With regard to the composition of the present invention, the porous silica particles (MSN or DDV) may have a siloxane group (Si—O—Si), which could be formed by dehydration between silanol groups (Si—OH) on the surface of the silica particle or inside pores of the particle. In such a case, compared to particles having silanol groups only, the particle having a siloxane group may involve structural shrinkage of particles to result in structural densification of the particles, reduce self-degradation rates of the particles, and achieve effects of sustained and continuous release of the carried cell fate modulating factor. The siloxane group may be formed by a calcination process described below, but it is not particularly limited thereto.

With regard to the composition of the present invention, the surface of the porous silica particle and/or the inside the pores of the particle may be modified. Herein, the modification may refer to substitution of —OH functional group in the silanol group (Si—OH) contained in the silica particle with another functional group. Depending upon types of such modified functional group and extents of the modification, types of the cell fate modulating factor suitable for carrying in the particle may be varied. Further, a release rate of the cell fate modulating factor may be controlled by adjusting interaction of the porous silica particles to an environment for releasing the cell fate modulating factor, thus to control the self-degradation rate of the particles. Further, release of the cell fate modulating factor due to diffusion of the same from the particles may controlled by adjusting a binding force of the cell fate modulating factor to the porous silica particles.

With regard to such modification as described above, a chemical or biological modification method may be adopted, but it is not limited thereto. That is, any conventional method well-known in the related art may be used. However, in consideration of substitution of functional groups through a covalent bond to the silica particles, it is preferable to use a chemical modification method. Further, the surface of the particle and the inside the pores of the particle may be modified in the same manner as or different manners from each other.

The modification may be conducted by reacting a compound having hydrophilic, hydrophobic, cationic or anionic substituents, which are intended to be introduced, with the particles, but it is not limited thereto. That is, the modification may also be conducted by reacting a compound which carries the cell fate modulating factor, moves the cell fate modulating factor toward a target cell or carries a material for other purposes, or a compound which has a substituent for binding additional substituents, with the particles. In this case, the substituent may be in a form of further including an antibody, a ligand, a cell-permeable peptide, an aptamer or the like.

The above compound may be, for example, alkoxysilane having $C_1$ to $C_{10}$ alkoxy group, but it is not limited thereto. The alkoxylsilane may have at least one alkoxyl group, for example, 1 to 3 alkoxy groups and may have a substituent intended to be introduced or another substituent substituted with the above substituent at a site to which the alkoxy group is not bonded.

Reacting the alkoxysilane with the porous silica particles may form a covalent bond between a silicon atom and an oxygen atom, thus to allow the alkoxysilane to be linked to the surface of the porous silica particle or the inside pores of the particle. Further, since the alkoxysilane has a substituent to be introduced, the substituent may be introduced on the surface of the porous silica particle or inside the pores of the particle.

The above reaction may be performed by reacting porous silica particles dispersed in a solvent with alkoxysilane, wherein the solvent used may be water and/or an organic solvent. This organic solvent may include, for example: ethers (in particular, cyclic ethers) such as 1,4-dioxane, etc.; halogenated hydrocarbons such as chloroform, methyl chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methyl isobutylketone, γ-butyrolactone, 1,3-dimethyl-imidazolinone, methylethylketone, cyclohexanone, cyclopentanone, 4-hydroxy-4-methyl-2-pentanone, etc.; aromatic hydrocarbons such as benzene, toluene, xylene, tetramethyl benzene, etc.; alkylamides such as N,N-dimethylformamide, N,N-dibutylformamide, N,N-dimethyl acetamide, N-methyl pyrrolidone, etc.; alcohols such as methanol, ethanol, propanol, butanol, etc.; glycol ethers (cellosolve) such as ethyleneglycol monoethylether, ethyleneglycol monomethylether, ethyleneglycol monobutylether, diethyleneglycol monoethylether, diethyleneglycol monomethylether, diethyleneglycol monobutylether, propyleneglycol monomethylether, propyleneglycol monoethylether, dipropyleneglycol diethylether, triethyleneglycol monoethylether, etc.; other compounds including, for example, methyl acetamide (DMAc), N,N-diethyl acetamide, dimethyl formamide (DMF), diethyl formamide (DEF), N,N-dimethyl acetamide (DMAc), N-methyl pyrrolidone (NMP), N-ethyl pyrrolidone (NEP), 1,3-dimethyl-2-imidazolidinone, N,N-dimethylmethoxy acetamide, dimethyl sulfoxide, pyridine, dimethylsulfone, hexamethyl phosphoamide, tetramethylurea, N-methyl caprolactam, tetrahydrofuran, m-dioxane, P-dioxane, 1,2-dimethoxyethane, or the like, in particular, toluene may be used, but it is not limited thereto.

The reaction of the particles with alkoxysilane may be conducted, for example, under heating. In this case, the heating may be conducted, for example, at 80° C. to 180° C. For instance, the reaction may be conducted at 80° C. to 160° C., 80° C. to 150° C., 100° C. to 160° C., 100° C. to 150° C., 110° C. to 150° C., or the like within the above range, but it is not limited thereto.

Further, the reaction of the particle with alkoxysilane may be conducted, for example, for 4 to 20 hours. For instance, the reaction may be conducted for 4 to 18 hours, 4 to 16 hours, 6 to 18 hours, 6 to 16 hours, 8 to 18 hours, 8 to 16 hours, 8 to 14 hours, 10 to 14 hours, or the like within the above range, but it is not limited thereto.

With regard to the modification described above, modification into a cationic substituent may be for loading positive charge on the particle or carrying an anionic cell fate modulating factor. For instance, the modification may be conducted by reacting the particles with alkoxysilane having a basic group, i.e., a nitrogen containing group such as amino or aminoalkyl. More particularly, N-[3-(Trimethoxysilyl)propyl]ethylenediamine, N1-(3-Trimethoxysilylpropyl)diethylenetriamine, (3-Aminopropyl)trimethoxysilane, N-[3-(Trimethoxysilyl)propyl]aniline, Trimethoxy[3-(methylamino)propyl]silane, 3-(2-Aminoethylamino)propyldimethoxymethylsilane, and the like may be used, but it is not limited thereto.

With regard to the modification described above, modification into an anionic substituent may be for loading negative charge on the particle or carrying a cationic cell fate modulating factor. For instance, the modification may be conducted by reacting the particles with alkoxysilane having an acidic group such as carboxyl, sufonic acid, thiol or the like. More particularly, (3-Mercaptopropyl) trimethoxysilane, and the like may be used, but it is not limited thereto.

With regard to the modification described above, modification into a hydrophilic substituent may have advantages in aspects of use of the inventive composition and formation thereof. For instance, the above advantages may be achieved by reacting the particles with alkoxysilane having a functional group such as carboxyl, amino, carbonyl, sulfhydryl, phosphate, thiol, ammonium, ester, imide, thioamide, keto, ether, indene, sulfonyl, polyethyleneglycol or the like. More particularly, N-[3-(Trimethoxysilyl)propyl]ethylenediamine, N1-(3-Trimethoxysilylpropyl)diethylenetriamine, (3-Aminopropyl)trimethoxysilane, (3-Mercaptopropyl) trimethoxysilane, Trimethoxy[3-(methylamino)propyl]silane, 3-(2-Aminoethylamino)propyldimethoxymethylsilane, and the like may be used, but it is not limited thereto.

With regard to the modification described above, modification into a hydrophobic substituent may have an advantage of improving a binding force of the particles to an insoluble (hydrophobic) cell fate modulating factor. For instance, the modification may be conducted by reacting the particles with alkoxysilane having a functional group such as substituted or non-substituted $C_1$ to $C_{30}$ alkyl, substituted or non-substituted $C_3$ to $C_{30}$ cycloalkyl, substituted or non-substituted $C_6$ to $C_{30}$ aryl, substituted or non-substituted $C_2$ to $C_{30}$ heteroaryl, halogen, $C_1$ to $C_{30}$ ester or a halogen-containing group. More particularly, Trimethoxy(octadecyl)silane, Trimethoxy-n-octylsilane, Trimethoxy(propyl)silane, Isobutyl(trimethoxy)silane, Trimethoxy(7-octen-1-yl)silane, Trimethoxy(3,3,3-trifluoropropyl)silane, Trimethoxy(2-phenylethyl)silane, Vinyltrimethoxysilane, Cyanomethyl, 3-(trimethoxysilyl)propyl] trithiocarbonate, (3-Bromopropyl)trimethoxysilane, and the like may be used, but it is not limited thereto.

The modification may be conducted in a combination mode. For instance, surface modification may be conducted twice or more on an external surface of the particle or inside the pores of the particle. In a particular example, the positively charged particle may be changed to have different surface characteristics by binding a compound containing a carboxyl group to silica particles having an amino group introduced therein via an amide bond, but it is not limited thereto.

With regard to the modification described above, a reaction temperature, a reaction time, an amount of the compound used for modification, etc. may be properly selected in consideration of degree of modification. More particularly, under different reaction conditions based on hydrophilicity, hydrophobicity and/or a charge level of the cell fate modulating factor, hydrophilicity, hydrophobicity and/or the charge level of the porous silica particles may be adjusted, thereby controlling a release rate of the cell fate modulating factor. For instance, once the cell fate modulating factor is highly negatively charged at neutral pH, the reaction temperature or the reaction time may be increased or an amount of the compound treated may be increased in order for the porous silica particle to be highly positively charged, but it is not limited thereto.

According to the composition of the present invention, the porous silica particles may be biodegradable particles, and when these particles carry the cell fate modulating factor therein and are administered in the body, may release the cell fate modulating factor while being biodegraded in vivo. Therefore, the particles are slowly released in the body, thus to give sustained release property to the carried cell fate modulating factor. For instance, t may be 20 or more at which a ratio of absorbance in Mathematical Equation 1 below reaches ½.

$$A_t/A_0$$ [Mathematical Equation 1]

(wherein $A_0$ is an absorbance of the porous silica particles measured when 5 ml of suspension containing 1 mg/ml of porous silica particles is fed to a tubular permeable membrane having 50 kDa pores; 15 ml of a solvent substantially the same as the suspension is placed outside the permeable membrane while contacting the same; the inside/outside of the permeable membrane are under horizontal agitation with 60 rpm at 37° C.; the suspension has pH 7.4; and $A_t$ is another absorbance of the porous silica particles measured t time after the measurement of $A_0$.)

Mathematical Equation 1 above represents a degradation rate at which the porous silica particles are biodegraded under conditions similar to the inside of the body. The absorbances $A_0$ and $A_t$ may be measured by, for example, putting the porous silica particles and the suspension into a tubular permeable membrane while adding the same suspension to the outside of the permeable membrane.

The suspension may include a buffer solution, in particular, at least one selected from the group consisting of phosphate buffered saline (PBS) and simulated body fluid (SFB) and, more preferably, PBS.

The particle is biodegradable and may be slowly degraded in the suspension, wherein the diameter of 50 kDa corresponds to about 5 nm and is able to pass a permeable membrane having the 50 kDa diameter. The tubular permeable membrane is under horizontal agitation with 60 rpm so that the suspension may be uniformly blended while the degraded particles may be discharged outside the permeable membrane.

In Mathematical Equation 1 above, the absorbance may be measured, for example, under an environment in which the suspension outside the permeable membrane is replaced with new one. The suspension may be replaced in succession or at a predetermined interval. Such an interval may be a regular or an irregular period of time. For example, the suspension may be replaced at an interval of 1 hour, 2 hours, 3 hours, 6 hours, 12 hours, 24 hours, 2 days, 3 days, 4 days, 7 days, or the like within a range of 1 hour to 1 week, but it is not limited thereto.

The ratio of absorbance ('absorbance ratio') of ½ means that the absorbance after t (that is, incubation time) becomes half the initial absorbance, that is, approximately half of the porous silica particles was degraded.

The t at which the absorbance ratio in Mathematical Equation 1 above reaches ½ is 20 or more, or 24 or more, for example, may be in a range of 20 to 120, in particular, 20 to 96, 20 to 72, 30 to 70, 40 to 70, 50 to 65, or the like within the above range, but it is not limited thereto.

With regard to the above particles, the t at which the absorbance ratio in Mathematical Equation 1 above reaches ⅕ may be in a range of 70 to 140, for example, 80 to 140, 80 to 120, 80 to 110, 70 to 140, 70 to 120, 70 to 110, or the like within the above range, but it is not limited thereto.

With regard to the above particles, the t at which the absorbance ratio in Mathematical Equation 1 above reaches 1/20 may be in a range of 130 to 220, for example, 130 to 200, 140 to 200, 140 to 180, 150 to 180, or the like within the above range, but it is not limited thereto.

With regard to the above particles, the t at which the measured absorbance becomes 0.01 or less may be 250 or more, for example, 300 or more, 350 or more, 400 or more, 500 or more, 1000 or more, and the like, and the upper limit may be 2000, but it is not limited thereto.

With regard to the above particles, the absorbance ratio and tin Mathematical Equation 1 above have high correlation therebetween. For instance, Pearson correlation coefficient may be at least 0.8, for example, at least 0.9, at least 0.95 or the like.

The tin Mathematical Equation 1 above means a degradation rate of the porous silica particles in an environment similar to the inside of the body ('in vivo-like environment'). For example, the above degradation rate may be controlled by adjusting a surface area, a particle diameter, a pore diameter, substituents on the surface of the particle or inside the pores of the particle, compactness of the surface or the like.

More particularly, the t may be reduced by increasing the surface area of the particles, or otherwise, the t may be increased by decreasing the surface of the particles. The surface area of the particles may be controlled by adjusting the diameter of the particles, or the diameter of the pores. Further, placing the substituent on the surface of the particle and/or inside the pores of the particle may reduce direct exposure of the porous silica particles to an environment (e.g., solvent, etc.), thereby increasing the t. Further, such direct exposure of the porous silica particles to the environment may be reduced by carrying the cell fate modulating factor in the porous silica particles and increasing affinity between the cell fate modulating factor and the porous silica particles, thereby increasing the t. Further, the particles may be formed with more compact surface, thus to increase the t. Hereinabove, various examples for regulating the tin Mathematical Equation 1 have been described, but it is not limited thereto.

With regard to the composition of the present invention, the porous silica particles may be particles made of silica ($SiO_2$) materials, and have a diameter of several nanometers to several micrometers.

An average diameter of the particles may be in a range of 100 to 1000 nm, for example, 100 to 800 nm, 100 to 500 nm, 100 to 400 nm, 100 to 300 nm, 100 to 200 nm, or the like within the above range, but it is not limited thereto.

With regard to the composition of the present invention, the porous silica particles may be porous particles having nano-sized pores, which can carry the cell fate modulating factor on the surface of the particle or inside the pores of the particle.

An average pore diameter of the particles may be in a range of 1 to 100 nm, for example, 5 to 100 nm, 7 to 100 nm, 7 to 50 nm, 10 to 50 nm, 10 to 30 nm, 7 to 30 nm, or the like within the above range, but it is not limited thereto. Instead, in consideration of an amount and a size of the cell fate modulating factor to be carried, the pore diameter is preferably selected and adjusted.

With regard to the composition of the present invention, the form of the porous silica particles is not particularly limited to a specific shape. However, in consideration of some aspects such as smooth interaction between the particles and the subject cells to be modulated, it is preferable that the particles have a spherical shape.

With regard to the composition of the present invention, the porous silica particles may have a BET surface area in a range of 200 to 700 $m^2/g$. For example, the BET surface area may be 200 to 700 $m^2/g$, 200 to 650 $m^2/g$, 250 to 650 $m^2/g$, 300 to 700 $m^2/g$, 300 to 650 $m^2/g$, 300 to 600 $m^2/g$, 300 to 550 $m^2/g$, 300 to 500 $m^2/g$, 300 to 450 $m^2/g$, or the like within the above range, but it is not limited thereto.

With regard to the composition of the present invention, the porous silica particles have a volume per gram (g) in a range of 0.7 to 2.2 ml, for example, 0.7 to 2.0 ml, 0.8 to 2.2 ml, 0.8 to 2.0 ml, 0.9 to 2.0 ml, 1.0 to 2.0 ml, or the like within the above range, but it is not limited thereto. If the volume per g is excessively decreased, a degradation rate may be increased too much, thus causing difficulties in preparation of excessively large particles or not having a complete shape thereof.

With regard to the composition of the present invention, the porous silica particles have surface charge, that is, a zeta potential other than 0 mV. Therefore, particle aggregation due to electronic repulsion between the modified particles may be inhibited, and the cell fate modulating factor efficiently carried in the particles may be delivered to a target cell.

The surface charge value of the particles, that is, the zeta potential may be in a range of +1 to +150 mV, +2 to 130 mV or +3 to +100 mV if positively charged, but it is not limited thereto. On the other hand, if negatively charged, the zeta potential may be in a range of, −150 to −1 mV, −130 to −10 mV or −100 to −18 mV, but it is not limited thereto. The zeta potential value may be properly adjusted for purposes thereof in consideration of some aspects such as types or an amount of the cell fate modulating factor to be carried in the particles, control of the release rate or the like.

With regard to the composition of the present invention, the porous silica particles may carry the cell fate modulating factor on the surface of the particle and/or inside the pores of the particle.

The cell fate modulating factor may be carried in the particles by, for example, mixing the cell fate modulating factor with the porous silica particles in the solvent. The solvent used may be water and/or an organic solvent, and the organic solvent may include, for example: ethers (in particular, cyclic ethers) such as 1,4-dioxane, etc.; halogenated hydrocarbons such as chloroform, methyl chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methyl isobutylketone, cyclohexanone, etc.; aromatic hydrocarbons such as benzene, toluene, xylene, tetramethyl benzene, etc.; alkylamides such as N,N-dimethylformamide, N,N-dibutylformamide, N,N-dimethyl acetamide, N-methyl pyrrolidone, etc.; alcohols such as methanol, ethanol, propanol, butanol, etc.

The solvent used herein may further include phosphate buffered saline solution (PBS), simulated body fluid (SBF), borate-buffered saline, tris-buffered saline or the like.

A relative ratio of the porous silica particles and the cell fate modulating factor is not particularly limited but may be in a ratio by weight of 1:0.05 to 0.8, for example, 1:0.05 to 0.7, 1:0.05 to 0.6, 1:0.1 to 0.8, 1:0.1 to 0.6, 1:0.2 to 0.8, 1:0.2 to 0.6, or the like within the above range.

With regard to the composition of the present invention, the porous silica particles may gradually release the cell fate modulating factor carried therein over a long period of time.

The cell fate modulating factor carried in the particles may be biodegraded and released. In this case, the particles may be slowly degraded to allow sustained release of the carried cell fate modulating factor. This release may be controlled by, for example, adjusting the surface area, the particle diameter and/or the pore diameter of the porous silica particles, regulating substituents on the surface of the particle and/or inside the pores of the particle, surface compactness, or the like, but it is not limited thereto.

Further, the cell fate modulating factor carried in the particles may escape from the porous silica particles and also be released while being diffused. This process may be influenced by a relationship between the porous silica particles and the cell fate modulating factor, release environments of the cell fate modulating factor or the like. Therefore, the release of the cell fate modulating factor may be controlled by regulating the above conditions. For instance, the release of the cell fate modulating factor may be controlled by strengthening or weakening a binding force between the porous silica particles and the cell fate modulating factor through surface modification.

According to a more preferable example, when the carried cell fate modulating factor is poorly soluble (hydrophobic), the surface of the particle and/or inside the pores of the particle may have a hydrophobic substituent, thus to increase the binding force of the particles to the cell fate modulating factor, and thereby enabling sustained release of the cell fate modulating factor. For instance, the above particles may be surface-modified with alkoxysilane having a hydrophobic substituent.

In the present disclosure, the term "poorly soluble" may include the meanings of "insoluble", "practically insoluble" or "only slightly soluble" to water, etc., which is a term defined in "Pharmaceutical Science" 18$^{th}$ Edition (published by U.S.P., Remington, Mack Publishing Company).

The poorly soluble cell fate modulating factor may have, for example, a water-solubility of less than 10 g/L at 1 atm and 25° C., preferably less than 5 g/L and, more preferably less than 1 g/L, but it is not limited thereto.

When the carried cell fate modulating factor is water-soluble (hydrophilic), the surface of the particle or inside the pores of the particle may have a hydrophilic substituent, thus to increase the binding force of the particles to the cell fate modulating factor, and thereby enabling sustained release of the cell fate modulating factor. For instance, the porous silica particles may be surface-modified with alkoxysilane having a hydrophilic substituent.

The water-soluble cell fate modulating factor may have, for example, a water-solubility of 10 g/L or more at 1 atm and 25° C., but it is not limited thereto.

When the carried cell fate modulating factor is charged, the surface of the particle and/or the inside the pores of the particle may be counter-charged, thus to increase the binding force between the porous silica particles and the cell fate modulating factor, thereby enabling sustained release of the cell fate modulating factor. For instance, the porous silica particles may be surface-modified with alkoxysilane having an acidic group or a basic group.

More particularly, if the cell fate modulating factor is positively charged at neutral pH, the surface of the particle and/or the inside the pores of the particle may be negatively charged at neutral pH, thus to increase the binding force between the porous silica particles and the cell fate modulating factor, and thereby enabling sustained release of the cell fate modulating factor. For instance, the porous silica particles may be surface-modified with alkoxysilane having an acidic group such as carboxyl (—COOH), or sufonic acid group (—SO$_3$H), etc.

Further, if the cell fate modulating factor is negatively charged at neutral pH, the surface of the particle and/or the inside the pores of the particle may be positively charged at neutral pH, thus to increase the binding force between the porous silica particles and the cell fate modulating factor, and thereby enabling sustained release of the cell fate modulating factor. For instance, the porous silica particles may be surface-modified with alkoxysilane having a basic group such as amino, or other nitrogen-containing groups, etc.

The carried cell fate modulating factor may be released over, for example, 7 days to 1 year or more depending upon release environments, the porous silica particles used for carrying the same and the like.

With regard to the composition of the present invention, the porous silica particles may be biodegradable and can be entirely degraded about 100%, therefore, the cell fate modulating factor carried therein may be released to 100%.

With regard to the composition of the present invention, the porous silica particles may be formed by, for example, processes for preparation of particles having small pores and expansion of the pores. If necessary, the particles may be formed through further processes of calcination, surface modification and the like. When both processes of the calcination and the surface modification have been conducted, the particles may be surface-modified after the calcination.

The particle having small pores may have an average pore diameter of, for example, 1 to 5 nm, and may be obtained by adding a surfactant and a silica precursor to a solvent, followed by agitation and homogenization.

The solvent used herein may be water and/or an organic solvent. The organic solvent may include, for example: ethers (in particular, cyclic ethers) such as 1,4-dioxane, etc.; halogenated hydrocarbons such as chloroform, methyl chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methyl isobutylketone, γ-butyrolactone, 1,3-dimethyl-imidazolinone, methylethylketone, cyclohexanone, cyclopentanone, 4-hydroxy-4-methyl-2-pentanone, etc.; aromatic hydrocarbons such as benzene, toluene, xylene, tetramethyl benzene, etc.; alkylamides such as N,N-dimethylformamide, N,N-dibutylformamide, N,N-dimethyl acetamide, N-methyl pyrrolidone, etc.; alcohols such as methanol, ethanol, propanol, butanol, etc.; glycol ethers (cellosolve) such as ethyleneglycol monoethylether, ethyleneglycol monomethylether, ethyleneglycol monobutylether, diethyleneglycol monoethylether, diethyleneglycol monomethylether, diethyleneglycol monobutylether, propyleneglycol monomethylether, propyleneglycol monoethylether, dipropyleneglycol diethylether, triethyleneglycol monoethylether, etc.; other compounds including, for example, methyl acetamide (DMAc), N,N-diethyl acetamide, dimethyl formamide (DMF), diethyl formamide (DEF), N,N-dimethyl acetamide (DMAc), N-methyl pyrrolidone (NMP), N-ethyl pyrrolidone (NEP), 1,3-dimethyl-2-imidazolidinone, N,N-dimethylmethoxy acetamide, dimethyl sulfoxide, pyridine, dimethylsulfone, hexamethyl phosphoamide, tetramethylurea, N-methyl caprolactam, tetrahydrofuran, m-dioxane, P-dioxane, 1,2-dimethoxyethane or the like. Preferably, alcohol and, more preferably, methanol may be used, but it is not limited thereto.

When using a mixed solvent of water and the organic solvent, a relative ratio therebetween may be in a ratio by volume of 1:0.7 to 1.5, for example, 1:0.8 to 1.3, but it is not limited thereto.

The surfactant may include, for example, cetyltrimethylammonium bromide (CTAB), hexadecyltrimethylammonium bromide (TMABr), hexadecyltrimethylpyridinium chloride (TMPrCl), tetramethylammonium chloride (TMACl) or the like. Preferably, CTAB is used.

The surfactant may be added in an amount of 1 to 10 g to 1 liter of the solvent, for example, 1 to 8 g, 2 to 8 g, 3 to 8 g, or the like within the above range, but it is not limited thereto.

The silica precursor may be added after adding the surfactant to the solvent and agitating the same. The silica precursor may include, for example, tetramethyl orthosilicate (TMOS), but it is not limited thereto.

For instance, the agitation may be conducted for 10 to 30 minutes, but it is not limited thereto.

The silica precursor may be added in an amount of 0.5 to 5 ml to 1 liter of the solvent, for example, 0.5 to 4 ml, 0.5 to 3 ml, 0.5 to 2 ml, 1 to 2 ml, or the like within the above range, but it is not limited thereto. If necessary, sodium hydroxide may be further added as a catalyst. In this case, this compound may be added while agitating the same after adding the surfactant and before adding the silica precursor to the solvent.

The sodium hydroxide may be added in an amount of 0.5 to 8 ml to 1 liter of the solvent in terms of 1 M sodium hydroxide solution, for example, 0.5 to 5 ml, 0.5 to 4 ml, 1 to 4 ml, 1 to 3 ml, 2 to 3 ml, or the like within the above range, but it is not limited thereto.

After adding the silica precursor, the solution may undergo a reaction under agitation. The agitation may be conducted for 2 to 15 hours, for example, 3 to 15 hours, 4 to 15 hours, 4 to 13 hours, 5 to 12 hours, 6 to 12 hours, 6 to 10 hours, or the like within the above range, but it is not limited thereto. If the agitation time (reaction time) is too short, it may result in insufficient nucleation.

After the agitation, the solution may be subjected to aging. The aging may be conducted for 8 to 24 hours, for example, 8 to 20 hours, 8 to 18 hours, 8 to 16 hours, 8 to 14 hours, 10 to 16 hours, 10 to 14 hours, or the like within the above range, but it is not limited thereto.

Thereafter, a reaction product may be washed and dried to prepare porous silica particles. If necessary, unreacted materials may be removed before washing. For instance, such removal may be conducted by separating a supernatant through centrifugation.

The centrifugation may be conducted at 6,000 to 10,000 rpm for 3 to 60 minutes, for example, 3 to 30 minutes, 4 to 30 minutes, 5 to 30 minutes, or the like within the above range, but it is not limited thereto.

The washing may be conducted with water and/or an organic solvent. More particularly, since different types of materials are dissolved in different solvents, water and the organic solvent may be used once or several times by turns. Alternatively, the water or organic solvent may be used alone for washing once or several times. The several times may be 2 times or more but 10 times or less, preferably, 3 times or more but 10 times or less, 4 times or more but 8 times or less, 4 times or more but 6 times or less or the like.

The organic solvent may include, for example: ethers (in particular, cyclic ethers) such as 1,4-dioxane, etc.; halogenated hydrocarbons such as chloroform, methyl chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methyl isobutylketone, γ-butyrolactone, 1,3-dimethyl-imidazolinone, methylethylketone, cyclohexanone, cyclopentanone, 4-hydroxy-4-methyl-2-pentanone, etc.; aromatic hydrocarbons such as benzene, toluene, xylene, tetramethyl benzene, etc.; alkylamides such as N,N-dimethylformamide, N,N-dibutylformamide, N,N-dimethyl acetamide, N-methyl pyrrolidone, etc.; alcohols such as methanol, ethanol, propanol, butanol, etc.; glycol ethers (cellosolve) such as ethyleneglycol monoethylether, ethyleneglycol monomethylether, ethyleneglycol monobutylether, diethyleneglycol monoethylether, diethyleneglycol monomethylether, diethyleneglycol monobutylether, propyleneglycol monomethylether, propyleneglycol monoethylether, dipropyleneglycol diethylether, triethyleneglycol monoethylether, etc.; other compounds including, for example, methyl acetamide (DMAc), N,N-diethyl acetamide, dimethyl formamide (DMF), diethyl formamide (DEF), N,N-dimethyl acetamide (DMAc), N-methyl pyrrolidone (NMP), N-ethyl pyrrolidone (NEP), 1,3-dimethyl-2-imidazolidinone, N,N-dimethylmethoxy acetamide, dimethyl sulfoxide, pyridine, dimethylsulfone, hexamethyl phosphoamide, tetramethylurea, N-methyl caprolactam, tetrahydrofuran, m-dioxane, P-dioxane, 1,2-dimethoxyethane or the like. Preferably, alcohol and, more preferably, ethanol may be used, but it is not limited thereto.

The washing may be conducted under centrifugation, for example, at 6,000 to 10,000 rpm. The washing may be conducted for 3 to 60 minutes, for 3 to 30 minutes, 4 to 30 minutes, to 30 minutes, or the like within the above range, but it is not limited thereto.

Alternatively, the washing may be conducted while filtering the particles through a filter without centrifugation. The filter used herein may be provided with pores having a pore diameter equal to or less than the diameter of the porous silica particles. By filtering the reacting solution, the particles only remain on the filter, and may be washed by pouring water and/or an organic solvent onto the filter.

During washing, the water and organic solvent may be used once or several times by turns. Otherwise, the water or organic solvent may be used alone for washing once or several times. The several times may be 2 times or more but 10 times or less, preferably, 3 times or more but 10 times or less, 4 times or more but 8 times or less, 4 times or more but 6 times or less or the like.

The drying may be conducted at, for example, 20° C. to 100° C., but it is not limited thereto. Alternatively, the drying may be conducted under a vacuum condition.

Thereafter, the obtained porous silica particles may undergo pore expansion, and the pore expansion may be conducted using a pore expanding agent.

The pore expanding agent used herein may include, for example, trimethylbenzene, triethylbenzene, tripropylbenzene, tributylbenzene, tripentylbenzene, trihexylbenzene, toluene, benzene or the like. Preferably, trimethylbenzene may be used, but it is not limited thereto.

Further, the pore expanding agent used herein may include, for example, N,N-dimethylhexadecylamine (DMHA), but it is not limited thereto.

The pore expansion may be conducted by, for example, mixing the porous silica particles in a solvent with the pore expanding agent and heating the same to conduct a reaction. The solvent used herein may include water and/or an organic solvent. The organic solvent may include, for example: ethers (in particular, cyclic ethers) such as 1,4-dioxane, etc.; halogenated hydrocarbons such as chloroform, methyl chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methyl isobutylketone, cyclohexanone, etc.; aromatic hydrocarbons such as benzene, toluene, xylene, etc.; alkylamides such as N,N-dimethylformamide, N,N-dibutylformamide, N,N-dimethyl acetamide, N-methyl pyrrolidone, etc.; alcohols such as methanol, ethanol, propanol, butanol, etc. Preferably, alcohol and, more preferably, ethanol may be used, but it is not limited thereto.

The porous silica particles may be added in an amount of 10 to 200 g to 1 liter of the solvent, for example, 10 to 150 g, 10 to 100 g, 30 to 100 g, 40 to 100 g, 50 to 100 g, 50 to 80 g, 60 to 80 g, or the like within the above range, but it is not limited thereto.

The porous silica particles may be uniformly dispersed in the solvent. For instance, the porous silica particles may be added to the solvent, followed by ultrasonic dispersion. When using a mixed solvent, the porous silica particles may be dispersed in a first solvent, followed by adding the same to a second solvent.

The pore expanding agent may be added in an amount of 10 to 200 parts by volume ('vol. parts') to 100 vol. parts of the solvent, for example, 10 to 150 vol. parts, 10 to 100 vol. parts, 10 to 80 vol. parts, 30 to 80 vol. parts, 30 to 70 vol. parts, or the like within the above range, but it is not limited thereto.

The reaction may be conducted at 120 to 180° C., for example, at 120 to 170° C., 120 to 160° C., 120 to 150° C., 130 to 180° C., 130 to 170° C., 130 to 160° C., 130 to 150° C., or the like within the above range, but it is not limited thereto.

The reaction may be conducted for 24 to 96 hours, for example, 30 to 96 hours, 30 to 96 hours, 30 to 90 hours, 30 to 80 hours, 30 to 72 hours, 24 to 80 hours, 24 to 72 hours, 36 to 96 hours, 36 to 80 hours, 36 to 72 hours, 36 to 66 hours, 36 to 60 hours, 48 to 96 hours, 48 to 88 hours, 48 to 80 hours, 48 to 72 hours, or the like within the above range, but it is not limited thereto.

By adjusting the time and the temperature within the above-exemplified ranges, the reaction may be sufficiently but not excessively conducted. For instance, as the reaction temperature is decreased, the reaction may be conducted with increased reaction time. On the other hand, when the reaction temperature is decreased, the reaction time may be decreased. If the reaction is insufficiently performed, pore expansion may also be not sufficient. On the other hand, if the reaction is redundantly performed, particles may be collapsed due to over-expansion of pores.

The reaction may be conducted, for example, while raising a reaction temperature stepwise. More particularly, the reaction may be conducted by raising the temperature stepwise from room temperature to the above temperature at a rate of 0.5° C./min to 15° C./min, for example, 1° C./min to 15° C./min, 3° C./min to 15° C./min, 3° C./min to 12° C./min, 3° C./min to 10° C./min, or the like within the above range, but it is not limited thereto.

After the reaction, the reacting solution may be gradually cooled, for example, the temperature may be decreased stepwise to cool the reacting solution. In particular, the cooling may be conducted by decreasing the above temperature to room temperature stepwise at a rate of 0.5° C./min to 20° C./min, for example, 1° C./min to 20° C./min, 3° C./min to 20° C./min, 3° C./min to 12° C./min, 3° C./min to 10° C./min, or the like within the above range, but it is not limited thereto.

After the cooling, the reaction product may undergo washing and drying to prepare porous silica particles having expanded pores.

If necessary, unreacted materials may be removed before washing. For instance, such removal may be conducted by separating a supernatant through centrifugation.

The centrifugation may be conducted at 6,000 to 10,000 rpm. Further, the centrifugation may be conducted for 3 to 60 minutes, for example, 3 to 30 minutes, 4 to 30 minutes, 5 to 30 minutes, or the like within the above range, but it is not limited thereto.

The washing may be conducted using water and/or an organic solvent. More particularly, since different types of materials are dissolved in different solvents, water and the organic solvent may be used once or several times by turns. Alternatively, the water or organic solvent may be used alone for washing once or several times. The several times may range from 2 to 10 times, for example, 3 times, 4 times, 5 times, 6 times, 7 times, 8 times or the like.

The organic solvent may include, for example: ethers (in particular, cyclic ethers) such as 1,4-dioxane, etc.; halogenated hydrocarbons such as chloroform, methyl chloride, carbon tetrachloride, 1,2-dichloroethane, dichloroethylene, trichloroethylene, perchloroethylene, dichloropropane, amyl chloride, 1,2-dibromoethane, etc.; ketones such as acetone, methyl isobutylketone, cyclohexanone, etc.; aromatic hydrocarbons such as benzene, toluene, xylene, etc.; alkylamides such as N,N-dimethylformamide, N,N-dibutylformamide, N,N-dimethyl acetamide, N-methyl pyrrolidone, etc.; alcohols such as methanol, ethanol, propanol, butanol, etc. Preferably, alcohol and, more preferably, ethanol may be used, but it is not limited thereto.

The washing may be conducted under centrifugation at 6,000 to 10,000 rpm. Further, the centrifugation may be conducted for 3 to 60 minutes, for example, 3 to 30 minutes, 4 to 30 minutes, 5 to 30 minutes, or the like within the above range, but it is not limited thereto.

The washing may also be conducted by filtering the particles without centrifugation. The filter may have a pore diameter equal to or less than the diameter of the porous silica particles. The particles only may remain on the filter by filtering the reacting solution and be washed by pouring water and/or an organic solvent into the filter.

The water and organic solvent may be used once or several times by turns during washing. Otherwise, the water or organic solvent may be used alone for washing once or several times. The several times may be 2 times or more but 10 times or less, preferably, 3 times or more but 10 times or less, 4 times or more but 8 times or less, 4 times or more but 6 times or less or the like.

The drying may be conducted at 20 to 100° C., but it is not limited thereto. Further, the drying may also be conducted under a vacuum condition.

Thereafter, the obtained particles may undergo calcination. The calcination is a process of heating particles to endow the surface and inside of the particle with a more compact structure while removing any organic matter filled in the pores of the particles.

More particularly, in the particles subjected to the calcination, silanol groups (Si—OH) on the surface of the particles are bonded together to occur dehydration and form siloxane groups (Si—O—Si) instead of the silanol groups, thus causing structural shrinkage of the particles. In this case, the particles may have structural compactness and less of silanol groups on the surface thereof, thus causing slow self-degradation of the particles. Therefore, it is possible to achieve desirable effects of the composition according to the present invention, that is, sustained and continuous release of the cell fate modulating factor.

The calcination process may be conducted at, for example, 400 to 700° C. for 3 to 8 hours, preferably, at 500 to 600° C. for 4 to 5 hours, but it is not limited thereto.

Thereafter, the obtained porous silica particles may undergo modification of the surface of the particle and/or the inside pores of the particle.

With regard to the composition of the present invention, the porous silica particles may be prepared by, for example, processes for preparation of particles having small pores, pore expansion, surface modification and modification of inside the pores.

The processes for preparation of particles having small pores and for pore expansion may be performed by the above-described processes. Thereafter, washing and drying may be conducted.

If necessary, unreacted materials may be removed before washing. For instance, such removal may be conducted by separating a supernatant through centrifugation.

The centrifugation may be conducted at 6,000 to 10,000 rpm for 3 to 60 minutes, for example, 3 to 30 minutes, 4 to 30 minutes, 5 to 30 minutes, or the like within the above range, but it is not limited thereto.

The washing process after preparation of the particles having small pores may be conducted by the method/under the conditions within the above-exemplified ranges, but it is not limited thereto.

The washing process after pore expansion may be conducted under more alleviated conditions, compared to the above-exemplified aspects. For instance, the washing may be conducted 3 times or less, but it is not limited thereto.

Modification of the surface of the particle and/or the inside pores of the particle may be performed by the above-described method. Surface modification of the particle and then modification of inside pores of the particle may be sequentially conduced in this order. Alternatively, a washing process of the particle may be further conducted between the above two processes.

When washing under more alleviated conditions after the preparation of particles having small pores and the pore expansion, a reacting solution such as the surfactant used in particle preparation and/or pore expansion is filled inside the pores. Therefore, the inside the pores is not modified during surface modification, instead, the surface only may be modified. Thereafter, the reacting solution inside the pores may be removed by washing the particles.

The particle washing between the surface modification and the modification of inside the pores may be conducted using water and/or an organic solvent. More particularly, since different types of materials are dissolved in different solvents, water and the organic solvent may be used once or several times by turns. Alternatively, the water or organic solvent may be used alone for washing once or several times. The several times may be 2 times or more but 10 times or less, preferably, 3 times or more but 10 times or less, 4 times or more but 8 times or less, 4 times or more but 6 times or less or the like.

The washing may be conducted under centrifugation. The centrifugation may be conducted at 6,000 to 10,000 rpm for 3 to 60 minutes, for example, 3 to 30 minutes, 4 to 30 minutes, 5 to 30 minutes, or the like within the above range, but it is not limited thereto.

Alternatively, the washing may be conducted while filtering the particles through a filter without centrifugation. The filter used herein may contain pores having a pore diameter equal to or less than the diameter of the porous silica particles. By filtering the reacting solution, the particles only remain on the filter, and may be washed by pouring water and/or an organic solvent onto the filter.

During the washing, the water and the organic solvent may be used once or several times by turns. Alternatively, the water or organic solvent may be used alone for washing once or several times. The several times may be 2 times or more but 10 times or less, preferably, 3 times or more but 10 times or less, 4 times or more but 8 times or less, 4 times or more but 6 times or less or the like.

The drying may be conducted at, for example, 20° C. to 100° C., but it is not limited thereto. Alternatively, the drying may be conducted under a vacuum condition.

With regard to the composition of the present invention, the cell subjected to cell fate modulation may include any cell and any stem cell, for example, at least one selected from the group consisting of: embryonic stem cell, adult stem cell, induced multipotent stem cell, mesenchymal stem cell, dermoblast, lymphocyte, myelocyte, neural progenitor cell, spinal cell, adipocyte, hepatocyte, dermal cell, hemocyte, myeloblast, fibroblast, endothelial cell, nerve cell, muscle cell, immunocyte, myocardial cell, brain cell, bone cell, oral cell, periodontal cell, hair follicle cell, mucosa cell, epithelial cell, mesenchmal cell, mesenchymal cell, placetocyte, cord blood cell, stem cell, gastrointestinal tract cell, amnion cell, retinal cell, cartilage cell, pancreatic cell, pancreatic beta cell, vascular cell and lung fibroblast cell. However, on the basis of various factors such as types of cell fate modulating factors carried, purposes and/or stages of modulating the cell fate, or the like, the subject cell may be freely selected without particular limitation thereof.

Use of the composition according to the present invention may include regulating a fate of subject cells, more particularly, treating a culture medium for various cells as described above with the composition including porous silica particles, which carry a cell fate modulating factor therein, such that: the cells in an undifferentiated state may be differentiated into cells under differentiation, or otherwise, into fully differentiated cells; the cells under differentiation or the fully differentiated cells may be reverse-differentiated into the cells in an undifferentiated state; or specific differentiated cells may be directly differentiated into another specific differentiated cells.

Effects of cell fate modulation by the composition of the present invention have high efficiency and remarkably high level of success. For instance, degradation may have a rate of success ranging from 5 to 80%, 5 to 75%, 5 to 70%, 5 to 65%, 5 to 60%, 5 to 55% or 5 to 50%. In a case of reverse degradation, the rate of success may range from 0.0001 to 10%, 0.0001 to 9%, 0.0001 to 8%, 0.0001 to 7%, 0.0001 to 6%, 0.0001 to 5%, 0.0001 to 4%, 0.0001 to 3% or 0.0001 to 2%. Further, in a case of direct degradation, the rate of success may range from 5 to 90%, 5 to 85%, 5 to 80%, 5 to 75%, 5 to 70%, 5 to 65% or 5 to 60%.

The use and effects described above are based on high carrying rate of cell fate modulating factor and stable delivery of the same into subject cells by the porous silica particles according to the present invention, and sustained and continuous release and almost 100% release of the carried cell fate modulating factor. Therefore, disadvantages of conventional cell fate modulation methods using the cell fate modulating factor may be overcome, thereby accomplishing excellent effects of cell fate modulation.

Further, the present invention provides a novel method for modulating cell fate, which includes treatment of subject cells for fate modulation using the composition of the present invention.

With regard to this modulation method, subject matters in regard to a cell fate modulating factor contained in the above composition, porous silica particles and the subject cells, will be substantially the same as described above.

Hereinafter, the present invention will be described in detail by means of the following examples.

In the following examples, the porous silica particles of the present invention may be given with nomenclature of DDV or MSN. Similarly, the surface-modified porous silica particles may be designated ADDV or mDDV, while the porous silica particles surface-modified with an amino group may be designated ADDV or AMSN.

Example 1: Preparation of Porous Silica Particle (1) Preparation of Particle 1

1) Preparation of Particle Having Small Pore 960 mL of distilled water (DW) and 810 mL of MeOH were fed to a 2 L round-bottom flask. After feeding 7.88 g of CTAB to the flask, 4.52 mL of 1M NaOH was rapidly added while agitating. Agitating 10 minutes provided a uniformly mixed solution, followed by adding 2.6 mL of TMOS thereto. After agitating 6 hours and uniformly mixing the same, the resultant mixture was subjected to aging for 24 hours.

Thereafter, the reacting solution was centrifuged with 8,000 rpm at 25° C. for 10 minutes to remove a supernatant, and then, centrifuged again with 8,000 rpm at 25° C. for 10 minutes and washed using ethanol and distilled water 5 times by turns.

Then, drying the washed product in an oven at 70° C. provided 1.5 g of powdery porous silica particles having small pores (average pore diameter of 2 nm, and particle diameter of 200 nm).

2) Expansion of Pore 1.5 g of the powdery porous silica particles having small pores was added to 10 ml of ethanol and then treated by ultrasonic dispersion. 10 ml of water and 10 ml of trimethyl benzene (TMB) were added and then treated again by ultrasonic dispersion.

Then, the dispersion was placed in an autoclave and reacted at 160° C. for 48 hours.

The reaction was initiated at 25° C. then continued by raising the temperature at a rate of 10° C./min, followed by gradually cooling at a rate of 1 to 10° C./min.

The cooled reacting solution was centrifuged with 8,000 rpm at 25° C. for 10 minutes to remove a supernatant, then, centrifuged again with 8,000 rpm at 25° C. for 10 minutes, followed by washing using ethanol and distilled water 5 times by turns.

Thereafter, the resulting product was dried in an oven at 70° C. to obtain powdery porous silica particles (pore diameter of 10 to 15 nm, and particle diameter of 200 nm).

3) Calcination

The porous silica particles prepared in the above step 2) were put in a glass vial and heated at 550° C. for 5 hours. After completion of the reaction, the heated particles were prepared by slowly cooling to room temperature.

(2) Preparation of Particle 2

Porous silica particles were prepared by the same procedures as described in Example 1-(1) except that the reaction conditions during pore expansion were altered into 140° C. and 72 hours.

(3) Preparation of Particle 3 (10 L Scale)

Porous silica particles were prepared by the same procedures as described in Example 1-(1) except that a 5-fold large container was used and the materials used herein were increased by 5 times in quantities thereof.

(4) Preparation of Particle 4 (Particle Diameter of 300 nm)

Porous silica particles were prepared by the same procedures as described in Example 1-(1) except that 920 ml of distilled water and 850 ml of methanol were used in the preparation of particles having small pores.

(5) Preparation of Particle 5 (Particle Diameter of 500 nm)

Porous silica particles were prepared by the same procedures as described in Example 1-(1) except that 800 ml of distilled water, 1010 ml of methanol and 10.6 g of CTAB were used in the preparation of particles having small pores.

(6) Preparation of Particle 6 (Particle Diameter of 1,000 nm)

Porous silica particles were prepared by the same procedures as described in Example 1-(1) except that 620 ml of distilled water, 1380 ml of methanol and 7.88 g of CTAB were used in the preparation of particles having small pores.

(7) Preparation of Particle 7 (Pore Diameter of 4 nm)

Porous silica particles were prepared by the same procedures as described in Example 1-(1) except that 2.5 mL of TMB was used during pore expansion.

(8) Preparation of Particle 8 (Pore Diameter of 7 nm)

Porous silica particles were prepared by the same procedures as described in Example 1-(1) except that 4.5 mL of TMB was used during pore expansion.

(9) Preparation of Particle 9 (Pore Diameter of 10 nm)

Porous silica particles were prepared by the same procedures as described in Example 1-(1) except that 6.5 mL of TMB was used during pore expansion.

(10) Preparation of Particle 10 (Pore Diameter of 17 nm)

Porous silica particles were prepared by the same procedures as described in Example 1-(1) except that 11 mL of TMB was used during pore expansion.

(11) Preparation of Particle 11 (Pore Diameter of 19 nm)

Porous silica particles were prepared by the same procedures as described in Example 1-(1) except that 11.8 mL of TMB was used during pore expansion.

(12) Preparation of Particle 12 (Pore Diameter of 23 nm)

Porous silica particles were prepared by the same procedures as described in Example 1-(1) except that 12.5 mL of TMB was used during pore expansion.

(13) Preparation of Particle 13 (Double Modification)

1) Preparation of Particle Having Small Pore

Particles having small pores were prepared by the same procedures as described in Example 1-(1)-1).

2) Expansion of Pore

The particles having small pores were reacted with TMB, cooled and centrifuged by the same procedures as described in Example 1-(1)-2), thereby removing a supernatant. Thereafter, the particles were centrifuged under the same conditions as those in Example 1-(1)-2) and washed using ethanol and distilled water 3 times by turns, followed by drying the same under the same conditions as those in Example 1-(1)-2), thereby obtaining powdery porous silica particles (pore diameter of 10 to 15 nm, and particle diameter of 200 nm).

3) Surface Modification

After dispersing 0.8 to 1 g of the porous silica particles having expanded pores, 5 mL of (3-aminopropyl)triethoxysilane was added thereto, followed by heating the same for 12 hours while refluxing at 20° C. After completion of the above-described washing and drying processes, 1 mL of 2-[2-(2-methoxyethoxy)ethoxy]acetic acid (PEG3), 100 mg of 1-Ethyl-3-(3-dimethylaminopropyl)carbodiimide (EDC) and 200 mg of N-Hydroxysuccinimide (NHS) were dispersed in 30 mL of PBS, followed by a reaction at room temperature for 12 hours while agitating. Thereafter, the product was subjected to the washing and drying processes as described above.

Since the reacting solution obtained from the previous step still remains inside the pores, the inside the pores were not modified.

4) Washing Inside the Pore 800 g of surface-modified particle powders were dissolved in 40 ml of 2M HCl/ethanol, and subjected to refluxing while vigorously agitating the same.

Thereafter, the cooled reacting solution was centrifuged at 8,000 rpm for 10 minutes to remove a supernatant, then, centrifuged again with 8,000 rpm at 25° C. for 10 minutes, followed by washing the same using ethanol and distilled water 5 times by turns.

Then, the product was dried in an oven at 70° C. to prepare powder)/porous silica particles.

5) Modification of Inside the Pore (i) A propyl group was introduced inside the pore by the same procedures as described in Example 2-(2)-1), which will be described below.

(ii) An octyl group was introduced inside the pore by the same procedures as described in Example 2-(2)-2), which will be described below.

Example 2: Surface Modification of Porous Silica Particle (1) Positively Charging of the Particle 1) Amino Group—Particle Having a Diameter of 300 nm The porous silica particles prepared in Example 1-(4) were reacted with 3-Aminopropyl)triethoxysilane (APTES), thus being positively charged.

More particularly, 100 mg of porous silica particles was dispersed in 10 mL of toluene contained in a 100 mL round-bottom flask by a bath sonicator. Then, 1 mL of APTES was added thereto, followed by agitating the same with 400 rpm at 130° C. to conduct a reaction for 12 hours.

After the reaction, the product was slowly cooled to room temperature, centrifuged with 8,000 rpm for 10 minutes to remove a supernatant, then, centrifuged again at 25° C. for 10 minutes, followed by washing the same using ethanol and distilled water 5 times by turns.

Thereafter, the product was dried in an oven at 70° C. to prepare powdery porous silica particles having an amino group on the surface of the particle and inside the pores of the particle.

2) Amino Group—Particle Having a Diameter of 200 nm (i) The porous silica particles prepared in Example 1-(1) were reacted with (3-Aminopropyl)triethoxysilane (APTES), thus being positively charged. Then, the charged product was modified by the same procedures as described in Example 2-(1)-1) except that 0.4 ml of APTES was added thereto and a reaction time was 3 hours.

(ii) The porous silica particles prepared in Example 1-(7) were reacted with (3-Aminopropyl)triethoxysilane (APTES), thus being positively charged. Then, the charged product was modified by the same procedures as described in Example 2-(1)-1).

(iii) The porous silica particles prepared in Example 1-(8) were reacted with (3-Aminopropyl)triethoxysilane (APTES), thus being positively charged. Then, the charged product was modified by the same procedures as described in Example 2-(1)-1).

(iv) The porous silica particles prepared in Example 1-(9) were reacted with (3-Aminopropyl)triethoxysilane (APTES), thus being positively charged. Then, the charged product was modified by the same procedures as described in Example 2-(1)-1).

(v) The porous silica particles prepared in Example 1-(10) were reacted with (3-Aminopropyl)triethoxysilane (APTES), thus being positively charged. Then, the charged product was modified by the same procedures as described in Example 2-(1)-1).

(vi) The porous silica particles prepared in Example 1-(11) were reacted with (3-Aminopropyl)triethoxysilane (APTES), thus being positively charged. Then, the charged product was modified by the same procedures as described in Example 2-(1)-1).

(vii) The porous silica particles prepared in Example 1-(12) were reacted with (3-Aminopropyl)triethoxysilane (APTES), thus being positively charged. Then, the charged product was modified by the same procedures as described in Example 2-(1)-1).

3) Amino Group—Difference in Surface Modification Extents Between Particles (i) The porous silica particles treated by the processes described in Example 1-(1)-1) to Example 1-(1)-3) were reacted with (3-Aminopropyl)triethoxysilane (APTES), thus being positively charged. Then, the charged product was modified by the same procedures as described in Example 2-(1)-1).

(ii) The porous silica particles prepared in Example 1-(9) were reacted with (3-Aminopropyl)triethoxysilane (APTES), thus being positively charged. Then, the charged product was modified by the same procedures as described in Example 2-(1)-1) except that a reaction time was 24 hours.

4) Aldehyde Group

The porous silica particles prepared in Example 2-(1)-3)-(ii) were reacted with glutaraldehyde (GA), thus being positively charged.

More particularly, 100 mg of porous silica particles were dispersed in 10 mL of distilled water contained in a 100 mL round-bottom flask by a bath sonicator. Then, 10 mL of GA was added thereto, followed by agitating the same with 400 rpm at room temperature to conduct a reaction for 12 hours.

After the reaction, the product was slowly cooled to room temperature, centrifuged with 8,000 rpm for 10 minutes to remove a supernatant, then, centrifuged again at 25° C. for 10 minutes, followed by washing the same using distilled water 5 times.

(2) Introduction of Hydrophobic Group

1) Propyl Group

The porous silica particles prepared in Example 1-(1) were reacted with trimethoxy(propyl)silane to introduce a propyl group on the surface of the particle and inside the pores of the particle. Then, the product was modified by the same procedures as described in Example 2-(1) except that 0.35 ml of trimethoxy(propyl)silane was added thereto instead of APTES and a reaction time was 12 hours.

2) Octyl Group

The porous silica particles prepared in Example 1-(1) were reacted with trimethoxy-n-octylsilane to introduce a propyl group on the surface of the particle and inside the pores of the particle. Then, the product was modified by the same procedures as described in Example 2-(1) except that 0.5 ml of trimethoxy-n-octylsilanee was added thereto instead of APTES and a reaction time was 12 hours.

(3) Negatively Charging of the Particle

1) Carboxyl Group

The porous silica particles prepared in Example 1-(1) were reacted with succinic anhydride, thus being negatively charged. Then, the product was modified by the same procedures as described in Example 2-(1)-1) except that: toluene was replaced by dimethyl sulfoxide (DMSO); 80 mg of succinic anhydride was added instead of APTES; the reaction was conducted at room temperature for 24 hours while agitating the same; and the distilled water was replaced by DMSO during washing.

2) Thiol Group

The modification was conducted by the same procedures as described in Example 2-(1)-1), except that APTES was replaced by 1.1 mL of MPTES.

3) Sulfonic Acid Group 100 mg of the porous silica particles prepared in Example 2-(3)-2) were dispersed in 1 mL of 1M sulfuric acid solution and 20 mL of 30% hydrogen peroxide, then, agitated at room temperature to induce oxidation, thereby oxidizing a thiol group into a sulfonic acid group. Then, the product was subjected to washing and drying by the same procedures as described in Example 2-(1)-1).

4) Methyl Phosphonate Group (i) The porous silica particles treated by the processes described in Example 1-(1)-1) to Example 1-(1)-3) were reacted with (3-Trihydroxysilyl)propyl methylphosphonate (THMP), thus being negatively charged. Then, the charged product was modified by the same procedures as described in Example 2-(1)-1).

More particularly, 100 mg of porous silica particles were dispersed in 10 mL of distilled water contained in a 100 mL round-bottom flask by a bath sonicator. Then, 3 mL of THMP and 1.5 mL of 1M HCl solution were added thereto, followed by agitating the same with 400 rpm and at 130° C. to conduct a reaction for 24 hours.

After the reaction, the product was slowly cooled to room temperature, centrifuged with 8,000 rpm for 10 minutes to remove a supernatant, then, centrifuged again at 25° C. for 10 minutes, followed by washing the same using distilled water 5 times.

(ii) The porous silica particles prepared in Example 1-(9) was reacted with 3-(Trihydroxysilyl)propyl methylphosphonate (THMP), thus being negatively charged. The charged product was modified by the sample procedure as described in (i).

(iii) The porous silica particles prepared in Example 1-(10) was reacted with 3-(Trihydroxysilyl)propyl methylphosphonate (THMP), thus being negatively charged. The charged product was modified by the sample procedure as described in (i).

(4) Introduction of Hydrophilic Group—PEG 100 mg of the porous silica particles prepared in Example 1-(1) was dispersed in 20 ml of N,N'-disuccinimidyl carbonate (DSC) solution having a concentration of 50 μg/ml and agitated at room temperature to bind the DSC to the surface of the porous silica particle. The particles were washed with 10 ml of distilled water 3 times. 10 mg of PEG having a molecular weight of 4 kDa and an amino group at an end thereof (HO-PEG-$NH_2$) was dispersed in 10 ml of the above solution and agitated at room temperature to bind the PEG to the surface of the silica particles. Thereafter, the obtained particles were washed and dried by the same procedures as described in Example 2-(1)-1).

Example 3: Carrying Cell Fate Modulating Factor (1) Retinoic Acid

To 100 μg of the porous silica particles prepared in each of Examples 1-(1) and (11), and Examples 2-(1)-2)-(i) and (vi) in 1 ml of distilled water, 1 ml of a retinoic acid solution (50 mM ethanol) was added, followed by settlement of the solution at room temperature for 4 hours and loading the same.

(2) CYC (Cyclopamine-KAAD)

To 100 μg of the porous silica particles prepared in Example 2-(2)-2) in 1 ml of distilled water, 0.5 ml of CYC solution (1 mM dimethyl sulfoxide (DMSO)) was added, followed by settlement of the solution at room temperature for 2 hours and loading the same.

(3) Activin a, BMP-4, KGF, bFGF, Noggin, Wnt, Nanog

After mixing 100 μg of the porous silica particles prepared in each of Examples 2-(3)-1), 3) and 4) and 10 μg of activin A, BMP-4, KGF, bFGF, FgF, Wnt, Nanog or Noggin in 0.2 ml of 1×PBS, the mixture was settled at 4° C. for 4 hours and then loaded.

(4) Plasmid DNA, Linear DNA, mRNA

After mixing 12.5 μg of the porous silica particles prepared in Example 2-(1)-2)-(vii), and 0.25 μg of plasmid DNA, linear DNA or mRNA of Oct4 (SEQ ID NO: 5), Sox2 (SEQ ID NOs: 6 and 7), Klf4 (SEQ ID NOs: 8, 9 and 10), c-Myc (SEQ ID NO: 11), Nanog (SEQ ID NOs: 12 and 13) or hTERT (SEQ ID NO: 14) in 1 ml of PBS, the mixture was settled at room temperature for 30 minutes and then loaded.

(5) Mir-21 (miRNA Family)

After mixing 10 μg of the porous silica particles prepared in Examples 2-(1)-2)-(v) and (vi), and 50 pmol of miR-21 (SEQ ID NO: 15) in 1×PBS, the mixture was settled at room temperature for 30 minutes and then loaded.

Experimental Example 1: Formation of Porous Silica Particles and Identification of Pore Expansion In order to identify whether the particles having small pores were uniformly generated and/or whether the porous silica particles were uniformly formed with sufficient pore expansion, the particles having small pores in the particles prepared in each of Examples 1-(1) to (3), as well as the prepared porous silica particles were observed by a microscope (FIGS. 1 to 4).

Figure 1:
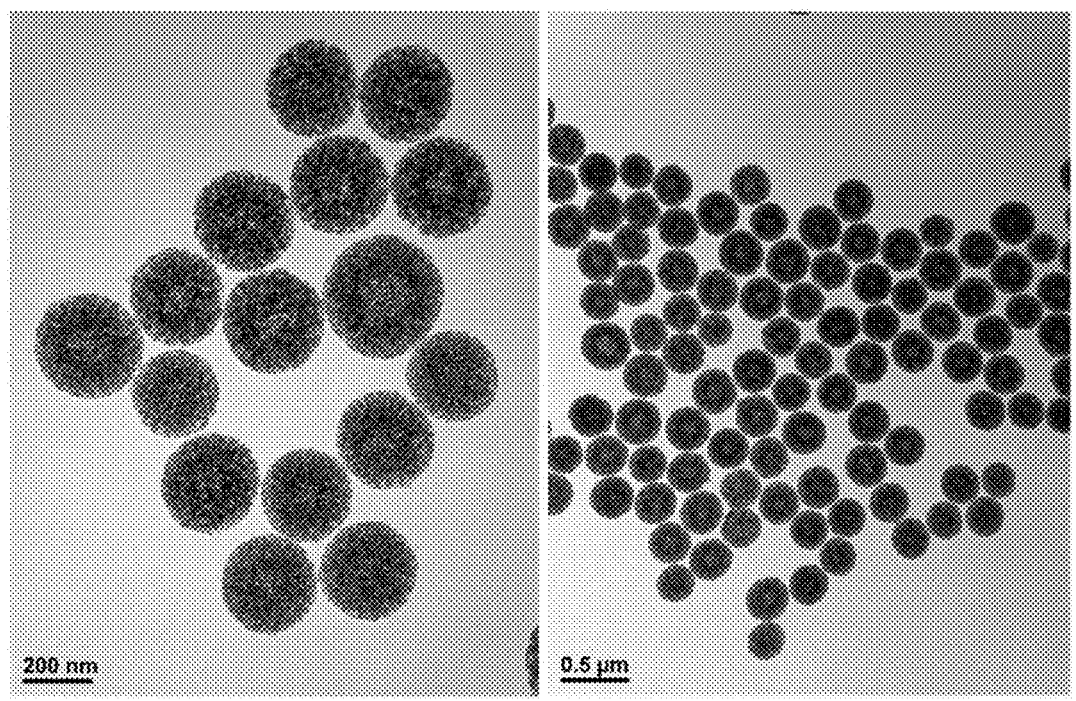
FIG. 1 is microphotographs illustrating porous silica particles according to one embodiment of the present invention.
Figure 2:
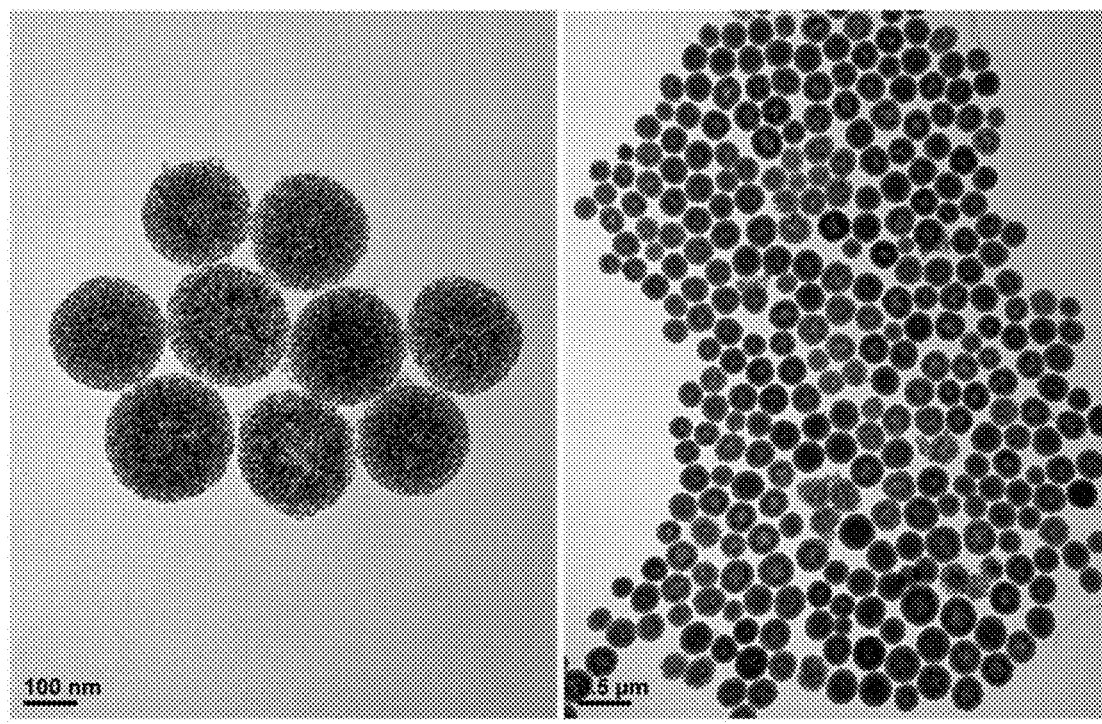
FIG. 2 is microphotographs illustrating porous silica particles according to one embodiment of the present invention.

FIG. 1 is photographs of the porous silica particles in Example 1-(1), and FIG. 2 is photographs of the porous silica particles in Example 1-(2), illustrating that spherical porous silica particles having sufficiently expanded pores have been uniformly formed.

Figure 3:
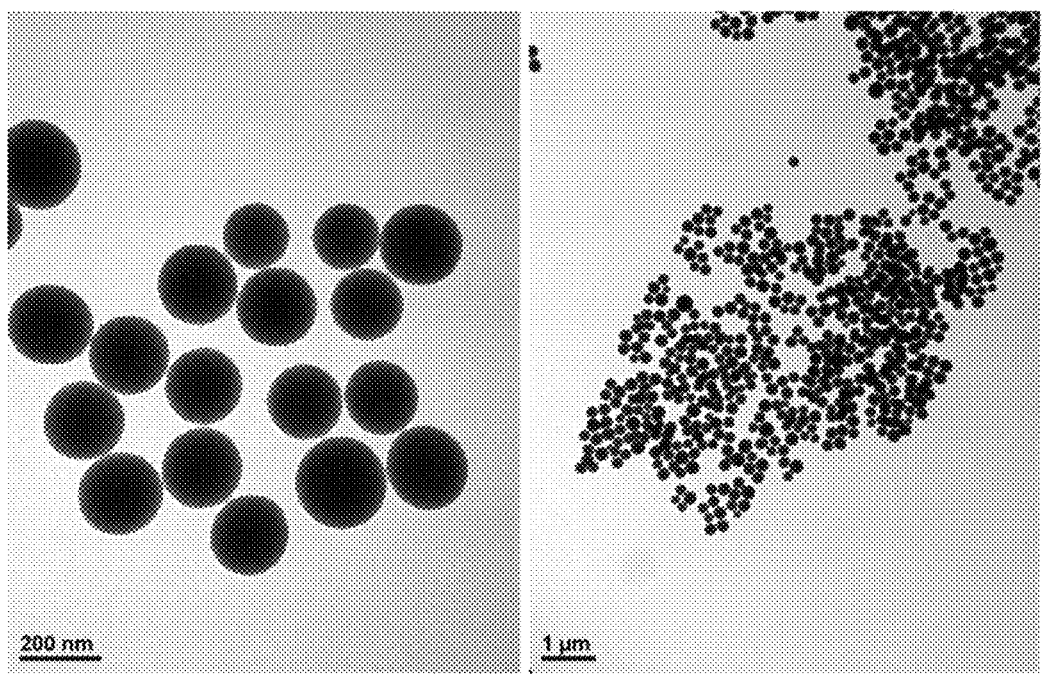
FIG. 3 is microphotographs illustrating particles having small pores during production of the porous silica particles according to one embodiment of the present invention.
Figure 4:
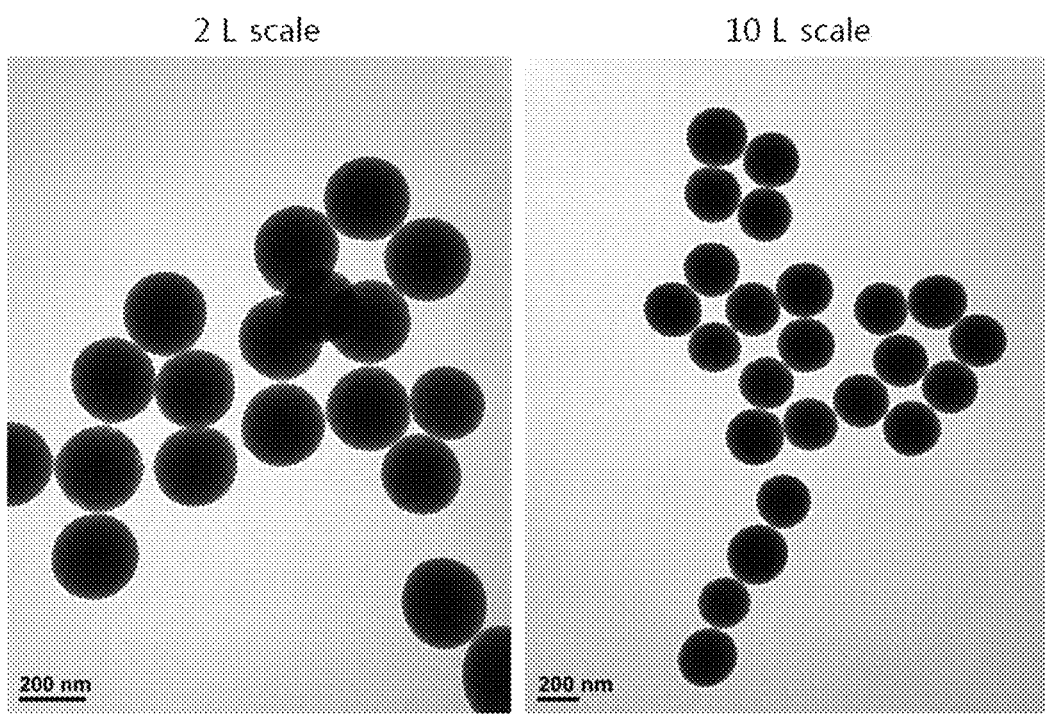
FIG. 4 is microphotographs illustrating particles having small pores according to one embodiment of the present invention.

FIG. 3 is photographs of the particles having small pores in Example 1-(1), and FIG. 4 is comparative photographs of both the particles having small pores in Example 1-(1) and Example 1-(3), illustrating that spherical particles having small pores have been uniformly formed.

Experimental Example 2: Measurement of Average Pore Diameter, BET Surface Area, Pore Volume and Zeta Potential of Porous Silica Particle (1) Measurement Method Surface areas and pore volumes of the particles having small pores in Example 1-(1), as well as the porous silica particles in each of Examples 1-(1), (7), (8), (9) and (11) and Examples 2-(1)-2)-(i), (ii), (iii), (iv) and (vi) were calculated. The surface area was calculated by a Brunauer-Emmett-Teller (BET) method, while the pore size and the pore volume were calculated by a Barrett-Joyner-Halenda (BJH) method.

Further, 100 μg of the porous silica particles was dispersed in 1 ml of PBS (pH 7.4), then moved to a disposable folded capillary cell (DTS1070) and mounted on a zeta-potential measurement device in order to measure zeta-potential.

(2) Results of Measurement

Figure 5:
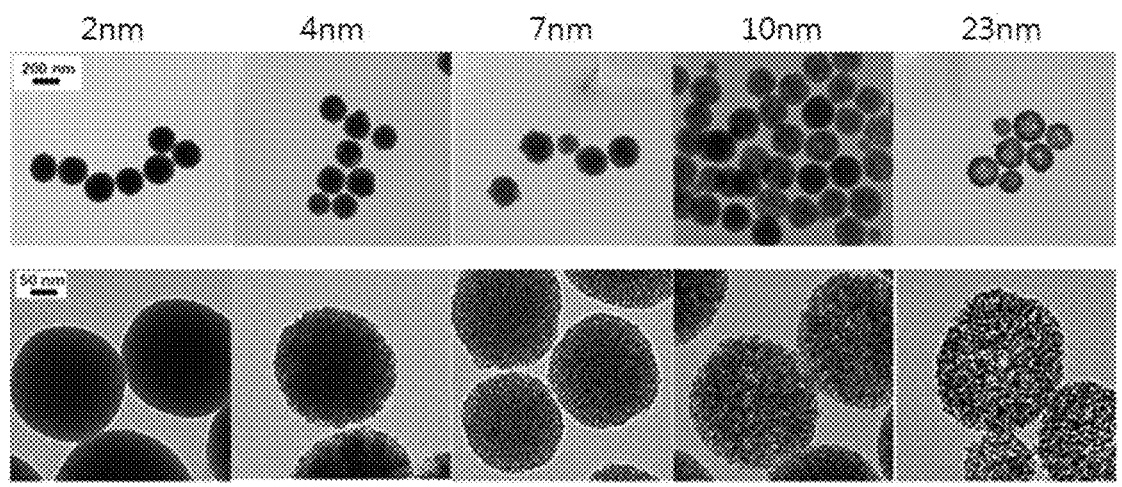
FIG. 5 is microphotographs illustrating porous silica particles for each pore diameter according to one embodiment of the present invention.
Figure 6:
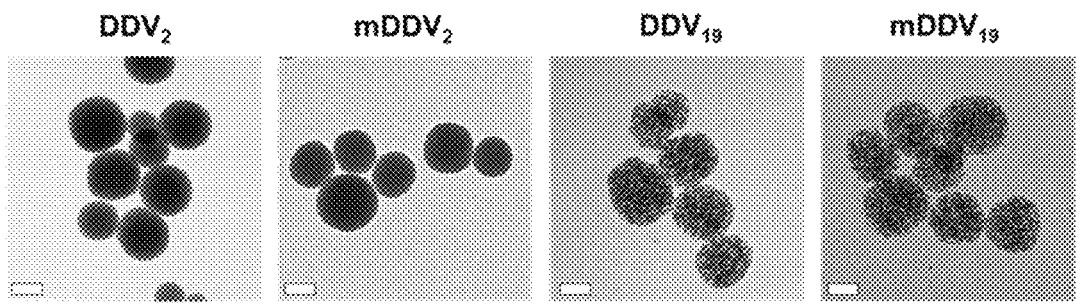
FIG. 6 is microphotographs illustrating typical porous silica particles having both particle diameters of 2 nm and 19 nm (DDV), respectively, as well as microphotographs illustrating porous silica particles with modified chemical functional groups (mDDV), according to one embodiment of the present invention.

Photographs of the above-described particles could be seen in FIGS. 5 and 6, while results of the calculation are shown in Table 1 below.

TABLE 1

|  | Average pore diameter (nm) | BET surface area (m²/g) | Pore volume (ml/g) | Zeta-potential (mV) |
|---|---|---|---|---|
| DDV$_2$ | 2 | 1305 to 1420 | 0.5 to 0.7 | −10 to −50 |
| mDDV$_2$ | 2 | 1150 to 1390 | 0.48 to 0.69 | +5 to +50 |
| DDV$_4$ | 4 | 598 to 950 | 0.6 to 0.8 | −10 to −50 |
| mDDV$_4$ | 4 | 550 to 940 | 0.59 to 0.78 | +5 to +50 |
| DDV$_7$ | 7 | 490 to 585 | 0.65 to 0.9 | −10 to −50 |
| mDDV$_7$ | 7 | 488 to 575 | 0.61 to 0.87 | +5 to +50 |
| DDV$_{10}$ | 10 | 460 to 487 | 0.68 to 0.95 | −10 to −50 |
| mDDV$_{10}$ | 10 | 440 to 480 | 0.65 to 0.92 | +5 to +50 |
| DDV$_{19}$ | 19 | 430 to 480 | 0.7 to 1.52 | −10 to −50 |
| mDDV$_{19}$ | 19 | 400 to 470 | 0.69 to 1.50 | +5 to +50 |
| DDV$_{23}$ | 23 | 300 to 460 | 0.8 to 1.7 | −10 to −50 |
| mDDV$_{23}$ | 23 | 250 to 450 | 0.78 to 1.69 | +5 to +50 |

Experimental Example 3: Cell Fate Modulating Factor Carrying Rate of Porous Silica Particle (1) Experimental Method 1) Cell Fate Modulating Factors Other than Retinoic Acid After loading various cell fate modulating factors in the porous silica particles by the same procedures as described in Examples 3-(2) to (5), respectively, an absorbance of the supernatant was measured. Otherwise, after staining the supernatant with a dye, the absorbance was measured. Further, a fluorescence intensity of the supernatant was analyzed to determine an amount of the carried cell fate modulating factor, thereby calculating a carrying rate of the same.

More particularly, the porous silica particles negatively charged were used for the factor positively charged at neutral pH, whereas the porous silica particles positively charged were used for the factor negatively charged at neutral pH. After loading the factors under different loading conditions for the factors, an amount of the remaining cell fate modulating factor on the supernatant without loading was determined by measuring absorbance or fluorescence of the supernatant. Further, an amount of the carried cell fate modulating factor was calculated (amount of cell fate modulating factor=initial feeding amount of cell fate modulating factor−amount of cell fate modulating factor remaining on supernatant), thus to identify a carrying rate of the factor (carrying rate=cell fate modulating factor/porous silica particle, w/w %).

2) Retinoic Acid

After loading retinoic acid to the porous silica particles prepared in each of Examples 1-(1) and (11) and Examples 2-(1)-2)-(i) and (vi), an absorbance of the supernatant in the loaded mixture was measured to determine an amount of the carried retinoic acid and calculate a carrying rate thereof.

More particularly, 1 ml of retinoic acid solution (50 mM ethanol) was added to

Figure 7B:
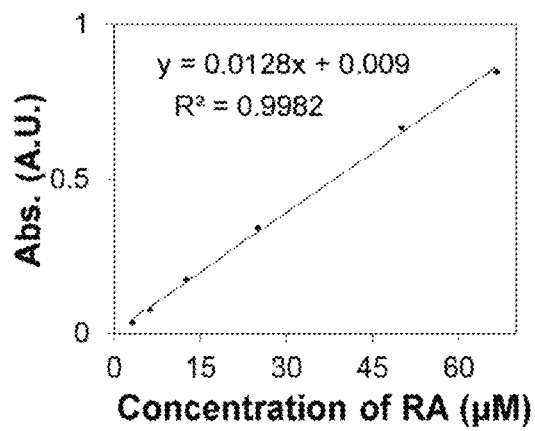

100 μg of porous silica particles in 1 ml of distilled water, settled at room temperature for 4 hours, followed by loading the same. Then, an absorbance was measured at $\lambda_{ab}$=350 nm to determine an amount of retinoic acid remaining on the supernatant without loading. Further, an amount of the carried retinoic acid was calculated (amount of retinoic acid=initial feeding amount of retinoic acid−amount of retinoic acid remaining on supernatant), thus to identify a carrying rate of the retinoic acid (carrying rate=retinoic acid/porous silica particle, w/w %) (FIGS. 7A and 7B).

(2) Results of Experiment

1) Cell Fate Modulating Factors Other than Retinoic Acid

Referring to Table 2 below, carrying rates of various cell fate modulating factors in the porous silica particles (cell fate modulating factor/porous silica particle; w/w %) according to the following experimental methods could be identified.

TABLE 2

| Group | Characteristic of cell fate modulating factor | Cell fate modulating factor | Zeta-potential of porous silica particle (mV) | Carrying rate (w/w %) |
|---|---|---|---|---|
| Low molecular weight compound | Positively charged at neutral pH | 3-isobutyl-1-methylxanthine, CHIR99021, KY02111, DZNep, tranylcypromine, LDN, digoxin, nicotinamide, etc. | −10 to −50 | 5 to 45 |
| | Negatively charged at neutral pH | IWP2, IWP4, KY02111, XAV939, TTNPB, PD0325901, A83-01, hiazovivin, DMH1, rosiglitazone, SB-431542, pifithrin-alpha, FSK (Forskolin), IDE1, IDE2, DAPT, CYC (cyclopamine-KAAD), PDBu, ascorbic acid, dexamethasone, 5-azacytidine, taurine, Kartogenin, ursolic acid, SR1555, halofunginone, CHIR99021, valproic acid, etc. | +5 to +48 | 5 to 45 |
| Bio-molecule | Positively charged at neutral pH | Dkk1, Lefty A, activin A, GATA4, Foxal, Foxa2, Mef2c, BMP4, IGF1, HGF, WNT, FGF10, KGF, bFGF, Klf4, CRX, RAX, OTX2, Ascl1, NFIA, NFIB, Fezf2, Hmga2, VEGF, LIF, TGF-β, SOX2, Noggin, etc. | −10 to −50 | 5 to 60 |
| | Negatively charged at neutral pH | nodal, Bm2, Mytl1, NeuroD1, Hnfla, Foxa3, Tbx5, Tymosin beta4, Tbx5, EGF, SOX9, Bestrophin1, Ctip2, NeuroG2, Atf5, Prox1, Hnf4a, OCT4, c-Myc, insulin, FGF9, Interleukins, etc. | +5 to +45 | 5 to 60 |
| Nucleic acid | Negatively charged at neutral pH | plasmid DNA, linear DNA, miRNA (miR-124, miR-9, miR9*, miR-302, miR-367, and miR-21, etc.), siRNA, modified RNA, noncoding RNA, mRNA, etc. | +5 to +45 | 5 to 40 |

2) Retinoic Acid

Referring to FIG. 8, it can be seen that, when the average pore diameter is 19 nm, a retinoic acid carrying rate is higher than the average pore diameter of 2 nm. Further, it was found that the retinoic acid carrying rate is higher when the surface of the porous silica particle or the inside pores of the particle is modified with an amino group than the case of without modification. Therefore, it can be confirmed that a pore size of the porous silica particles included in the inventive composition and whether or not to modify the surface of the particle are factors for influencing the carrying rate of the cell fate modulating factor containing retinoic acid.

Experimental Example 4: Identification of Biodegradation Property of Porous Silica Particle In order to identify biodegradation properties of the porous silica particles prepared in Example 1-(1), a level of biodegradation at 37° C. and SBF (pH 7.4) was observed at 0, 120 and 360 hour by a microscope, and results thereof are shown in FIG. 9. Referring to this figure, it can be seen that the porous silica particles were biodegraded and, after 360 hours, almost entirely biodegraded.

Experimental Example 5: Measurement of Absorbance Ratio of Porous Silica Particle Absorbance ratios for each time were measured according to Mathematical Equation 1 below.

$$A_t/A_0 \qquad \text{[Mathematical Equation 1]}$$

(wherein $A_0$ is an absorbance of the porous silica particles measured when 5 ml of suspension containing 1 mg/ml of porous silica particles is fed to a tubular permeable membrane having 50 kDa pores; 15 ml of a solvent substantially the same as the suspension is placed outside the permeable membrane while contacting the same; the inside/outside of the permeable membrane are under horizontal agitation with 60 rpm at 37° C.; and $A_t$ is another absorbance of the porous silica particle measured t time after the measurement of $A_0$.)

More particularly, 5 mg of the porous silica particles was diluted in 5 ml of SBF (pH 7.4). Then, 5 ml of the solution including porous silica particles was placed in a permeable membrane having a diameter of 50 kDa shown in FIG. 10. 15 ml of SBF was added to an outer membrane and SBF in the outer membrane was replaced with new one every 12 hours. Degradation of the porous silica particles was performed at 37° C. while horizontally agitating with 60 rpm. Thereafter, an absorbance of the particles was measured by UV-vis spectroscopy then analyzed at λ=640 nm.

(1) Measurement of Absorbance Ratio

Absorbance ratios of the porous silica particles prepared in Example 1-(1) were measured by the above method, and the measured results are shown in FIG. 11. Referring to this figure, t at which the absorbance ratio reaches ½ is about 58 hours, indicating that the particles are considerably slowly degraded.

(2) Measurement for Each Particle Diameter of Particles

Absorbances of the porous silica particles prepared in each of Examples 1-(1), (5) and (6) were measured by Mathematical Equation 1 above, and the measured results are shown in FIG. 12 (SBF was used as the suspension and solvent). Referring to this figure, it can be seen that t is reduced as a particle diameter of the particles is increased.

(3) Measurement for Each Average Diameter of Pores

Absorbances of the porous silica particles prepared in each of Examples 1-(9) and (10) and an absorbance of the particle silica particles having small pores prepared in Example 1-(1) as a control group were measured by Mathematical Equation 1 above, and the measured results are shown in FIG. 13 (SBF was used as the suspension and solvent). Referring to this figure, it can be seen that the porous silica particles of the examples have considerably higher t than the control group.

(4) Measurement for Each pH Value

Absorbances for each pH value of the porous silica particles prepared in Example 1-(4) were measured. The absorbances were measured in SBF and Tris at pH values of 2.5 and 7.4, respectively. Then, the measured results are shown in FIG. 14. Referring to this figure, t at which all absorbance ratios reach ½ was at least 20, although there is a difference between t values for each pH value.

(5) Measurement in Charged Case

Absorbances of the porous silica particles prepared Example 2-(1)-1 were measured and the measured results are shown in FIG. 15 (Tris (pH 7.4) was used as the suspension and solvent). Referring to this figure, it can be seen that the positively charged particles have also t of at least 20 at which an absorbance ratio reaches ½.

Experimental Example 6: Cytotoxicity Test of Porous Silica Particle

HepG2 cells were spread in an amount of 10,000 cells per well in a 96-well plate and, after 24 hours, the particles prepared in Example 2-(3)-4) were sequentially spread on each well in an order from the lowest concentration to the highest concentration. The plate was left for 24 hours and then a survival rate ('viability') of HepG2 cells was determined using a cell counting kit (CCK) (FIG. 16). According to the same procedure as described above, the particles prepared in Example 2-(1)-2)-(vi) were left for 48 hours and then the viability of mES (mouse embryonic stem cells) was determined (FIG. 17).

Referring to FIGS. 16 and 17, it can be seen that the composition including the porous silica particles of the present invention has insignificant effects on the viabilities of HepG2 cell line and mES cell line regardless of a concentration thereof, thereby identifying no cytotoxicity of the above composition.

Experimental Example 7: Intracellular Delivery of Porous Silica Particle (1) Experimental Method
1) Mouse Embryonic Stem Cells (mES)

After seeding cells in a gelatin-coated plate, this was cultured with a common mES culture medium for 24 hours. Intracellular delivery experiments were conducted using $AMSN_{19}$ marked with TAMRA dye ($TAMSN_{19}$) (Example 2-(1)-2)-(vi)). $TAMSN_{19}$ was prepared by a pre-optimized method and used for treatment of mES cells, followed by incubation at 37° C. under 5% carbon dioxide condition for 48 hours. Before sampling, the cells were treated with Hoechst 33342 for nucleus staining then the medium was removed after 15 minutes. Following this, the cells were washed with PBS twice and fixed with 4% paraformaldehyde. The medium was observed in Deltavision (GE healthcare) and intracellular delivery of $TAMSN_{19}$ in the medium was identified. Images were repeatedly obtained on different planes perpendicular to a z-axis. Fluorescence correlation analysis was performed by line profiling of image #3 of a z cross-section, which illustrates the most distinct image of a nucleus in a medium structure as well as the porous silica particles.

2) Fully-Differentiated Cell and Other Cells

Human fibroblasts, HepG2 cells, HeLa cells, lymphocytes, myelocytes, human embryonic stem cells, human nerve progenitor cells, respectively, were seeded in cell incubation plates, and treated and incubated using culture solutions generally used for cell culture. For intracellular delivery experiments, TAMRA dye carrying the cell fate modulating factors or FITC-marked particles stated in Example 3 were used.

The particles prepared by a pre-optimized method were used for treatment of cells, followed by incubation at 37° C. under a 5% carbon dioxide condition for 24 hours. Before sampling, the cells were treated with Hoechst 33342 for nucleus staining then the medium was removed after 15 minutes. Following this, the cells were washed with PBS twice and fixed with 4% paraformaldehyde. The medium was observed in Deltavision (GE healthcare) and fluorescent signals corresponding to TAMRA or FITC were observed by a confocal microscope.

(2) Results of Experiment
1) Mouse Embryonic Stem Cell (mES)

In order to observe whether $AMSN_{19}$ efficiently reaches a target cell (FIG. 18), $AMSN_{19}$ combined with 5-carboxytetramethylrhodamine (5-TAMRA) ($TAMSN_{19}$) was prepared for convenience. mES cells were cultured in a feeder-free system assisted by entire treatment of particles and gelatin coating on the surface of an incubation plate, thereby easily maintaining proper un-differentiation and growth conditions. Such un-differentiation state of cells was identified by formation and maintenance of colony-like characteristics. The cells were treated with 20 μg/mL of $TAMSN_{19}$ and cultured along with a stem cell verification serum. Under the conditions described above, the cells showed formation of a colony of the cells, which was clearly maintained. Further, a site of $TAMSN_{19}$ was observed within the colony. Intracellular intake of RA/MSN complex was discovered by fluorescence correlation analysis based on fluorescent cell images, and this was possibly achieved by z-sectioned imaging technique using a Deltavision™ imaging apparatus (FIG. 19). Referring to the z-sectioned image in the colony on the same plane, the particles (red) were mostly observed in the cytoplasm (blue). Successful internationalization of the particles within a single mES cell was identified in TEM image. It can be seen that the particles were not tangled with the surface of the cells but successfully placed in an cytoplasm region, thus to approach around a nucleus (blank points indicated by black and/or red arrows) (FIG. 20). Further, as a result of imaging by a transmission electron microscope (TEM) after delivering the particles to the stem cells, it can be concretely confirmed that endosomes were formed by endocytosis and delivered to the stem cells, thereafter, the particles escaped from the endosomes and released the cell fate modulating factor carried inside DDV (FIG. 21). Such data demonstrated that the particles have high potential ability of effectively delivering the cell fate modulating factor, which was carried in the colonized cells.

2) Fully-Differentiated Cell and Other Cells

Particles marked by 5-carboxytetramethylrhodamine (5-TAMRA) dye or FITC were prepared. According to the method in Experimental Example 7-(1)-2), the prepared particles were treated in human fibroblasts (A of FIG. 22), HepG2 cells (B of FIG. 22), HeLa cells (C of FIG. 22), lymphocytes (A of FIG. 23), myelocytes (B of FIG. 23), human embryonic stem cells (A of FIG. 24), and human nerve progenitor cells (B of FIG. 24) in vitro, while being treated in spinal cord tissues in vivo. As a result of the treatment, it can be seen that the particles were successfully internalized in these various cells and could effectively deliver the cell fate modulating factor.

Experimental Example 8: Release of Carried Cell Fate Modulating Factor (RA)

(1) Experimental Method

For RA release kinetic investigation, incubation was carried out in a RA solution for 4 days to produce RA/MSN complex. This complex was suspended in PBS 5% ethanol solution, followed by incubation at 37° C. for maximum 10 days. A calculated value of RA released from the complex was deduced by analyzing variation in UV absorption values at 350 nm of RA supernatant in each sample. UV absorption peaks were measured on alternate days and the calculated RA amounts were added to the previous data.

(2) Results of Experiment

According to the RA loading test, a release rate of RA carried in each particle was analyzed (FIGS. 26 and 27). As a result, compared to the particles having small pores (MSN$_2$, and AMSN$_2$), the particles having large pores (MSN$_{19}$, and AMSN$_{19}$) showed a profile of relatively sustained release rate and were almost 100% released within 10 days. From such data, it can be seen that a combination of the particles having large pores and an amine functional group is an element required for selecting most preferable particles for intracellular delivery of RA, which may endow a high carrying rate and sustained release characteristics.

Experimental Example 9: Modulation of Subjected Cell Fate (1) Experimental Method 1) Differentiation from Stem Cells to Nerve Cells Neural induction of mES cells was conducted by adding RA or RA/AMSN$_{19}$ complex. In particular, $10^{-6}$M RA or 25 μg of RA/AMSN$_{19}$ (corresponding to $3 \times 10^{-6}$M including RA) was used for treatment of mES cells in a complete mES medium for 2 days. A non-induction group was cultured as a negative control group. After 2 days, the medium was replaced with a new nerve cell culture medium, N2B27. The medium was replaced on alternate days.

2) Differentiation from Stem Cells to Pancreatic Endoderm

The embryonic stem cells were cultured in a RPMI culture solution including 100 ng/ml of activin A (ActA) and 25 ng/ml of Wnt3a for 1 day. On next day, the medium was replaced with a new one including 0.2% FBS and 100 ng/ml of ActA, and then, the culture was conducted for 2 days. Next, the cells were washed with PBS and cultured in a RPMI culture solution including 2% FBS and 25 to 50 ng/ml of KGF for 3 days. After 3 days, the medium was replaced with a DMEM medium including 1% B27 additive, 0.25 μM KAAD-cyclopamine (CYC), 2 μM retinoic acid (RA) and 50 ng/ml of Noggin (Nog), followed by incubation for 3 days. Thereafter, the medium was replaced with a new DMEM medium including 1% B27 additive. The above steps were executed by sequentially replacing the medium itself. Differentiation inducing materials added in the above steps (ActA, Wnt, KGF, RA, Cyc, and Nog) were carried and treated inside DDV in proper combinations in these steps, respectively. After 10 days, the differentiation induction efficiency was determined on the basis of expression levels of HNF6 and PDX1, which are pancreatic endoderm differentiation marker genes (FIG. 34).

3) Differentiation from Stem Cells to Cardiomyocytes

The embryonic stem cells were seeded on Matrigel-coated plates with a density of $1 \times 10^5$ cells/cm$^2$, and cultured in a MEF-CM medium including 8 ng/ml of bFGF/FGF for 6 days. Then, the cells were treated with 100 ng/ml of activin A (ActA) in a MEF-CM medium including RPMI-B27 for 1 day, followed by treatment with 10 ng/ml of BMP4 for 4 days. Then, the culture medium was replaced with a new RPMI-B27 medium every 2 to 3 days for 2 to 3 weeks. Differentiation inductive materials added in the above step were carried inside DDV in proper combinations thereof and used for treatment of the cells. After 14 days, inductive efficiency of cardiomyocyte differentiation was determined with a level of expression of a cardiomyocyte-specific protein, that is, cardiac troponin T (cTnT) (FIG. 35).

4) Reverse Differentiation from Fibroblasts or Blood Cells to Induced Multipotent Stem Cells (i) Preparation of DNA Template After amplifying human Oct4, Klf4, Sox2, Nanog, c-myc and TERT in Example 3, respectively, through PCR in pcDNA3 (Life technologies) plasmid backbone, the amplified product was cut with a proper restriction enzyme and then conjugated using a ligase, thereby preparing a DNA template (FIG. 36).

(ii) Preparation of mRNA with 2000 bp or Less

Using 1 to 5 ng of plasmid, 2 unit Platinum Taq polymerase (Life Technologies), 1×PCR buffer w/o MgCl$_2$, 2.8 mM of MgCl$_2$, 0.5 μM of sense primer, 0.5 μM of antisense primer and 200 μm of dNTPs resulted in a whole 25 μl of PCR reaction volume, followed by PCR reaction under conditions including at 95° C. for 3 min, 35 cycles at 95° C. for 30 s, 60° C. for 30 s, 72° C. for 60 s per 1 kb and finally 72° C. for 3 min.

(iii) Preparation of mRNA with 2000 bp or More

Using 10 ng of plasmid, 5 unit LongAmp Taq DNA polymerase (New England Biolabs), 1× LongAmp Taq reaction buffer, 2 μM of sense primer, 2 μM of antisense primer and 300 μm of dNTPs resulted in a whole 50 μl PCR reaction volume, followed by PCR reaction under conditions including 95° C. for 3 min, 35 cycles at 94° C. for 10 s, 60° C. for 60 s, 65° C. for 50 s per 1 kb and finally 65° C. for 3 min.

(iv) mRNA IVT, Transfection and Reprogramming

1 μg of plasmid or 0.5 μg of PCR product was formed in a template, followed by synthesizing IVT-RNA (In vitro transcription-RNA) using T7mScript Standard mRNA production System (Epicentre Biotechnologies). To the synthesized RNA, Cap 1 structure was conjugated using V. virus-derived capping enzyme and 2'-O-methyltrasferase, and poly A tail was further conjugated by means of mScript™ polymerase enzyme kit (Epicentre Biotechnologies). The synthesized RNA was purified by GeneJet RNA purification kit (Thermo Fisher). The purified mRNA (Oct4, Sox2, Klf4, c-Myc, Nanog, and hTERT) was used in a form of a mRNA mixture of mRNAs in equivalent amounts or GFP mRNA carried in DDV (Example 3) to treat the cells. Fibroblasts (human foreskin fibroblasts) were seeded in an amount of $2 \times 10^6$ cells per well on 6-well plates coated with 0.1% gelatin. The cells were cultured under 5% 02 condition for 24 hours before transfection. Before the transfection, the cell medium was replaced with an OPTI-MEM basal medium (Life Technologies). The mRNA mixture or GFP mRNA was diluted in 150 mM NaCl solution (PolyPlus), and DDV was also diluted in 150 mM NaCl solution. Then, these two solutions were mixed together and left at room temperature for 5 to 10 minutes. Thereafter, the cells were treated with the above solution to conduct transfection. After 4 hours, the solution was replaced with a fibroblast medium. The transfection process was conducted at an interval of 48 hours for 2 weeks. Thereafter, the number of mRNA-IPS colonies was counted to determine reverse differentiation induction efficiency (FIG. 37).

5) Direct Differentiation Between Myeloid Cells and Fibroblasts

After separating monocytes from mouse peripheral blood, these were first differentiated into macrophages using hMCSF and polymixin B. These macrophages were treated with LPS (1 microgram/ml) and IFN-gamma (20 ng/ml) to polarize the same into M1 type macrophages. After stabilizing the prepared macrophages in a culture dish, miR-21 RNA was carried inside DDV and fed to a culture solution containing cells. Thereafter, the cells were fixed with 4% paraformaldehyde and then treated with PBS 10% (v/v) FBS and 0.01% (v/v) Tween-20 for 30 minutes for cell blocking, followed by culturing the same along with a primary antibody (anti-FSP1 antibody 1:400) at 4° C. overnight. After washing the same with PBS twice, the cells were coated with a secondary antibody (Anti-Rat IgG, 1:1000/Anti-rabbit IgG, 1:1000). After incubation at room temperature for 2 hours, the sample was washed with PBS twice, followed by mounting the same with DAPI-containing Vectashield™ mounting solution after removing the cover glass from a culture plate. The prepared cells were subjected to analysis of fluorescent signals by a confocal microscope, thus to determine efficiency of direct differentiation.

6) RT-PCR

Using TRIZOL reagent, RNA was cut off from each sample. According to instructions, cDNA synthesis was assisted by Superscript™ reverse-enzyme. In order to amplify a target gene, a primer was designed in consideration of GC content of less than 50% and duplication of the same between two axons of the target gene. Sequences of primers are shown in Table 3 below.

TABLE 3

| OCT4 | Forward (SEQ ID NO: 1) | 5'-GCTCAGCCTTAAGAACATGTGTAAG C-3' |
|---|---|---|
| | Reverse (SEQ ID NO: 2) | 5'-GCCTCATACTCTTCTCGTTGGGA-3' |
| Tuj1 | Forward (SEQ ID NO: 3) | 5'-TCAGCGATGAGCACGGCATA-3' |
| | Reverse (SEQ ID NO: 4) | 5'-CACTCTTTCCGCACGACATC-3' |

7) Immunocytochemistry

With regard to immunocytochemistry, mES cells were plated on a gelatin-coated cover glass, treated with RA or RA/MSN, and then subjected to neural differentiation as described above. After fixing the product with 4% paraformaldehyde, it was treated with PBS 10% (v/v) FBS and 0.01% (v/v) Tween-20 for 30 minutes for blocking the cells. Then, the cells were cultured along with a primary antibody (Tuj1:Rat anti-Tuj1, 1:200/OCT4:Rabbit anti-OCT4, 1:100) at 4° C. overnight. After washing the product with twice, a secondary antibody (Anti-Rat IgG, 1:1000/Anti-rabbit IgG, 1:1000) corresponding to each body was applied thereto. After incubation at room temperature for 2 hours, the obtained sample was rinsed with PBS twice, followed by mounting the same with DAPI-containing Vectashield™ mounting solution.

8) Quantitative Analysis

For quantitative analysis, 5 representative fluorescent images were obtained from different immunostain samples, respectively. The images were analyzed by an ImageJ program. For Tuj1-positive cell analysis, the number of florescent cells expressing Tuj1 more than a critical value was measured from each image, followed by calculating a ratio of the measured number to a total number of nuclei. For measurement of a length of axon, axons contained in 50 cells in each sample were analyzed by a line measurement device. In consideration of 100 representative axons, an average value was calculated.

(2) Results of Experiments

1) Differentiation from Stem Cells to Nerve Cells

Referring to FIG. 28, when the culture medium was changed to N2B27, most of cells treated with RA or RA/AMSN$_{19}$ were dead and the survived cells showed an increase in cytoplasm and thus specific change in morphology. More particularly, the cells treated with RA/AMSN$_{19}$ exhibited a clear change in morphology in terms of fibrous texture, as compared to RA treated cells, thereby quick and active increase in the cytoplasm part. A whole form of the cells treated with RA alone is substantially similar to mES cell colonies since it has demonstrated that induction by RA alone for 2 days is not sufficient to induce important neural differentiation. In contrast, when mES cells were exposed under nerve cell culture conditions without RA treatment, the cells did not survive.

Referring to FIGS. 29 and 30, in order to assess whether nerve cells are successfully generated, total RNAs could be separated from each sample and results of analyzing gene expression OCT4 (multipotent marker) and β-III tubulin (Tuj1, nerve-specific marker) by a RT-PCR method could be identified. According to analysis of relative gene expression levels, the expression level of OCT4 was decreased while that of Tuj1 was increased in both RA and RA/AMSN$_{19}$ samples. More particularly, the samples treated with RA/AMSN$_{19}$ for 2 days showed remarkably increased Tuj1 expression, as compared to the samples treated with 2.5-fold amount of RA alone.

Referring to FIG. 31, in order to analyze expressions of the markers in terms of protein levels, results of conducting immunostaining analysis could be identified using specific antibodies for OCT4 or Tuj1. Expression of relative marker proteins discovered by immunocytochemistry was closely related with the results of mRNA expression analysis. In particular, the cells treated with RA/AMSN$_{19}$ showed extremely low expression of OCT4, while having a fibrous reticular structure to show high Tuj1 expression. In contrast, cells derived with RA alone have maintained a colony structure and OCT4 expression. Tuj1 expression was observed in both the colony and independent single cells partially separated from the colony. Unlike a RA/AMSN$_{19}$ administration group, Tuj1 expression was limited to a nucleus region in short fibrous structure of cytoplasm and showed less elongated shape.

Referring to FIG. 32, it can be identified a cell conversion efficiency graph determined by analyzing a rate of Tuj1 positive cells among entire cells survived after neural induction, wherein the cells induced using RA/AMSN$_{19}$ exhibited almost 90% cell conversion efficiency, whereas a RA single administration group exhibited about 30% cell conversion efficiency.

Referring to FIG. 33, results of analyzing axonal elongation showed that the RA/AMSN$_{19}$-treated group has a 4-fold longer length of axons than the control group.

The above data indicated that RA single addition only is not sufficient to satisfy a critical value of RA concentration required for activating neural differentiation, while intracellular RA supply could easily satisfy a specific critical value of RA concentration required for more effectively initiating nerve conversion with help of AMSN$_{19}$.

2) Differentiation from Stem Cells to Pancreatic Endoderm

More particularly, a culture solution of pancreatic endoderm cells was removed after completion of the differentiation induction and then washed with 200 μl of PBS (1×). Herein, it was notable that the cells were not completely dried. Using 200 μl of paraformaldehyde (PFA) fixation buffer, the cells were fixed at room temperature for 20 minutes, followed by washing the same with PBS 3 to 5 times. 200 μl of permeabilization buffer was added to a cell membrane at room temperature for 20 minutes, in order to improve permeability of the cell membrane. After removing the buffer, PBS was added thereto, followed by settlement for 5 minutes and then washing the solution. This process was repeated 3 times. Then, after adding 4% BSA blocking buffer, the solution was settled for 45 minutes and first staining was conducted by adding PBS including HNF6 and PDX1 primary antibodies. Thereafter, PBS including fluorescent marked secondary antibodies was added to conduct second staining. The number of cells positive to HNF6 and PDX1 was counted by confocal microscopy to determine a differentiation rate.

As a result of determining the differentiation rate by the above method, Table 5 showed high differentiation rates.

3) Differentiation from Stem Cells to Cardiomyocytes

More particularly, a culture solution of cardiomyocytes was removed after completion of the differentiation induction and then washed with 200 μl of PBS (1×). Herein, it was notable that the cells were not completely dried. Using 200 μl of paraformaldehyde (PFA) fixation buffer, the cells were fixed at room temperature for 20 minutes, followed by washing the same with PBS 3 to 5 times. 200 μl of permeabilization buffer was added to a cell membrane at room temperature for 20 minutes, in order to increase a permeability of the cell membrane. After removing the buffer, PBS was added thereto, followed by settlement for 5 minutes and then washing the solution. This process was repeated 3 times. Then, after adding 4% BSA blocking buffer, the solution was settled for 45 minutes and first staining was conducted by adding PBS including cTnT primary antibodies. Thereafter, PBS including fluorescent marked secondary antibodies was added to conduct second staining. The number of cells positive to cTnT was counted by confocal microscopy to determine a differentiation rate.

As a result of determining the differentiation rate by the above method, Table 5 showed high differentiation rates.

4) Reverse Differentiation from Fibroblasts or Blood Cells to Induced Multipotent Stem Cells Referring to Table 4 below, it can be seen that, when Oct4, Klf4, Sox2, Nanog or, DNA or mRNA of Tert was carried in DDV and delivered to fibroblasts or adult cells such as blood cells, high reverse differentiation rate could be obtained irrespective of bp lengths of DNA and mRNA. This result is considered due to stabilization and sustained and continuous release of the above factors through the porous silica particles included in the inventive composition.

TABLE 4

| | Length (bp) | Transfection rate (%) | Intracellular expression rate (%) | Differentiation induction rate (%) | Reverse differentiation induction rate (%) |
|---|---|---|---|---|---|
| DDV + mRNA (Oct4, Klf4, Sox2, Nanog, TERT, c-myc) | 1-1500 | 70-90 | 65-85 | 60-80 | 1-10 |
| | 1501-2500 | 50-75 | 40-65 | 35-60 | 1-10 |
| | 2501-4000 | 15-30 | 5-20 | 5-15 | 0.0001-2 |
| DDV + linear DNA (Oct4, Klf4, Sox2, Nanog, TERT, c-myc) | 1-1500 | 70-90 | 65-85 | 60-80 | 1-10 |
| | 1501-2500 | 50-75 | 40-65 | 35-60 | 1-10 |
| | 2501-4000 | 15-30 | 5-20 | 5-15 | 0.0001-3 |
| DDV + pDNA (Oct4, Klf4, Sox2, Nanog, TERT, c-myc) | 1-4500 | 70-90 | 65-85 | 60-80 | 1-10 |
| | 4501-9500 | 70-90 | 65-85 | 60-80 | 1-10 |
| | 9001-15000 | 15-30 | 5-20 | 5-15 | 0.0001-2 |

5) Forward, Reverse and Direct Differentiation Between Myeloid Cells and Fibroblasts Referring to Table 5 below, it can be seen that, when 5-azacytidine, Kortogenin, CHIR, 616452 (TGF-β Inhibitor), FSK, DZNep, VEGF, TGFbeta-1, Oct4, Sox2, Klf4, c-MYC and miRNA-21 were carried in DDV and delivered to nerve cells or fibroblasts, high forward differentiation rate, reverse differentiation rate and direct differentiation rate could be obtained. This result is considered due to stabilization and sustained and continuous release of the above factors through the porous silica particles including the inventive composition.

TABLE 5

|  | Cell fate modulating factor | Transfection rate (%) | Forward differentiation rate (%) | Reverse differentiation rate (%) |
|---|---|---|---|---|
| Low molecular weight compound | 5-azacytidine | 50-95 | 5-30 | N/D |
|  | Kortogenin, retinoic acid, Cyclopamine-KAAD (CYC) | 70-95 | 5-20 | N/D |
|  | CHIR, 616452, FSK, DZNep, | 30-75 | N/D | 0.0001-2 |
| Bio-molecule | VEGF, KGF, FGF, bFGF Noggin (Nog) | 50-95 | 40-80 | N/D |
|  | TGFbeta-1 Activin A, Wnt, BMPs | 50-95 | 30-70 | N/D |
|  | Oct4, Sox2, Klf4, c-Myc | 20-80 | N/D | 0.0001-2 |
|  | miRNA-21 | 40-90 | 5-60 (direct differentiation rate) | |

What is claimed is:

1. A composition, comprising:
a cell fate modulating factor in a therapeutically effective amount to treat a subject in need thereof;
porous silica particles which carry the cell fate modulating factor on a surface of the particle or inside pores of the particle, the porous silica particles having t of 20 to 120 hours at which an absorbance of the porous silica particles after t hours becomes half an initial absorbance of the porous silica particles, the porous silica particles having an average diameter of 100 to 1,000 nm and an average pore diameter of 1 to 100 nm.

2. The composition according to claim 1, wherein the particle has a siloxane group on the surface of the particle or inside the pores of the particle.

3. The composition according to claim 1, wherein the cell fate modulating factor is a gene encoding: at least one selected from the group consisting of 3-isobutyl-1-methylxanthine, CHIR, KY02111, DZNep, tranylcypromine, LDN, digoxin, nicotinamide, IWP2, IWP4, XAV939, TTNPB, PD0325901, A83-01, hiazovivin, DMH1, rosiglitazone, SB-431542, pifithrin-alpha, FSK, IDE1, IDE2, DAPT, CYC, PDBu, Retinoic acid, ascorbic acid, dexamethasone, 5-azacytidine, taurine, Kartogenin, ursolic acid, SR1555, halofunginone, CHIR99021, valproic acid, Dkk1, Lefty A, activin A, GATA4, Foxa1, Foxa2, Mef2c, BMPs, IGF, HGF, WNT, FGF, KGF, bFGF, Klf4, CRX, RAX, OTX2, Ascl1, NFIA, NFIB, Fezf2, Hmga2, VEGF, LIF, TGF-β, SOX2, Noggin, nodal, Brn2, Mytl1, NeuroD1, Hnf1a, Foxa3, Tbx5, Tymosin beta4, Tbx5, EGF, SOXs, Bestrophin1, Ctip2, NeuroG2, Atf5, Prox1, Hnf4a, OCT4, TERT, c-myc, insulin, FGFs, interleukins, miR-124 family, miR-9 family, miR-155 family, miR-302 family, miR-367 family and miR-21 family.

4. The composition according to claim 1, wherein the cell fate modulating factor is at least one selected from the group consisting of retinoic acid, CYC, activin A, BMP-4, KGF, bFGF, Noggin, Wnt, Oct4, Sox2, Klf4, c-myc, Nanog, TERT, miR-21, 5-azacytidine, Kortogenin, CHIR, TGF-β Inhibitor, FSK, DZNep, and TGFbeta-1.

5. The composition according to claim 1, wherein the cell fate modulating factor is a fate modulating factor of at least one selected from the group consisting of: embryonic stem cell, adult stem cell, induced multipotent stem cell, mesenchymal stem cell, dermoblast, lymphocyte, myelocyte, neural progenitor cell, spinal cell, adipocyte, hepatocyte, dermal cell, hemocyte, myeloblast, fibroblast, endothelial cell, nerve cell, muscle cell, immunocyte, myocardial cell, brain cell, bone cell, oral cell, periodontal cell, hair follicle cell, mucosa cell, epithelial cell, mesenchmal cell, mesenchymal cell, placetocyte, cord blood cell, stem cell, gastrointestinal tract cell, amnion cell, retinal cell, cartilage cell, pancreatic cell, pancreatic beta cell, vascular cell, and lung fibroblast cell.

6. The composition according to claim 1, wherein the particle has at least one functional group selected from the group consisting of aldehyde, keto, carbamate, sulfate, sulfonate, amino, amine, aminoalkyl, silyl, carboxyl, sulfonic acid, thiol, ammonium, sulfhydryl, phosphate, imide, thioimide, ether, indene, sulfonyl, methyl phosphonate, polyethylene glycol, substituted $C_1$ to $C_{30}$ alkyl, unsubstituted $C_1$ to $C_{30}$ alkyl, substituted $C_3$ to $C_{30}$ cycloalkyl, unsubstituted $C_3$ to $C_{30}$ cycloalkyl, substituted $C_6$ to $C_{30}$ aryl, unsubstituted $C_6$ to $C_{30}$ aryl, and a $C_1$ to $C_{30}$ ester group on the surface of the particle or inside the pores of the particle.

7. The composition according to claim 1, wherein the particle has at least one selected from the group consisting of amino, amine, PEG, propyl, octyl, carboxyl, thiol, sulfonic acid, methyl phosphonate and aldehyde groups on the surface of the particle or inside the pores of the particle.

8. The composition according to claim 1, wherein the maximum amount of releasing the cell fate modulating factor carried in the particle is 99% by weight or more, but not more than 100 % by weight.

9. The composition according to claim 1, wherein the pores in the particle have an average diameter of 1 to 25 nm, a pore volume of 0.3 to 2 ml/g, and a BET surface area of 200 to 1500 $m^2/g$.

10. The composition according to claim 1, wherein the pores in the particle have an average diameter of 7 to 23 nm, a pore volume of 0.59 to 1.69 ml/g and a BET surface area of 250 to 950 $m^2/g$.

11. The composition according to claim 1, wherein the cell fate modulating factor is a gene encoding: at least one selected from the group consisting of Dkk1, Lefty A, activin A, GATA4, Foxa1, Foxa2, Mef2c, BMPs, IGF, HGF, WNT, FGF, KGF, bFGF, Klf4, CRX, RAX, OTX2, Ascl1, NFIA, NFIB, Fezf2, Hmga2, VEGF, LIF, TGF-β, SOX2, Noggin, nodal, Brn2, Myt1, NeuroD1, Hnf1a, Foxa3, Tbx5, Tymosin beta4, Tbx5, EGF, SOXs, Bestrophin1, Ctip2, NeuroG2, Atf5, Prox1, Hnf4a, OCT4, TERT, c-myc, insulin, and interleukins.

* * * * *

SEQUENCE LISTING

<160> NUMBER OF SEQ ID NOS: 15

<210> SEQ ID NO 1
<211> LENGTH: 26
<212> TYPE: DNA
<213> ORGANISM: Artificial Sequence
<220> FEATURE:
<223> OTHER INFORMATION: OCT4 forward primer

<400> SEQUENCE: 1
gctcagcctt aagaacatgt gtaagc                                26

<210> SEQ ID NO 2
<211> LENGTH: 23
<212> TYPE: DNA
<213> ORGANISM: Artificial Sequence
<220> FEATURE:
<223> OTHER INFORMATION: OCT4 reverse primer

<400> SEQUENCE: 2
gcctcatact cttctcgttg gga                                   23

<210> SEQ ID NO 3
<211> LENGTH: 20
<212> TYPE: DNA
<213> ORGANISM: Artificial Sequence
<220> FEATURE:
<223> OTHER INFORMATION: Tuj1 forward primer

<400> SEQUENCE: 3
tcagcgatga gcacggcata                                       20

<210> SEQ ID NO 4
<211> LENGTH: 20
<212> TYPE: DNA
<213> ORGANISM: Artificial Sequence
<220> FEATURE:
<223> OTHER INFORMATION: Tuj1 reverse primer

<400> SEQUENCE: 4
cactctttcc gcacgacatc                                       20

<210> SEQ ID NO 5
<211> LENGTH: 1189

<212> TYPE: DNA
<213> ORGANISM: Artificial Sequence
<220> FEATURE:
<223> OTHER INFORMATION: OCT4 gene sequence

<400> SEQUENCE: 5

```
ccttcgcaag ccctcatttc accaggcccc cggcttgggg cgccttcctt ccccatggcg      60
ggacacctgg cttcagattt tgccttctcg cccctccag gtggtggagg tgatgggcca     120
ggggggccgg agccgggctg ggttgatcct cggacctggc taagcttcca aggccctcct    180
ggagggccag gaatcgggcc gggggttggg ccaggctctg aggtgtgggg gattccccca    240
tgccccccgc cgtatgagtt ctgtgggggg atggcgtact gtgggcccca ggttggagtg    300
gggctagtgc cccaaggcgg cttggagacc tctcagcctg agggcgaagc aggagtcggg    360
gtggagagca actccgatgg ggcctccccg gagccctgca ccgtcacccc tggtgccgtg    420
aagctggaga aggagaagct ggagcaaaac ccggaggagt cccaggacat caaagctctg    480
cagaaagaac tcgagcaatt tgccaagctc ctgaagcaga gaggatcac cctgggatat     540
acacaggccg atgtggggct caccctgggg gttctatttg gaaggtatt cagccaaacg     600
accatctgcc gctttgaggc tctgcagctt agcttcaaga acatgtgtaa gctgcggccc    660
ttgctgcaga gtgggtgga ggaagctgac aacaatgaaa atcttcagga gatatgcaaa     720
gcagaaaccc tcgtgcaggc ccgaaagaga aagcgaacca gtatcgagaa ccgagtgaga    780
ggcaacctgg agaatttgtt cctgcagtgc ccgaaaccca cactgcagca gatcagccac    840
atcgcccagc agcttgggct cgagaaggat gtggtccgag tgtggttctg taaccggcgc    900
cagaagggca agcgatcaag cagcgactat gcacaacgag aggattttga ggctgctggg    960
tctcctttct caggggggacc agtgtccttt cctctggccc cagggcccca ttttggtacc   1020
ccaggctatg ggagccctca cttcactgca ctgtactcct cggtcccttt ccctgagggg   1080
gaagcctttc cccctgtctc tgtcaccact ctgggctctc ccatgcattc aaactgaggt   1140
gcctgccctt ctaggaatgg gggacagggg gagggagga gctagggaa                1189
```

<210> SEQ ID NO 6
<211> LENGTH: 1083
<212> TYPE: DNA
<213> ORGANISM: Artificial Sequence
<220> FEATURE:
<223> OTHER INFORMATION: SOX2 gene sequence

<400> SEQUENCE: 6

```
gttcgttgca acaaattgat gagcaatgct tttttataat gccaactttg tacaaaaaag     60
ttggcatgta caacatgatg gagacggagc tgaagccgcc gggcccgcag caaacttcgg    120
ggggcggcgg cggcaactcc accgcggcgg cggccggcgg caaccagaaa aacagcccgg    180
accgcgtcaa gcggcccatg aatgccttca tggtgtggtc ccgcgggcag cggcgcaaga    240
tggcccagga gaaccccaag atgcacaact cggagatcag caagcgcctg ggcgccgagt    300
ggaaactttt gtcggagacg gagaagcggc cgttcatcga cgaggctaag cggctgcgag    360
cgctgcacat gaaggagcac ccggattata ataccggcc ccggcggaaa accaagacgc     420
tcatgaagaa ggataagtac acgctgcccg gcgggctgct ggcccccggc ggcaatagca    480
tggcgagcgg ggtcgggtg ggcgccggcc tgggcgcggg cgtgaaccag cgcatggaca    540
gttacgcgca catgaacggc tggagcaacg gcagctacag catgatgcag gaccagctgg    600
gctacccgca gcacccgggc ctcaatgcgc acggcgcagc gcagatgcag cccatgcacc    660
```

```
gctacgacgt gagcgccctg cagtacaact ccatgaccag ctcgcagacc tacatgaacg      720
gctcgcccac ctacagcatg tcctactcgc agcagggcac ccctggcatg gctcttggct      780
ccatgggttc ggtggtcaag tccgaggcca gctccagccc cctgtggtt acctcttcct       840 cccactccag ggcgccctgc caggccgggg acctccggga catgatcagc atgtatctcc      900
ccggcgccga ggtgccggaa cccgccgccc ccagcagact tcacatgtcc cagcactacc      960
agagcggccc ggtgccggc acggccatta acggcacact gccctctca cacatgtgcc       1020 caactttctt gtacaaagtt ggcattataa gaaagcattg cttatcaatt tgttgcaacg      1080
aac                                                                    1083

<210> SEQ ID NO 7
<211> LENGTH: 2520
<212> TYPE: DNA
<213> ORGANISM: Artificial Sequence
<220> FEATURE:
<223> OTHER INFORMATION: SOX2 gene sequence

<400> SEQUENCE: 7
ggatggttgt ctattaactt gttcaaaaaa gtatcaggag ttgtcaaggc agagaagaga       60
gtgtttgcaa aaggggaaa gtagtttgct gcctctttaa gactaggact gagagaaaga      120
agaggagaga gaaagaaagg gagagaagtt tgagccccag gcttaagcct ttccaaaaaa     180
taataataac aatcatcggc ggcggcagga tcggccagag gaggagggaa gcgctttttt     240
tgatcctgat tccagtttgc ctctctcttt ttttccccca aattattctt cgcctgattt     300
tcctcgcgga gccctgcgct cccgacaccc ccgcccgcct ccctcctcc tctccccccg      360 cccgcgggcc ccccaaagtc ccggccgggc cgaggtcgg cggccgccgg cgggccgggc      420
ccgcgcacag cgcccgcatg tacaacatga tggagacgga gctgaagccg ccgggcccgc     480
agcaaacttc gggggcggc ggcggcaact ccaccgcggc ggcggccggc ggcaaccaga      540
aaaacagccc ggaccgcgtc aagcggccca tgaatgcctt catggtgtgg tcccgcgggc     600
agcggcgcaa gatggcccag gagaacccca agatgcacaa ctcggagatc agcaagcgcc     660
tgggcgccga gtggaaactt tgtcggagac ggagaagcg gccgttcatc gacgaggcta     720
agcggctgcg agcgctgcac atgaaggagc acccggatta taaataccgg cccggcgga      780 aaaccaagac gctcatgaag aaggataagt acacgctgcc cggcgggctg ctggcccccg     840
gcggcaatag catggcgagc ggggtcgggg tgggcgccgg cctgggcgcg ggcgtgaacc     900
agcgcatgga cagttacgcg cacatgaacg gctggagcaa cggcagctac agcatgatgc     960
aggaccagct gggctacccg cagcacccgg gcctcaatgc gcacggcgca gcgcagatgc    1020
agcccatgca ccgctacgac gtgagcgccc tgcagtacaa ctccatgacc agctcgcaga    1080
cctacatgaa cggctcgccc acctacagca tgtcctactc gcagcagggc acccctggca    1140
tggctcttgg ctccatgggt tcggtggtca agtccgaggc cagctccagc ccccctgtgg    1200
ttacctcttc ctcccactcc agggcgccct gccaggccgg ggacctccgg gacatgatca    1260
gcatgtatct ccccggcgcc gaggtgccgg aacccgccgc cccagcaga cttcacatgt     1320 cccagcacta ccagagcggc ccggtgcccg gcacggccat aacggcaca ctgccctct      1380 cacacatgtg agggccggac agcgaactgg agggggaga attttcaaa gaaaaacgag      1440 ggaaatggga ggggtgcaaa agaggagagt aagaaacagc atggagaaaa cccggtacgc    1500
tcaaaaagaa aaaggaaaaa aaaaaatccc atcacccaca gcaaatgaca gctgcaaaag    1560
agaacaccaa tcccatccac actcacgcaa aaaccgcgat gccgacaaga aaactttat    1620
```

| | | |
|---|---|---|
| gagagagatc ctggacttct ttttggggga ctattttgt acagagaaaa cctggggagg | 1680 | |
| gtggggaggg cggggaatg daccttgtat agatctggag gaaagaaagc tacgaaaaac | 1740 | |
| tttttaaaag ttctagtggt acggtaggag ctttgcagga agtttgcaaa agtctttacc | 1800 | |
| aataatattt agagctagtc tccaagcgac gaaaaaatg ttttaatatt tgcaagcaac | 1860 | |
| ttttgtacag tatttatcga gataaacatg gcaatcaaaa tgtccattgt ttataagctg | 1920 | |
| agaatttgcc aatattttc aaggagaggc ttcttgctga attttgattc tgcagctgaa | 1980 | |
| atttaggaca gttgcaaacg tgaaagaag aaaattattc aaatttggac attttaattg | 2040 | |
| tttaaaaatt gtacaaaagg aaaaaattag aataagtact ggcgaaccat ctctgtggtc | 2100 | |
| ttgtttaaaa agggcaaaag ttttagactg tactaaatt tataacttac tgttaaaagc | 2160 | |
| aaaaatggcc atgcaggttg acaccgttgg taatttataa tagcttttgt tcgatcccaa | 2220 | |
| cttttccattt tgttcagata aaaaaaacca tgaaattact gtgtttgaaa tatttttctta | 2280 | |
| tggtttgtaa tatttctgta aatttattgt gatatttaa ggttttcccc ccttatttt | 2340 | |
| ccgtagttgt attttaaaag attcggctct gtattatttg aatcagtctg ccgagaatcc | 2400 | |
| atgtatatat ttgaactaat atcatccta taacaggtac atttcaact taagttttta | 2460 | |
| ctccattatg cacagttga gataaataaa ttttgaaat atggacactg aaaaaaaaaa | 2520 | |

<210> SEQ ID NO 8
<211> LENGTH: 821
<212> TYPE: DNA
<213> ORGANISM: Artificial Sequence
<220> FEATURE:
<223> OTHER INFORMATION: Klf4 gene sequence

<400> SEQUENCE: 8

| | | |
|---|---|---|
| actcgccttg ctgattgtct atttttgcgt ttacaacttt tctaagaact tttgtataca | 60 | |
| aaggaacttt ttaaaaaaga cgcttccaag ttatatttaa tccaaagaag aaggatctcg | 120 | |
| gccaatttgg ggtttgggt tttggcttcg tttcttctct tcgttgactt tggggttcag | 180 | |
| gtgccccagc tgcttcgggc tgccgaggac cttctgggcc cccacattaa tgaggcagcc | 240 | |
| acctggcgag tctgacatgg ctgtcagcga cgcgctgctc ccatctttct ccacgttcgc | 300 | |
| gtctggcccg gcgggaaggg agaagacact gcgtcaagca ggtgccccga ataacagctc | 360 | |
| atgccacccg gttcctgcat gccagaggag cccaagccaa agaggggaag acgatcgtgg | 420 | |
| ccccggaaaa ggaccgccac ccacacttgt gattacgcgg gctgcggcaa aacctacaca | 480 | |
| aagagttccc atctcaaggc acacctgcga acccacacag gtgagaaacc ttaccactgt | 540 | |
| gactgggacg gctgtggatg gaaattcgcc cgctcagatg aactgaccag gcactaccgt | 600 | |
| aaacacacgg gcaccgccc gttccagtgc caaaaatgcg accgagcatt ttccaggtcg | 660 | |
| gaccacctcg ccttacacat gaagaggcat ttttaaatcc cagacagtgg atatgaccca | 720 | |
| cactgccaga agagaattca gtattttta cttttcacac tgtcttcccg atgagggaag | 780 | |
| gagcccagcc agaaagcact acaatcatgg tcaagttccc a | 821 | |

<210> SEQ ID NO 9
<211> LENGTH: 2468
<212> TYPE: DNA
<213> ORGANISM: Artificial Sequence
<220> FEATURE:
<223> OTHER INFORMATION: Klf4 gene sequence

<400> SEQUENCE: 9

-continued

```
taatgaggca gccacctggc gagtctgaca tggctgtcag cgacgcgctg ctcccatctt    60
tctccacgtt cgcgtctggc ccggcgggaa gggagaagac actgcgtcaa gcaggtgccc   120
cgaataaccg ctggcgggag gagctctccc acatgaagcg acttcccccca gtgcttcccg   180 gccgccccta tgacctggcg gcggcgaccg tggccacaga cctggagagc ggcggagccg   240
gtgcggcttg cggcggtagc aacctggcgc ccctacctcg agagagacc gaggagttca   300 acgatctcct ggacctggac tttattctct ccaattcgct gacccatcct ccggagtcag   360
tggccgccac cgtgtcctcg tcagcgtcag cctcctcttc gtcgtcgccg tcgagcagcg   420
gccctgccag cgcgccctcc acctgcagct tcacctatcc gatccgggcc gggaacgacc   480
cgggcgtggc gccgggcggc acgggcggag gcctcctcta tggcagggag tccgctcccc   540
ctccgacggc tcccttcaac ctggcggaca tcaacgacgt gagcccctcg gcggcttcg   600 tggccgagct cctgcggcca gaattggacc cggtgtacat tccgccgcag cagccgcagc   660
cgccaggtgg cgggctgatg ggcaagttcg tgctgaaggc gtcgctgagc gcccctggca   720
gcgagtacgg cagcccgtcg gtcatcagcg tcagcaaagg cagccctgac ggcagccacc   780
cggtggtggt ggcgccctac aacggcgggc cgccgcgcac gtgccccaag atcaagcagg   840
aggcggtctc ttcgtgcacc cacttgggcg ctggaccccc tctcagcaat ggccaccggc   900
cggctgcaca cgacttcccc ctggggcggc agctccccag caggactacc ccgaccctgg   960
gtcttgagga agtgctgagc agcagggact gtcaccctgc cctgccgctt cctcccggct  1020
tccatcccca cccggggccc aattacccat ccttcctgcc cgatcagatg cagccgcaag  1080
tcccgccgct ccattaccaa ggtcagtccc ggggatttgt agctcgggct ggggagccct  1140
gtgtgtgctg gccccacttc gggacacacg ggatgatgct cacccacct tcttcacccc  1200 tagagctcat gccacccggt tcctgcatgc cagaggagcc caagccaaag aggggaagac  1260
gatcgtggcc ccggaaaagg accgccaccc acacttgtga ttacgcgggc tgcggcaaaa  1320
cctacacaaa gagttcccat ctcaaggcac acctgcgaac ccacacaggt gagaaacctt  1380
accactgtga ctgggacggc tgtggatgga aattcgcccg ctcagatgaa ctgaccaggc  1440
actaccgtaa acacacgggg caccgcccgt tccagtgcca aaaatgcgac cgagcatttt  1500
ccaggtcgga ccacctcgcc ttacacatga agaggcattt ttaaatccca gacagtggat  1560
atgacccaca ctgccagaag agaattcagt atttttttact tttcacactg tcttcccgat  1620
gagggaagga gccagccag aaagcactac aatcatggtc aagttcccaa ctgagtcatc  1680
ttgtgagtgg ataatcagga aaaatgagga atccaaaaga caaaaatcaa agaacagatg  1740
gggtctgtga ctggatcttc tatcattcca attctaaatc cgacttgaat attcctggac  1800
ttacaaaatg ccaaggggggt gactggaagt tgtggatatc agggtataaa ttatatccgt  1860
gagttggggg agggaagacc agaattccct tgaattgtgt attgatgcaa tataagcata  1920
aaagatcacc ttgtattctc tttaccttct aaaagccatt attatgatgt tagaagaaga  1980
ggaagaaatt caggtacaga aaacatgttt aaatagccta atgatggtg cttggtgagt  2040 cttggttcta aagtaccaa acaaggaagc caaagttttc aaactgctgc atactttgac  2100
aaggaaaatc tatatttgtc ttccgatcaa catttatgac ctaagtcagg taatatacct  2160
ggtttacttc tttagcattt ttatgcagac agtctgttat gcactgtggt ttcagatgtg  2220
caataatttg tacaatggtt tattcccaag tatgccttaa gcagaacaaa tgtgtttttc  2280
tatatagttc cttgccttaa taaatatgta atataaattt aagcaaacgt ctattttgta  2340
tatttgtaaa ctacaaagta aaatgaacat tttgtggagt ttgtattttg catactcaag  2400
```

```
gtgagaatta agttttaaat aaacctataa tattttataa aaaaaaaaaa aaaaaaaaaa    2460
aaaaaaaa                                                              2468

<210> SEQ ID NO 10
<211> LENGTH: 3014
<212> TYPE: DNA
<213> ORGANISM: Artificial Sequence
<220> FEATURE:
<223> OTHER INFORMATION: Klf4 gene sequence

<400> SEQUENCE: 10
gcagaggcgg tggcgggcgg cggcggcacc gggagccgcc gagtgaccct ccccccgcccc    60 tctggccccc caccctccca cccgcccgtg gcccgcgccc atggccgcgc gcgctccaca   120
caactcaccg gagtccgcgc cttgcgccgc cgaccagttc gcagctccgc gccacgcag    180 ccagtctcac ctggcggcac cgcccgccca ccgccccggc cacagcccct gcgcccacgg   240
cagcactcga ggcgaccgcg acagtggtgg gggacgctgc tgagtggaag agagcgcagc   300
ccggccaccg gacctactta ctcgccttgc tgattgtcta tttttgcgtt tacaactttt   360
ctaagaactt ttgtatacaa aggaactttt taaaaaagac gcttccaagt tatatttaat   420
ccaaagaaga aggatctcgg ccaatttggg gttttgggtt ttggcttcgt ttcttctctt   480
cgttgacttt ggggttcagg tgccccagct gcttcgggct gccgaggacc ttctgggccc   540
ccacattaat gaggcagcca cctggcgagt ctgacatggc tgtcagcgac gcgctgctcc   600
catctttctc cacgttcgcg tctggcccgg cgggaaggga gaagacactg cgtcaagcag   660
gtgccccgaa taaccgctgg cgggaggagc tctcccacat gaagcgactt cccccagtgc   720
ttcccggccg cccctatgac ctggcggcgg cgaccgtggc cacagacctg gagagcggcg   780
gagccggtgc ggcttgcggc ggtagcaacc tggcgcccct acctcggaga gagaccgagg   840
agttcaacga tctcctggac ctggactttat ttctctccaa ttcgctgacc catcctccgg   900
agtcagtggc cgccaccgtg tcctcgtcag cgtcagcctc ctcttcgtcg tcgccgtcga   960
gcagcggccc tgccagcgcg ccctccacct gcagcttcac ctatccgatc cgggccggga  1020
acgacccggg cgtggcgccg ggcggcacgg gcggaggcct cctctatggc agggagtccg  1080 ctcccctcc gacggctccc ttcaacctgg cggacatcaa cgacgtgagc ccctcgggcg  1140
gcttcgtggc cgagctcctg cggccagaat tggacccggt gtacattccg ccgcagcagc  1200
cgcagccgcc aggtggcggg ctgatgggca agttcgtgct gaaggcgtcg ctgagcgccc  1260
ctggcagcga gtacggcagc ccgtcggtca tcagcgtcag caaaggcagc cctgacggca  1320
gccaccccgt ggtggtggcg ccctacaacg gcgggccgcc gcgcacgtgc cccaagatca  1380
agcaggaggc ggtctcttcg tgcacccact tgggcgctgg accccctctc agcaatggcc  1440
accggccggc tgcacacgac ttccccctgg ggcggcagct ccccagcagg actaccccga  1500
ccctgggtct tgaggaagtg ctgagcagca gggactgtca ccctgccctg ccgcttcctc  1560
ccggcttcca tccccacccg ggcccaatt acccatcctt cctgcccgat cagatgcagc  1620
cgcaagtccc gccgctccat taccaaggtc agtcccgggg atttgtagct cgggctgggg  1680
agccctgtgt gtgctggccc cacttcggga cacgcggat gatgctcacc ccaccttctt  1740 caccccctaga gctcatgcca cccggttcct gcatgccaga ggagcccaag ccaaagaggg  1800
gaagacgatc gtgccccgg aaaaggaccg ccacccacac ttgtgattac gcgggctgcg  1860
gcaaaaccta cacaaagagt tcccatctca aggcacacct gcgaacccac acaggtgaga  1920
```

| | |
|---|---|
| aaccttacca ctgtgactgg gacggctgtg gatggaaatt cgcccgctca gatgaactga | 1980 |
| ccaggcacta ccgtaaacac acggggcacc gcccgttcca gtgccaaaaa tgcgaccgag | 2040 |
| cattttccag gtcggaccac ctcgccttac acatgaagag gcatttttaa atcccagaca | 2100 |
| gtggatatga cccacactgc cagaagagaa ttcagtattt tttactttc acactgtctt | 2160 |
| cccgatgagg gaaggagccc agccagaaag cactacaatc atggtcaagt tcccaactga | 2220 |
| gtcatcttgt gagtggataa tcaggaaaaa tgaggaatcc aaaagacaaa aatcaaagaa | 2280 |
| cagatggggt ctgtgactgg atcttctatc attccaattc taaatccgac ttgaatattc | 2340 |
| ctggacttac aaaatgccaa gggggtgact ggaagttgtg gatatcaggg tataaattat | 2400 |
| atccgtgagt tgggggaggg aagaccagaa ttcccttgaa ttgtgtattg atgcaatata | 2460 |
| agcataaaag atcaccttgt attctcttta ccttctaaaa gccattatta tgatgttaga | 2520 |
| agaagaggaa gaaattcagg tacagaaaac atgtttaaat agcctaaatg atggtgcttg | 2580 |
| gtgagtcttg gttctaaagg taccaaacaa ggaagccaaa gttttcaaac tgctgcatac | 2640 |
| tttgacaagg aaaatctata tttgtcttcc gatcaacatt tatgacctaa gtcaggtaat | 2700 |
| atacctggtt tacttcttta gcattttat gcagacagtc tgttatgcac tgtggtttca | 2760 |
| gatgtgcaat aatttgtaca atggtttatt cccaagtatg ccttaagcag aacaaatgtg | 2820 |
| tttttctata tagttccttg ccttaataaa tatgtaatat aaatttaagc aaacgtctat | 2880 |
| tttgtatatt tgtaaactac aaagtaaaat gaacattttg tggagtttgt attttgcata | 2940 |
| ctcaaggtga gaattaagtt ttaaataaac ctataatatt ttataaaaaa aaaaaaaaa | 3000 |
| aaaaaaaaaa aaaa | 3014 |

<210> SEQ ID NO 11
<211> LENGTH: 4518
<212> TYPE: DNA
<213> ORGANISM: Artificial Sequence
<220> FEATURE:
<223> OTHER INFORMATION: c-myc gene sequence

<400> SEQUENCE: 11

| | |
|---|---|
| ggagtttatt cataacgcgc tctccaagta tacgtggcaa tgcgttgctg ggttatttta | 60 |
| atcattctag gcatcgtttt cctccttatg cctctatcat tcctccctat ctacactaac | 120 |
| atcccacgct ctgaacgcgc gcccattaat accttctttt cctccactct ccctgggact | 180 |
| cttgatcaaa gcgcggccct ttccccagcc ttagcgaggc gccctgcagc ctggtacgcg | 240 |
| cgtggcgtgg cggtgggcgc gcagtgcgtt ctcggtgtgg agggcagctg ttccgcctgc | 300 |
| gatgatttat actcacagga caaggatgcg gtttgtcaaa cagtactgct acggaggagc | 360 |
| agcagagaaa gggagagggt ttgagaggga gcaaaagaaa atggtaggcg cgcgtagtta | 420 |
| attcatgcgg ctctcttact ctgtttacat cctagagcta gagtgctcgg ctgcccggct | 480 |
| gagtctcctc cccaccttcc ccaccctccc caccctcccc ataagcgccc ctcccggggtt | 540 |
| cccaaagcag agggcgtggg ggaaaagaaa aaagatcctc tctcgctaat ctccgcccac | 600 |
| cggccccttta taatgcgagg gtctggacgg ctgaggaccc ccgagctgtg ctgctcgcgg | 660 |
| ccgccaccgc cggccccgg ccgtccctgg ctcccctcct gcctcgagaa gggcagggct | 720 |
| tctcagaggc ttggcgggaa aaagaacgga gggagggatc gcgctgagta taaaagccgg | 780 |
| ttttcggggc tttatctaac tcgctgtagt aattccagcg agaggcagag ggagcgagcg | 840 |
| ggcggccgga tagggtggaa gagccggggc agcagagctg cgctgcgggc gtcctgggaa | 900 |
| gggagatccg gagcgaatag ggggcttcgc ctctggccca gccctcccgc tgatccccca | 960 |

```
gccagcggtc cgcaaccctt gccgcatcca cgaaactttg cccatagcag cgggcgggca   1020
ctttgcactg gaacttacaa cacccgagca aggacgcgac tctcccgacg cggggaggct   1080
attctgccca tttggggaca cttccccgcc gctgccagga cccgcttctc tgaaaggctc   1140

tccttgcagc tgcttagacg cтggaтттттт ttcgggtagt ggaaaaccag cagcctcccg   1200
cgacgatgcc cctcaacgtt agcttcacca acaggaacta tgacctcgac tacgactcgg   1260

tgcagccgta ттттcтacтgc gacgaggagg agaacttcta ccagcagcag cagcagagcg   1320
agctgcagcc cccggcgccc agcgaggata tctggaagaa attcgagctg ctgcccaccc   1380
cgcccctgtc cctagccgc cgctccgggc tctgctcgcc ctcctacgtt gcggtcacac   1440
ccttctccct tcggggagac aacgacggcg gtggcgggag cttctccacg gccgaccagc   1500

tggagatggt gaccgagctg ctgggaggag acatggtgaa ccagagtttc atctgcgacc   1560
cggacgacga gaccttcatc aaaaacatca tcatccagga ctgtatgtgg agcggcttct   1620
cggccgccgc caagctcgtc tcagagaagc tggcctccta ccaggctgcg cgcaaagaca   1680
gcggcagccc gaaccccgcc cgcggccaca cgtctgctc cacсвccagc ttgtacctgc   1740 aggatctgag cgccgccgcc tcagatgca tcgacccc gaвтggтcттc ccсваccccтc   1800

tcaacgacag cagctcgccc aagtcctgcg cctcgcaaga ctccagcgcc ttctctccgt   1860
cctcggattc tctgctctcc tcgacggagt ccстccccgca gggcagcccc gagcccctgg   1920

tgctccatga ggagacaccg cccaccacca gcagcgactc tgaggaggaa caagaagatg   1980
aggaagaaat cgatgttgtt tctgtggaaa agaggcaggc tcctggcaaa aggtcagagt   2040
ctggatcacc ttctgctgga ggccacagca aacctcctca cagcccactg gtcctcaaga   2100
ggtgccacgt ctccacacat cagcacaact acgcagcgcc tccctccact cggaaggact   2160
atcctgctgc caagagggtc aagttggaca gtgtcagagt cctgagacag atcagcaaca   2220
accgaaaatg caccagcccc aggtcctcgg cacccgagga gaatgtcaag aggcgaacac   2280
acaacgtctt ggagcgccag aggaggaacg agctaaaacg gagctttttt gcctgcgtg   2340 accagatccc ggagttggaa acaatgaaa aggcccccaa ggtagttatc cttaaaaaag   2400
ccacagcata catcctgtcc gtccaagcag aggagcaaaa gctcatttct gaagaggact   2460

tgttgcggaa acgacgagaa cagttgaaac acaaacttga acagctacgg aactcttgtg   2520
cgtaaggaaa agtaaggaaa acgattcctt ctaacagaaa tgtcctgagc aatcacctat   2580
gaacttgttt caaatgcatg atcaaatgca acctcacaac cttggctgag tcttgagact   2640
gaaagattta gccataatgt aaactgcctc aaattggact ttgggcataa aagaacttt   2700

ttatgcttac catctttttt тттттcтттaa cagatttgta tttaagaatt gtttttaaaa   2760 aaтттттaaga tttacacaat gtttctctgt aaatattgcc attaaatgta aataacttta   2820
ataaaacgtt tatagcagtt acacagaatt tcaatcctag tatatagtac ctagtattat   2880
aggtactata aaccctaatt tttttatt aagtacattt tgcttttaa agttgattt   2940

tttctattgt тттагaaaa aataaaataa ctggcaaata tatcattgag ccaaatctta   3000
agttgtgaat gтттггттc gttcttccc ссстcccaacс accaccatcc ctgtttgtt   3060

tcatcaattg ccccttcaga gggtggtctt aagaaaggca agagttttcc tctgttgaaa   3120

tgggtctggg ggccttaagg tctttaagtt cttggaggtt ctaagatgct tcctggagac   3180

tatgataaca gccagagttg acagttagaa ggaatggcag aaggcaggtg agaaggtgag   3240
aggtaggcaa aggagataca agaggtcaaa ggtagcagtt aagtacacaa agaggcataa   3300
```

```
ggactgggga gttgggagga aggtgaggaa gaaactcctg ttactttagt taaccagtgc   3360
cagtcccctg ctcactccaa acccaggaat tctgcccagt tgatggggac acggtgggaa   3420
ccagcttctg ctgccttcac aaccaggcgc cagtcctgtc catgggttat ctcgcaaacc   3480
ccagaggatc tctgggagga atgctactat taaccctatt tcacaaacaa ggaaatagaa   3540
gagctcaaag aggttatgta acttatctgt agccacgcag ataatacaaa gcagcaatct   3600
ggacccattc tgttcaaaac acttaaccct tcgctatcat gccttggttc atctgggtct   3660
aatgtgctga gatcaagaag gtttaggacc taatggacag actcaagtca taacaatgct   3720
aagctctatt tgtgtcccaa gcactcctaa gcattttatc cctaactcta catcaacccc   3780
atgaaggaga tactgttgat ttccccatat tagaagtaga gagggaagct gaggcacaca   3840
aagactcatc cacatgccca agattcactg atagggaaaa gtggaagcga gatttgaacc   3900
caggctgttt actcctaacc tgtccaagcc acctctcaga cgacggtagg aatcagctgg   3960
ctgcttgtga gtacaggagt tacagtccag tgggttatgt ttttttaagtc tcaacatcta   4020 agcctggtca ggcatcagtt cccctttttt tgtgatttat tttgttttta ttttgttgtt   4080
cattgtttaa ttttcctttt tacaatgaga aggtcaccat cttgactcct accttagcca   4140
tttgttgaat cagactcatg acggctcctg ggaagaagcc agttcagatc ataaaataaa   4200
acatatttat tctttgtcat gggagtcatt attttagaaa ctacaaactc tccttgcttc   4260
catccttttt tacatactca tgacacatgc tcatcctgag tccttgaaaa ggtattttg   4320 aacatgtgta ttaattataa gcctctgaaa acctatggcc caaaccagaa atgatgttga   4380
ttatataggt aaatgaagga tgctattgct gttctaatta cctcattgtc tcagtctcaa   4440
agtaggtctt cagctcccctg tactttggga ttttaatcta ccaccaccca taaatcaata   4500 ataattact ttctttga                                                  4518
```

<210> SEQ ID NO 12
<211> LENGTH: 958
<212> TYPE: DNA
<213> ORGANISM: Artificial Sequence
<220> FEATURE:
<223> OTHER INFORMATION: Nanog gene sequence

<400> SEQUENCE: 12

```
gtacaaaaaa gcaggctcca ccatgagtgt ggatccagct tgtccccaaa gcttgccttg     60 cttttgaagca tccgactgta aagaatcttc acctatgcct gtgatttgtg ggcctgaaga   120
aaactatcca tccttgcaaa tgtcttctgc tgagatgcct cacacagaga ctgtctctcc   180
tcttccttcc tccatggatc tgcttattca ggacagccct gattcttcca ccagtcccaa   240
aggcaaacaa cccacttctg cagagaatag tgtcgcaaaa aaggaagaca aggtcccggt   300
caagaaacag aagaccagaa ctgtgttctc ttccacccag ctgtgtgtac tcaatgatag   360
atttcagaga cagaaatacc tcagcctcca gcagatgcaa gaactctcca acatcctgaa   420
cctcagctac aaacaggtga agacctggtt ccagaaccag agaatgaaat ctaagaggtg   480
gcagaaaaac aactggccga agaatagcaa tggtgtgacg cagaaggcct cagcacctac   540
ctaccccagc tctactcttc ctaccaccaa gggatgcctg tgaacccga ctgggaacct   600 tccaatgtgg agcaaccaga cctggaacaa ttcaacctgg agcaaccaga cccagaacat   660
ccagtcctgg agcaaccact cctggaacac tcagacctgg tgcacccaat cctggaacaa   720
tcaggcctga acagtccct tctataactg tggagaggaa tctctgcagt cctgcatgca   780
cttccagcca aattctcctg ccagtgactt ggaggctgcc ttggaagctg ctggggaagg   840
```

```
ccttaatgta atacagcaga ccactaggta ttttagtact ccacaaacca tggatttatt    900
cctaaactac tccatgaaca tgcaacctga agacgtgttg gacccagctt tcttgtac     958
```

<210> SEQ ID NO 13
<211> LENGTH: 2114
<212> TYPE: DNA
<213> ORGANISM: Artificial Sequence
<220> FEATURE:
<223> OTHER INFORMATION: Nanog gene sequence

<400> SEQUENCE: 13

```
attataaatc tagagactcc aggattttaa cgttctgctg gactgagctg gttgcctcat     60
gttattatgc aggcaactca ctttatccca atttcttgat acttttcctt ctggaggtcc    120
tatttctcta acatcttcca gaaaagtctt aaagctgcct taaccttttt tccagtccac    180
ctcttaaatt ttttcctcct cttcctctat actaacatga gtgtggatcc agcttgtccc    240
caaagcttgc cttgctttga agcatccgac tgtaaagaat cttcacctat gcctgtgatt    300
tgtgggcctg aagaaaacta tccatccttg caaatgtctt ctgctgagat gcctcacacg    360
gagactgtct ctcctcttcc ctcctccatg gatctgctta ttcaggacag ccctgattct    420
tccaccagtc ccaaaggcaa acaacccact tctgcagaga atagtgtcgc aaaaaaggaa    480
gacaaggtcc cagtcaagaa acagaagacc agaactgtgt tctcttccac ccagctgtgt    540
gtactcaatg atagatttca gagacagaaa tacctcagcc tccagcagat gcaagaactc    600
tccaacatcc tgaacctcag ctacaaacag gtgaagacct ggttccagaa ccagagaatg    660
aaatctaaga ggtggcagaa aaacaactgg ccgaagaata gcaatggtgt gacgcagaag    720
gcctcagcac ctacctaccc cagcctctac tcttcctacc accagggatg cctggtgaac    780
ccgactggga accttccaat gtggagcaac cagacctgga caattcaac  ctggagcaac    840 cagacccaga acatccagtc ctggagcaac cactcctgga acactcagac ctggtgcacc    900
caatcctgga caatcaggc ctggaacagt cccttctata actgtggaga ggaatctctg    960
cagtcctgca tgcagttcca gccaaattct cctgccagtg acttggaggc tgctttggaa    1020
gctgctgggg aaggccttaa tgtaatacag cagaccacta ggtattttag tactccacaa    1080
accatggatt tattcctaaa ctactccatg aacatgcaac ctgaagacgt gtgaagatga    1140
gtgaaactga tattactcaa tttcagtctg acactggct gaatccttcc tctcccctcc    1200
tcccatccct cataggattt ttcttgtttg gaaaccacgt gttctggttt ccatgatgcc    1260
tatccagtca atctcatgga gggtggagta tggttggagc ctaatcagcg aggtttcttt    1320 ttttttttt cctattggat cttcctggag aaaatacttt ttttttttt tttgagacgg    1380 agtcttgctc tgtcgcccag gctggagtgc agtggcgcgg tcttggctca ctgcaagctc    1440
cgcctcccgg gttcacgcca ttctcctgcc tcagcctccc gagcagctgg gactacaggc    1500
gcccgccacc tcgcccggct aatattttgt attttagta gagacagggt ttcactgtgt    1560
tagccaggat ggtctcgatc tcctgacctt gtgatccgcc cgcctcggcc tcctaacag    1620 ctgggattac aggcgtgagc caccgcgccc tgcctagaaa agacatttta ataaccttgg    1680
ctgctaagga caacattgat agaagccgtc tctggctata gataagtaga tctaatacta    1740
gtttggatat ctttagggtt tagaatctaa cctcaagaat aagaaataca agtacgaatt    1800
ggtgatgaag atgtattcgt attgtttggg attgggaggc tttgcttatt tttttaaaac    1860
tattgaggta aagggttaag ctgtaacata cttaattgat ttcttaccgt ttttggctct    1920
```

| | |
|---|---:|
| gttttgctat atccctaat tgttggttg tgctaatctt tgtagaaaga ggtcttgtat | 1980 |
| ttgctgcatc gtaatgacat gagtactact ttagttggtt taagttcaaa tgaatgaaac | 2040 |
| aaatatttt cctttagttg attttaccct gatttcaccg agtgtttcga tgagtaaata | 2100 |
| tacagcttaa acat | 2114 |

```
<210> SEQ ID NO 14
<211> LENGTH: 4018
<212> TYPE: DNA
<213> ORGANISM: Artificial Sequence
<220> FEATURE:
<223> OTHER INFORMATION: hTERT gene sequence

<400> SEQUENCE: 14
```

| | |
|---|---:|
| caggcagcgc tgcgtcctgc tgcgcacgtg ggaagccctg gccccggcca ccccgcgat | 60 |
| gccgcgcgct ccccgctgcc gagccgtgcg ctccctgctg cgcagccact accgcgaggt | 120 |
| gctgccgctg gccacgttcg tgcggcgcct ggggccccag gctggcggc tggtgcagcg | 180 |
| cggggacccg gcggctttcc gcgcgctggt ggcccagtgc ctggtgtgcg tgccctggga | 240 |
| cgcacggccg cccccccgcc ccccctcctt ccgccaggtg tcctgcctga aggagctggt | 300 |
| ggcccgagtg ctgcagaggc tgtgcgagcg cggcgcgaag aacgtgctgg ccttcggctt | 360 |
| cgcgctgctg gacggggccc gcggggggccc cccgaggcc ttcaccacca gcgtgcgcag | 420 |
| ctacctgccc aacacggtga ccgacgcact gcggggggagc ggggcgtggg gctgctgct | 480 |
| gcgccgcgtg ggcgacgacg tgctggttca cctgctggca cgctgcgcgc tctttgtgct | 540 |
| ggtggctccc agctgcgcct accaggtgtg cgggccgccg ctgtaccagc tcggcgctgc | 600 |
| cactcaggcc cggccccgc acacgctag tggaccccga aggcgtctgg gatgcgaacg | 660 |
| ggcctggaac catagcgtca gggaggccgg ggtccccctg ggcctgccag ccccgggtgc | 720 |
| gaggaggcgc gggggcagtg ccagccgaag tctgccgttg cccaagaggc ccaggcgtgg | 780 |
| cgctgcccct gagccggagc ggacgcccgt gggcagggg tcctgggccc acccgggcag | 840 |
| gacgcgtgga ccgagtgacc gtggtttctg tgtggtgtca cctgccagac ccgccgaaga | 900 |
| agccacctct ttggagggtg cgctctctgg cacgcgccac tcccacccat ccgtgggccg | 960 |
| ccagcaccac gcgggccccc catccacatc gcggccacca cgtccctggg acacgccttg | 1020 |
| tcccccggtg tacgccgaga ccaagcactt cctctactcc tcaggcgaca aggagcagct | 1080 |
| gcggccctcc ttcctactca gctctctgag gcccagcctg actggcgctc ggaggctcgt | 1140 |
| ggagaccatc tttctgggtt ccaggccctg gatgccaggg actccccgca ggttgccccg | 1200 |
| cctgccccag cgctactggc aaatgcggcc cctgtttctg gagctgcttg gaaccacgc | 1260 |
| gcagtgcccc tacggggtgc tcctcaagac gcactgcccg ctgcgagctg cggtcacccc | 1320 |
| agcagccggt gtctgtgccc gggagaagcc ccagggctct gtggcggccc ccgaggagga | 1380 |
| ggacacagac cccgtcgcc tggtgcagct gctccgccag cacagcagcc cctggcaggt | 1440 |
| gtacggcttc gtgcgggcct gcctgcgccg gctggtgccc ccaggcctct ggggctccag | 1500 |
| gcacaacgaa cgccgcttcc tcaggaacac caagaagttc atctccctgg ggaagcatgc | 1560 |
| caagctctcg ctgcaggagc tgacgtggaa gatgagcgtg cgggactgcg cttggctgcg | 1620 |
| caggagccca gggggttggct gtgttccggc cgcagagcac cgtctgcgtg aggagatcct | 1680 |
| ggccaagttc ctgcactggc tgatgagtgt gtacgtcgtc gagctgctca ggtctttctt | 1740 |
| ttatgtcacg gagaccacgt tcaaaaagaa caggctcttt ttctaccgga agagtgtctg | 1800 |
| gagcaagttg caaagcattg gaatcagaca gcacttgaag agggtgcagc tgcgggagct | 1860 |

-continued

| | |
|---|---|
| gtcggaagca gaggtcaggc agcatcggga agccaggccc gccctgctga cgtccagact | 1920 |
| ccgcttcatc cccaagcctg acgggctgcg gccgattgtg aacatggact acgtcgtggg | 1980 |
| agccagaacg ttccgcagag aaaagagggc cgagcgtctc acctcgaggg tgaaggcact | 2040 |
| gttcagcgtg ctcaactacg agcgggcgcg gcgccccggc ctcctgggcg cctctgtgct | 2100 |
| gggcctggac gatatccaca gggcctggcg caccttcgtg ctgcgtgtgc gggcccagga | 2160 |
| cccgccgcct gagctgtact ttgtcaaggt ggatgtgacg ggcgcgtacg acaccatccc | 2220 |
| ccaggacagg ctcacggagg tcatcgccag catcatcaaa ccccagaaca cgtactgcgt | 2280 |
| gcgtcggtat gccgtggtcc agaaggccgc ccatgggcac gtccgcaagg ccttcaagag | 2340 |
| ccacgtctct accttgacag acctccagcc gtacatgcga cagttcgtgg ctcacctgca | 2400 |
| ggagaccagc ccgctgaggg atgccgtcgt catcgagcag agctcctccc tgaatgaggc | 2460 |
| cagcagtggc ctcttcgacg tcttcctacg cttcatgtgc caccacgccg tgcgcatcag | 2520 |
| gggcaagtcc tacgtccagt gccagggat cccgcagggc tccatcctct ccacgctgct | 2580 |
| ctgcagcctg tgctacggcg acatggagaa caagctgttt gcggggattc ggcgggacgg | 2640 |
| gctgctcctg cgtttggtgg atgatttctt gttggtgaca cctcacctca cccacgcgaa | 2700 |
| aaccttcctc aggaccctgg tccgaggtgt ccctgagtat ggctgcgtgg tgaacttgcg | 2760 |
| gaagacagtg gtgaacttcc ctgtagaaga cgaggccctg ggtggcacgg cttttgttca | 2820 |
| gatgccggcc cacggcctat tccctggtg cggcctgctg ctggatacc ggaccctgga | 2880 |
| ggtgcagagc gactactcca gctatgcccg gacctccatc agagccagtc tcaccttcaa | 2940 |
| ccgcggcttc aaggctggga ggaacatgcg tcgcaaactc tttggggtct tgcggctgaa | 3000 |
| gtgtcacagc ctgttctgg atttgcaggt gaacagcctc cagacggtgt gcaccaacat | 3060 |
| ctacaagatc ctcctgctgc aggcgtacag gtttcacgca tgtgtgctgc agctcccatt | 3120 |
| tcatcagcaa gtttggaaga accccacatt tttcctgcgc gtcatctctg acacggcctc | 3180 |
| cctctgctac tccatcctga agccaagaa cgcagggatg tcgctggggg ccaagggcgc | 3240 |
| cgccggccct ctgccctccg aggccgtgca gtggctgtgc caccaagcat tcctgctcaa | 3300 |
| gctgactcga caccgtgtca cctacgtgcc actcctgggg tcactcagga cagcccagac | 3360 |
| gcagctgagt cggaagctcc cggggacgac gctgactgcc ctggaggccg cagccaaccc | 3420 |
| ggcactgccc tcagacttca agaccatcct ggactgatgg ccacccgccc acagccaggc | 3480 |
| cgagagcaga caccagcagc cctgtcacgc cgggctctac gtcccaggga gggaggggcg | 3540 |
| gcccacaccc aggcccgcac cgctgggagt ctgaggcctg agtgagtgtt tggccgaggc | 3600 |
| ctgcatgtcc ggctgaaggc tgagtgtccg gctgaggcct gagcgagtgt ccagccaagg | 3660 |
| gctgagtgtc cagcacacct gccgtcttca cttccccaca ggctggcgct cggctccacc | 3720 |
| ccagggccag cttttcctca ccaggagccc ggcttccact ccccacatag gaatagtcca | 3780 |
| tccccagatt cgccattgtt cacccctcgc cctgccctcc tttgccttcc accccacca | 3840 |
| tccaggtgga gaccctgaga aggaccctgg gagctctggg aatttggagt gaccaaaggt | 3900 |
| gtgccctgta cacaggcgag gaccctgcac ctggatgggg gtccctgtgg gtcaaattgg | 3960 |
| ggggaggtgc tgtgggagta aaatactgaa tatatgagtt tttcagtttt gaaaaaaa | 4018 |

<210> SEQ ID NO 15
<211> LENGTH: 22
<212> TYPE: RNA
<213> ORGANISM: Artificial Sequence
<220> FEATURE:

<223> OTHER INFORMATION: miR-21 gene sequence

<400> SEQUENCE: 15
uagcuuauca gacugauguu ga        22